(12) United States Patent
Tani et al.

(10) Patent No.: US 9,087,642 B2
(45) Date of Patent: Jul. 21, 2015

(54) PHOTOELECTRIC CONVERSION ELEMENT, PHOTOELECTROCHEMICAL CELL, AND METAL COMPLEX DYE USED THEREIN

(71) Applicant: FUJIFILM Corporation, Minato-ku, Tokyo (JP)

(72) Inventors: Yukio Tani, Ashigarakami-gun (JP); Tatsuya Susuki, Ashigarakami-gun (JP); Katsumi Kobayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/229,142

(22) Filed: Mar. 28, 2014

(65) Prior Publication Data

US 2014/0209172 A1 Jul. 31, 2014

Related U.S. Application Data

(63) Continuation of application No. PCT/JP2012/074780, filed on Sep. 26, 2012.

(30) Foreign Application Priority Data

Sep. 29, 2011 (JP) .................. 2011-214661
Sep. 25, 2012 (JP) .................. 2012-211587

(51) Int. Cl.
*H01L 51/00* (2006.01)
*H01G 9/20* (2006.01)
(Continued)

(52) U.S. Cl.
CPC .......... *H01G 9/2059* (2013.01); *C07F 15/0026* (2013.01); *C07F 15/0053* (2013.01); *C09B 23/105* (2013.01); *C09B 57/10* (2013.01);
(Continued)

(58) Field of Classification Search
USPC .......................................... 136/252, 256, 263
See application file for complete search history.

(56) References Cited

U.S. PATENT DOCUMENTS 5,463,057 A 10/1995 Graetzel et al.
2010/0258175 A1 10/2010 Chi et al.

FOREIGN PATENT DOCUMENTS

JP 2001-291534 A 10/2001
JP 2004-296170 A 10/2004
(Continued)

OTHER PUBLICATIONS

Bo-So Chen et al., "Neutral, panchromatic Ru(II) terpyridine sensitizers bearing pyridine pyrazolate chelates with superior DSSC performance," Chem. Commun., 2009, pp. 5844-5846.
(Continued)

*Primary Examiner* — Susan D Leong
(74) *Attorney, Agent, or Firm* — Sughrue Mion, PLLC

(57) ABSTRACT

A photoelectric conversion element having a laminate structure including, provided on an electrically conductive support, a photoconductor layer having a layer of dye-adsorbed semiconductor fine particles, a charge transfer layer, and a counter electrode, wherein the dye is a metal complex dye represented by the following formula (1):

$$M^1 L^1 L^2 Z^1 \qquad (1)$$

wherein, in formula (1), $M^1$ represents a metal atom; $Z^1$ represents a monodentate ligand; $L^1$ represents a specific tridentate ligand; and $L^2$ represents a specific bidentate ligand.

12 Claims, 2 Drawing Sheets

(51) Int. Cl.
    *C09B 57/10*     (2006.01)
    *C09B 23/10*     (2006.01)
    *C07F 15/00*     (2006.01)
(52) U.S. Cl.
    CPC .......... *H01G9/2063* (2013.01); *H01L 51/0086* (2013.01); *H01G 9/2022* (2013.01); *H01G 9/2031* (2013.01); *H01L 51/0064* (2013.01); *H01L 51/0068* (2013.01); *H01L 51/0072* (2013.01); *Y02E 10/542* (2013.01); *Y02E 10/549* (2013.01)

(56) References Cited

FOREIGN PATENT DOCUMENTS

| JP | 2007-277166 A | 10/2007 |
| JP | 2009-051999 A | 3/2009 |
| JP | 2009-067976 A | 4/2009 |

OTHER PUBLICATIONS

International Search Report of PCT/JP2012/074780 dated Dec. 18, 2012.

PHOTOELECTRIC CONVERSION ELEMENT, PHOTOELECTROCHEMICAL CELL, AND METAL COMPLEX DYE USED THEREIN

CROSS REFERENCE TO RELATED APPLICATIONS

This application claims priority on Patent Application No. 2011-214661 filed in Japan on Sep. 29, 2011, and Patent Application No. 2012-211587 filed in Japan on Sep. 25, 2012, each of which is entirely herein incorporated by reference.

TECHNICAL FIELD

The present invention relates to a photoelectric conversion element, a photoelectrochemical cell, and a metal complex dye used therein.

BACKGROUND ART

Photoelectric conversion elements are used in various photosensors, copying machines, solar cells, and the like. These photoelectric conversion elements have adopted various systems to be put into use, such as elements utilizing metals, elements utilizing semiconductors, elements utilizing organic pigments or dyes, or combinations of these elements. Solar cells that make use of non-exhaustive solar energy do not necessitate fuels, and full-fledged practicalization of solar cells as an inexhaustible clean energy is being highly expected. Among these, research and development of silicon-based solar cells have long been in progress. Due partly to many countries' policy-wise considerations, dissemination of silicon-based solar cells is still in progress. However, silicon is an inorganic material, and has limitations per se in terms of throughput and molecular modification.

Under such circumstances, research is being vigorously carried out on dye-sensitized solar cells. Especially, to have built momentum toward such research is research results by Graetzel et al of École Polytechnique Fédérale de Lausanne in Switzerland. They employed a structure in which a dye formed from a ruthenium complex was fixed at the surface of a porous titanium oxide thin film, and realized a conversion efficiency that was comparable to that of amorphous silicon. Thus, the dye-sensitized solar cells instantly attracted the attention of researchers all over the world.

Patent Literature 1 describes a dye-sensitized photoelectric conversion element making use of semiconductor fine particles sensitized by a ruthenium complex dye, to which the foregoing technology has been applied. Further still toward the improvement of photoelectric conversion efficiency, development of ruthenium complex-based sensitizing dyes is being continued (see Patent Literature 2).

CITATION LIST

Patent Literatures

Patent Literature 1: U.S. Pat. No. 5,463,057
Patent Literature 2: US 2010/0258175 A1

DISCLOSURE OF INVENTION

Technical Problem

As a terpyridyl-based dye, N749 is in heavy usage. The above-described Patent Literature 2 discloses an improved product of such dye. With respect to these dyes, $\epsilon$ in the short wavelength side is improved, whereas $\epsilon$ in the side of long wavelength of not shorter than 700 nm is low. The improvement of $\epsilon$ allows reducing the amount of the dye to be used. However, in order to make an efficient use of light in the long wavelength side, improvement of in the side of long wavelength of not shorter than 700 nm has been a problem to be addressed.

In view of the current situation in this technical field, the present invention aims to provide a photoelectric conversion element, a photoelectrochemical cell, and a dye used therein, each of which is improved with $\epsilon$ in the side of long wavelength and is able to realize both heat resistance and durability in a high level. Further, the present invention aims to provide, by achieving high photoelectric conversion efficiency using the above-described dye, a photoelectric conversion element, a photoelectrochemical cell, and a metal complex dye used therein, each of which has highs in the long wavelength side and high IPCE (Incident Photon-to-Current Efficiency).

Solution to Problem

The above problems can be solved by the following means:
<1> A photoelectric conversion element having a laminate structure including, provided on a side of an electrically conductive support, a photoconductor layer having a layer of dye-adsorbed semiconductor fine particles, a charge transfer layer, and a counter electrode, wherein the dye is a metal complex dye represented by the following formula (1):

$$M^1 L^1 L^2 Z^1 \qquad (1)$$

wherein, in formula (1), $M^1$ represents a metal atom; $Z^1$ represents a monodentate ligand; $L^1$ represents a tridentate ligand represented by formula (L1); and $L^2$ represents a bidentate ligand represented by formula (L2),

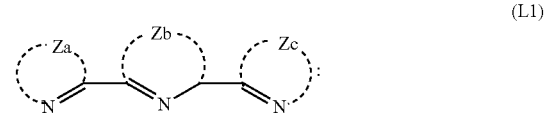

wherein, in formula ($L^1$), Za, Zb, and Zc represent a group of non-metallic atoms necessary for forming a 5- or 6-membered ring; and at least one ring formed by Za, Zb or Zc has an acidic group;

wherein, in formula ($L^2$), $R^1$ represents an alkyl group, an alkylthio group, an alkoxy group, a halogen atom, or an aromatic group; m1 represents an integer of 0 to 3; and E is represented by any one of formulae (L2-1) to (L2-6):

(L2-2)
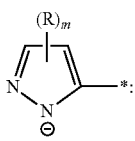

(L2-3)
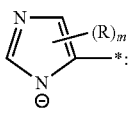

(L2-4)
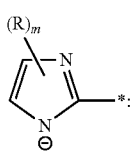

(L2-5)
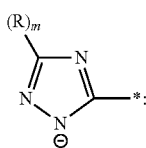

(L2-6)
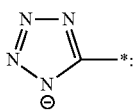

wherein, in formulae (L2-1) to (L2-6), R represents an alkyl group, an alkoxy group, a halogen atom, an aromatic group, or a heterocyclic group; m represents an integer of 0 or more; the symbol "*" represents a binding site with the pyridine ring; and $G^1$ is represented by any one of formulae (G1-1) to (G1-7):

(G1-1)
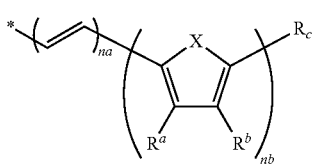

(G1-2)
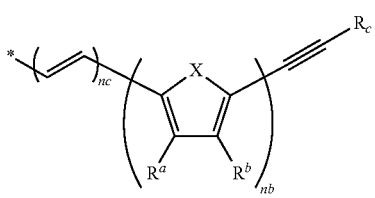

(G1-3)
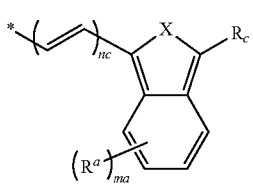

(G1-4)
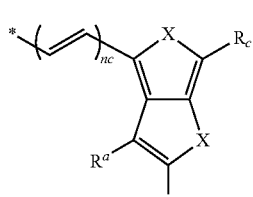

(G1-5)
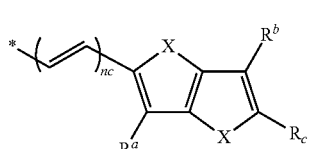

(G1-6)
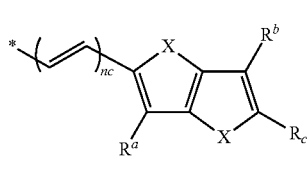

(G1-7)
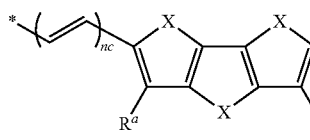

wherein, in formulae (G1-1) to (G1-7), X represents an O atom, a S atom, a Se atom, $NR^A$, $CR^A_2$, or $SiR^A_2$; $R^A$ represents a hydrogen atom, an alkyl group, or an aromatic group; na represents an integer of 0 to 3; nb represents an integer of 1 to 3; nc represents an integer of 0 to 2; ma represents an integer of 0 to 4; and in formula (G1-1), the sum of na and nb is 2 or more, and $R^a$, $R^b$, $R^d$ and $R^e$ each independently represent a hydrogen atom, an alkyl group, an alkoxy group, an alkylthio group, or an amino group; and $R^c$ represents a hydrogen atom, an alkyl group, an alkenyl group, an alkynyl group, an alkoxy group, an alkylthio group, or an amino group.

<2> The photoelectric conversion element described in the above item <1>, wherein $M^1$ is Ru.

<3> The photoelectric conversion element described in the above item <1> or <2>, wherein $L^1$ is represented by formula (L1-2):

(L1-2)
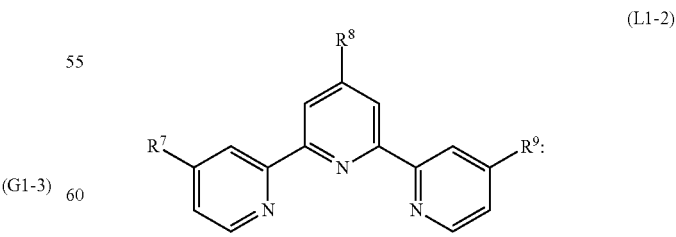

wherein, in formula (L1-2), $R^7$, $R^8$ and $R^9$ each independently represent a hydrogen atom, an alkyl group, a heteroaryl group, an aryl group, or an acidic group; and at least one of $R^7$, $R^8$ and $R^9$ represents an acidic group.

<4> The photoelectric conversion element described in any one of the above items <1> to <3>, wherein the metal complex dye is represented by formula (1-1):

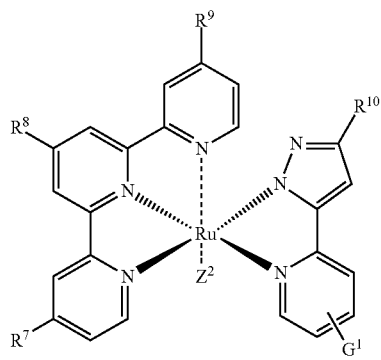

(1-1)

wherein, in formula (1-1), $R^7$ to $R^9$ have the same meanings as those of formula (L1-2); $Z^2$ represents an isothiocyanate group, an isoselenocyanate group, an isocyanate group, a halogen atom, or a cyano group;
$G^1$ has the same meaning as that of formula (L2); and $R^{10}$ represents a hydrogen atom, an alkyl group, a perfluoroalkyl group, an aromatic group, or a heterocyclic group.

<5> The photoelectric conversion element described in the above item <4>, wherein the metal complex dye is represented by formula (1-2):

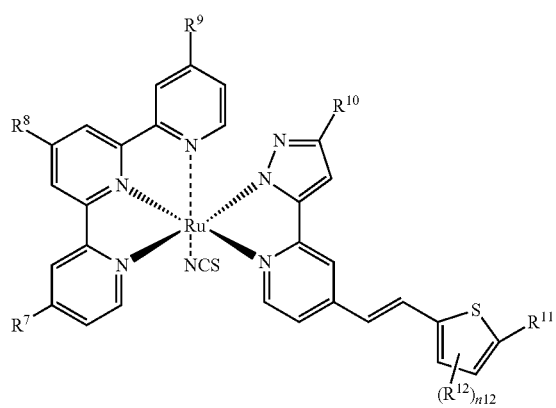

(1-2)

wherein, in formula (1-2), $R^7$ to $R^9$ have the same meaning as those of formula (L1-2); $R^{10}$ has the same meaning as that of formula (1-1); $R^{11}$ represents a hydrogen atom, an alkyl group, an alkoxy group, or an amino group; $R^{12}$ represents an alkyl group, an alkoxy group, or an alkylthio group; and n12 represents an integer of 0 to 2.

<6> The photoelectric conversion element described in any one of the above item <1> to <5>, including semiconductor fine particles sensitized with a plurality of dyes.

<7> The photoelectric conversion element described in the above item <6>, wherein at least one of the dyes has a maximum absorption wavelength of 590 nm or more in tetrabutylammonium hydroxide methanol solution.

<8> The photoelectric conversion element described in any one of the above items <1> to <7>, wherein a co-adsorbent having one or more acid groups is carried on a surface of the semiconductor particles of the semiconductor layer.

<9> The photoelectric conversion element described in the above item <8>, wherein the co-adsorbent is represented by formula (3):

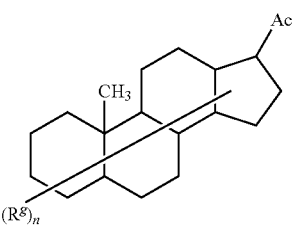

(3)

wherein, in formula (3), Ac represents an acidic group; $R^g$ represents a substituent; and n represents an integer of 0 or more.

<10> A dye-sensitized solar cell, including the photoelectric conversion element described in any one of the above item <1> to <9>.

<11> A metal complex dye represented by formula (1):

$$M^1L^1L^2Z^1 \quad (1)$$

wherein, in formula (1), $M^1$ represents a metal atom; $Z^1$ represents a monodentate ligand; $L^1$ represents a tridentate ligand represented by formula (L1); and $L^2$ represents a bidentate ligand represented by formula (L2);

(L1)

wherein, in formula (L1), Za, Zb, and Zc represent a group of non-metallic atoms necessary for forming a 5- or 6-membered ring; and at least one ring formed by Za, Zb or Zc has an acidic group;

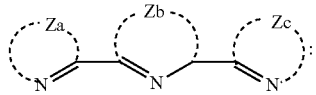

(L2)

wherein, in formula (L2), $R^1$ represents an alkyl group, an alkylthio group, an alkoxy group, a halogen atom, an aromatic group or a heterocyclic group; m1 represents an integer of 0 to 3; and E is represented by any one of formulae (L2-1) to (L2-6):

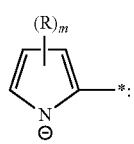

(L2-1)

-continued

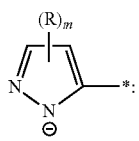
(L2-2)

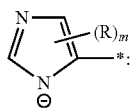
(L2-3)

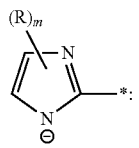
(L2-4)

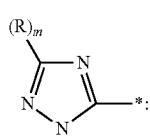
(L2-5)

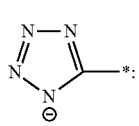
(L2-6)

wherein, in formulae (L2-1) to (L2-6), R represents an alkyl group, an alkoxy group, a halogen atom, an aromatic group, or a heterocyclic group; m represents an integer of 0 or more; the symbol "*" represents a binding site with the pyridine ring; and $G^1$ is represented by any one of formulae (G 1-1) to (G 1-7):

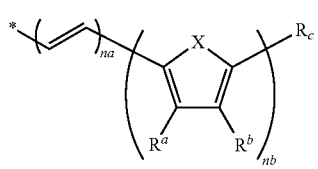
(G1-1)

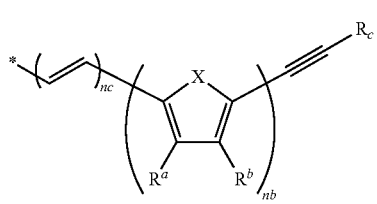
(G1-2)

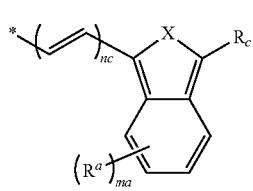
(G1-3)

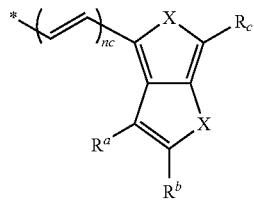
(G1-4)

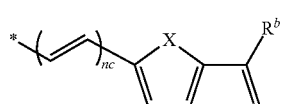
(G1-5)

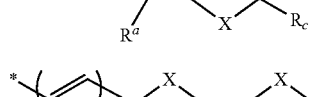
(G1-6)

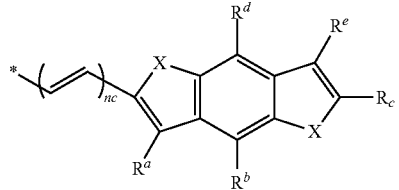
(G1-7)

wherein, in formulae (G1-1) to (G1-7), X represents an O atom, a S atom, a Se atom, $NR^A$, $CR^A_2$, or $SiR^A_2$; $R^A$ represents a hydrogen atom, an alkyl group, or an aromatic group; na represents an integer of 0 to 3; nb represents an integer of 1 to 3; nc represents an integer of 0 to 2; ma represents an integer of 0 to 4; and in formula (G1-1), the sum of na and nb is 2 or more, and $R^a$, $R^b$, $R^d$ and $R^e$ each independently represent a hydrogen atom, an alkyl group, an alkoxy group, an alkylthio group, or an amino group; and $R^c$ represents a hydrogen atom, an alkyl group, an alkenyl group, an alkynyl group, an alkoxy group, an alkylthio group, or an amino group.

In the present specification, the aromatic ring is used in a meaning including an aromatic ring and a heterocyclic ring (an aromatic heterocyclic ring and a heterocyclic ring which does not have aromaticity), and it may be a single ring or a multi ring. With respect to the carbon-carbon double bond, in a case where the E configuration and the Z configuration exist in the molecule, it may be either one of the two configurations. When there are two or more substituents represented by a specific symbol, or when two or more substituents or ligands (including numbers of the substituent) are defined at the same time or alternatively, each of the substituents or the ligands or the like may be the same or different from one another. When a plurality of substituents or ligands are close to one another, they may be linked to one another, or may be ring-fused to form a ring.

Advantageous Effects of Invention

By the high photoelectric conversion element, the photochemical cell, and the metal complex dye used therein, of the present invention, the ε in the long wavelength side can be improved, and also both heat resistance and durability can be realized in a high level. Further, according to the present invention, high photoelectric conversion efficiency is achieved, and excellent device performances which are both high in the long wavelength side and high IPCE (Incident Photon-to-Current Efficiency) are exerted.

Other and further features and advantages of the invention will appear more fully from the following description, appropriately referring to the accompanying drawing.

MODE FOR CARRYING OUT THE INVENTION

The dye of the present invention has a structure in which a nitrogen-containing tridentate ligand and a nitrogen-containing bidentate ligand are coordinated to a central metal, and by this, in the photoelectric conversion element, high IPCE is exerted even in the region of such a long wavelength that exceeds 700 nm, and high E and high photoelectric conversion efficiency are achieved.

The reason is still unclear in a part. However, the reason, including an assumption, may be explained as follows. The dye of the present invention having the specific structure containing a hetero ring-containing ligand contributes to expansion of the conjugated system. It is assumed that this improves c in the long wavelength side. Especially, expansion of the conjugated system due to introduction of a vinyl group exerts the above effects more effectively. Further, when an alkynylene group is introduced, the conjugated system can be expanded with maintaining planarity, and thus the effect on improvement of E is high. Further, when the hetero ring is thiophene, the one-electron oxidation state is stabilized by delocalization, and thus the effect of improvement in durability can be expected. Hereinafter, the present invention is described in detail, based on a preferable embodiment thereof.

[Structure of Element]

Figure 1:
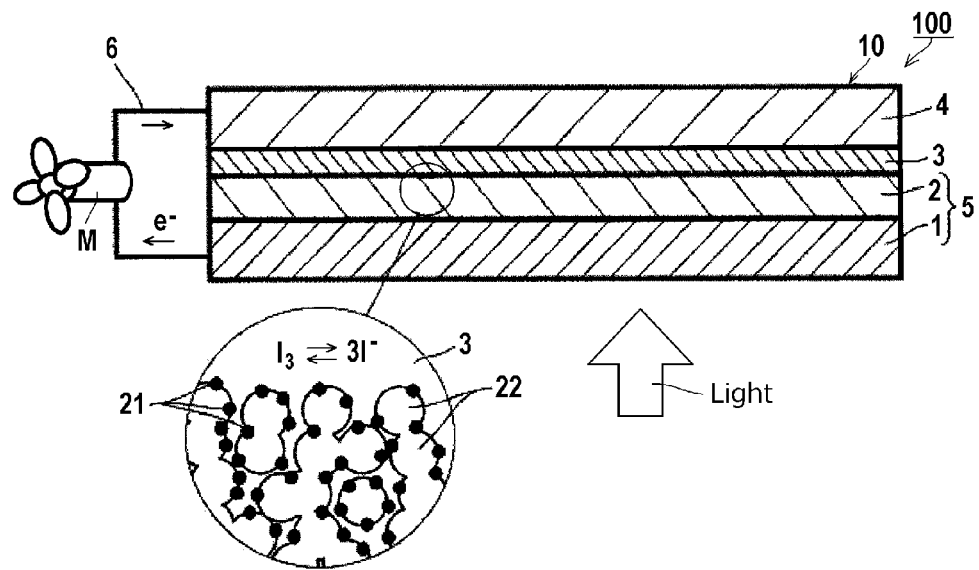
FIG. 1 is a cross-sectional view schematically showing an exemplary embodiment of the photoelectric conversion element according to the present invention.

A preferred embodiment of a photoelectric conversion element, in which the dye of the present invention can be used, will be explained with reference to the drawings. As shown in FIG. 1, a photoelectric conversion element 10 contains an electrically conductive support 1; and a photoconductor layer 2, a charge transfer layer 3 and a counter electrode 4, all provided on the electrically conductive support 1 in this order. The electrically conductive support 1 and the photoconductor layer 2 constitute a light-receiving electrode 5. The photoconductor layer 2 has semiconductor fine particles 22 and a dye 21. The dye 21 is at least partially adsorbed on the semiconductor fine particles 22 (the dye is in an adsorption equilibrium state, and may partially exist in the charge transfer layer). The electrically conductive support 1 having a photoconductor layer 2 provided thereon functions as a working electrode in the photoelectric conversion element 10. This photoelectric conversion element 10 can be operated as a photoelectrochemical cell 100 by making the photoelectric conversion element 10 usable in a cell application where the cell is made to work with an external circuit 6.

The light-receiving electrode 5 is an electrode including an electrically conductive support 1 and a photoconductor layer 2 (semiconductor film) coated on the electrically conductive support 1, the layer containing semiconductor fine particles 22 to which a dye 21 has been adsorbed. A light incident to the photoconductor layer 2 (semiconductor film) excites the dye. The excited dye has electrons with high energy, and these electrons are transported from the dye 21 to the conduction band of the semiconductor fine particles 22 and further reach the electrically conductive support 1 by diffusion. At this time, the molecules of the dye 21 are in an oxidized form. The dye oxidized by excitation accepts electrons from a reducing agent (for example, I⁻) in the electrolyte to return to the dye in the ground state, thereby acting as a photoelectrochemical cell. At this time, the light-receiving electrode 5 works as a negative electrode of this cell.

The photoelectric conversion element according to this embodiment of the present invention includes, on an electrically conductive support, a photoconductor layer that has a layer containing porous semiconductor fine particles on which a dye described below has been adsorbed. A part of the dye at this moment may be dissociated into the electrolyte or so. The photoconductor layer is designed in accordance with the intended use, and may have a single layer structure or a multilayer structure. The photoconductor layer in the photoelectric conversion element according to this embodiment includes semiconductor fine particles on which the specific dye has been adsorbed. Therefore, the photoconductor layer shows high sensitivity, and when used for the photoelectrochemical cell, high conversion efficiency and durability can be achieved.

It is noted that it is not particularly needed to specify the top and bottom of the photoelectric conversion element. In the present specification, however, when describing on the basis of the graphically-illustrated embodiment, the counter electrode 4 side is designated as the upside (top) direction, while the support 1 side that corresponds to the light-receiving side is designated as the underside (bottom) direction.

[Dye Represented by Formula (1)]

The dye of the present invention is represented by the following formula (1).

$$M^1L^1L^2Z^1 \quad (1)$$

<M¹>

M¹ represents a metal atom. M¹ is preferably a metal that is capable of tetracoordination or hexacoordination; more preferably Ru, Fe, Os, Cu, W, Cr, Mo, Ni, Pd, Pt, Co, Ir, Rh, Re, Mn or Zn. Particularly preferably, M¹ is Ru, Os, Zn or Cu, and most preferably Ru.

<L¹>

L¹ is represented by the following formula (L1).

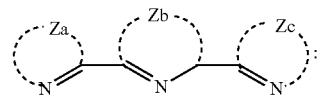

(L1)

Za, Zb and Zc

In formula (L1), Za, Zb and Zc each independently represent a group of non-metallic atoms necessary for forming a 5- or 6-membered ring. At least one ring formed by Za, Zb and Zc has an acidic group.

The 5- or 6-membered ring formed by Za, Zb, or Zc may be substituted or unsubstituted, and it may be a single ring or a condensed ring. The constituent atoms of the ring formed by Za, Zb or Zc are preferably atoms selected from the group consisting of a carbon atom, a nitrogen atom, an oxygen atom, a sulfur atom and a phosphorus atom, and these atoms may be substituted with a substituent including a hydrogen atom and a halogen atom.

The ring formed by Za, Zb or Zc is preferably an aromatic ring. In the case of the 5-membered ring, an imidazole ring, an oxazole ring, a thiazole ring, or a triazole ring is preferably formed. In the case of the 6-membered ring, a pyridine ring, a pyrimidine ring, a pyridazine ring, or a pyrazine ring is preferably formed. Among these rings, an imidazole ring and a pyridine ring are more preferable.

Acidic Group Ac

In the present invention, the acidic group means a substituent having a dissociable proton, and examples thereof include a carboxyl group, a phosphonyl group, a phosphoryl group, a sulfo group, a boric acid group, or a group having any one of these groups. Among these, a carboxyl group and a group having a carboxyl group are preferred. Further, the acidic group may be in a dissociation form due to release of a proton, or may be a salt thereof. In the case of forming a salt, the counter ion is not particularly limited; and examples thereof include the positive ions of the counter ion CI described below. As described above, in the present invention, the acidic group may be a group to which an acidic group binds through a linking group, and preferable examples thereof include a carboxy vinylene group, a dicarboxy vinylene group, a cyanocarboxy vinylene group, and a carboxy phenyl group. It is noted that these acidic groups and a preferable range thereof herein described may be sometimes referred to as acidic group Ac.

$L^1$ is preferably represented by the following formula (L1-1).

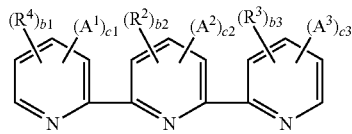
(L1-1)

$A^1$, $A^2$ and $A^3$

In formula (L1-1), $A^1$, $A^2$ and $A^3$ each independently represent an acidic group. $A^1$, $A^2$ and $A^3$ are preferably those exemplified as the acidic group Ac.

$R^2$ to $R^4$ $R^2$ to $R^4$ each independently represent a substituent. Examples of the substituents of $R^2$ to $R^4$ include the substituent T described below. $R^2$ to $R^4$ preferably represent an alkyl group, a heteroaryl group, an aryl group, an alkynyl group, an alkoxy group, and an amino group, more preferably an alkyl group, a heteroaryl group, and an aryl group, and particularly preferably a heteroaryl group.

b1 to b3 and c1 to c3 b1, b3 and c1, c3 each independently represent an integer of 0 to 4, and b2 and c2 each independently represent an integer of 0 to 3. There is no case where all of c1 to c3 are 0.

$L^1$ is more preferably represented by the following formula (L1-2).

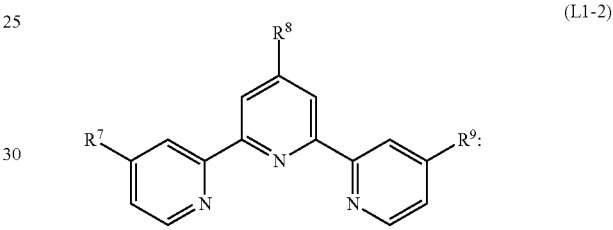
(L1-2)

$R^7$ to $R^9$

In formula (L1-2), $R^7$, $R^8$ and $R^9$ each independently represent a hydrogen group, an alkyl group, a heteroaryl group, an aryl group, or an acidic group. At least one of $R^7$, $R^8$ and $R^9$ is an acidic group, and the acidic group is preferably the acidic group Ac.

Specific examples of $L^1$ are described below, but the present invention is not construed with being limited thereto.

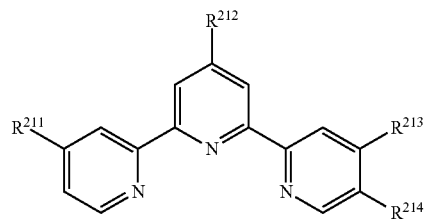

| | $R^{211}$ | $R^{212}$ | $R^{213}$ | $R^{214}$ |
|---|---|---|---|---|
| B-1-1 | —H | —CO$_2$H | —H | —H |
| B-1-2 | —CO$_2$H | —CO$_2$H | —CO$_2$H | —H |
| B-1-3 | —H | —CO$_2$H | —H | —H |
| B-1-4 | —CO$_2$H | —CO$_2$H | —H | 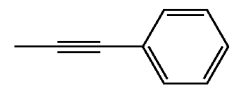 |

-continued

| | | | | |
|---|---|---|---|---|
| B-1-5 | —CO$_2$H | —CO$_2$H | —H | (4-pentyloxyphenyl group) |
| B-1-6 | —H | (5-methylthiophene-2-carboxylic acid group) | —H | —H |
| B-1-7 | —H | —PO$_3$H$_2$ | —H | —H |
| B-1-8 | —H | —CO$_2$H | —CO$_2$H | —H |

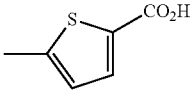

| | $R^{215}$ | $R^{216}$ | $R^{217}$ |
|---|---|---|---|
| B-2-1 | —H | —CO$_2$H | —H |
| B-2-2 | —H | (4-carboxyphenyl) | —H |
| B-2-3 | —$^nC_6H_{13}$ | —CO$_2$H | —H |
| B-2-4 | —$^nC_6H_{13}$ | —CO$_2$H | —$^nC_6H_{13}$ |
| B-2-5 | —H | —PO$_3$H$_2$ | —H |

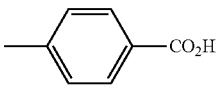

| | $R^{218}$ | $R^{219}$ | $R^{220}$ |
|---|---|---|---|
| B-3-1 | —H | —CO$_2$H | —H |
| B-3-2 | —H | (4-carboxyphenyl) | —H |
| B-3-3 | —$^nC_6H_{13}$ | —CO$_2$H | —H |
| B-3-4 | —$^nC_6H_{13}$ | —CO$_2$H | —$^nC_6H_{13}$ |
| B-3-5 | —H | —PO$_3$H$_2$ | —H |

<$L^2$ (Formula (L2))>
$L^2$ is represented by the following formula (L2).

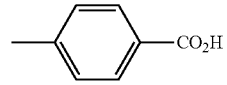
(L2)

$R^1$
$R^1$ represents an alkyl group, an alkylthio group, an alkoxy group, a halogen atom, an aromatic group, or a heterocyclic group. When m1 is 2 or more, plural $R^1$'s may be the same or different from each other, and may bind together to form a ring.

m1
m1 represents an integer of 0 to 3.
E
E is represented by any one of the following formulae (L2-1) to (L2-6).

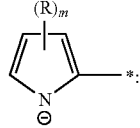
(L2-1)

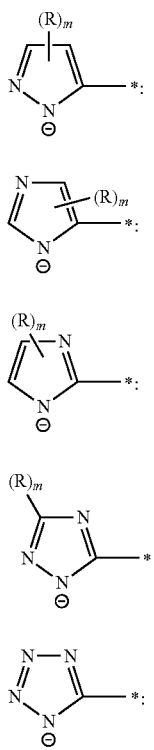

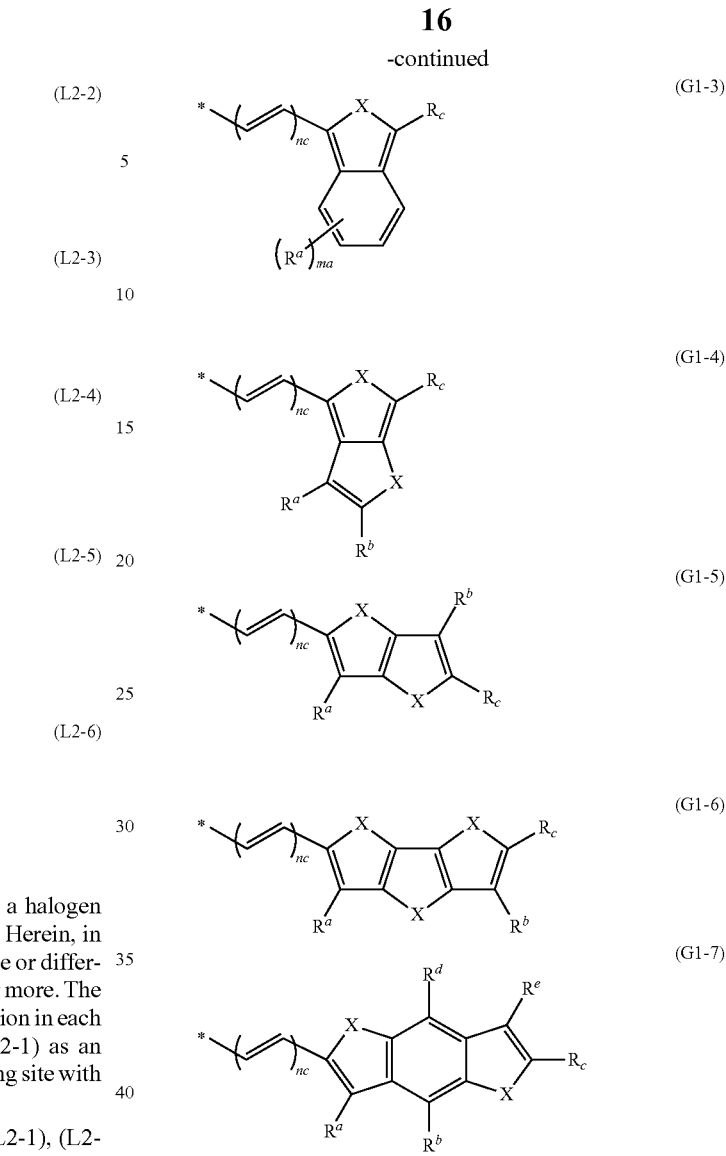

R represents an alkyl group, an alkoxy group, a halogen atom, an aromatic group, or a heterocyclic group. Herein, in a case where plural R's exist, they may be the same or different from each other. m represents an integer of 0 or more. The upper limit of m is the number of possible substitution in each of the formulae, and, in the case of formula (L2-1) as an example, it is 3. The symbol "*" represents a binding site with the pyridine ring Among them, the substituent represented by (L2-1), (L2-2), (L2-4), (L2-5) or (L2-6) is preferred, the substituent represented by (L2-2), (L2-4) or (L2-5) is more preferred, and the substituent represented by (L2-2) is most preferred.

$G^1$ $G^1$ is represented by any one of the following formulae (G1-1) to (G1-7).

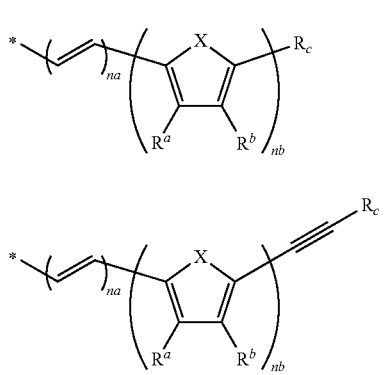

X represents an O atom, a S atom, a Se atom, $NR^A$, $CR^A_2$ or $SiR^A_2$. Herein, $R^A$ represents a hydrogen atom, an alkyl group, or an aromatic group. na represents an integer of 0 to 3. nb represents an integer of 1 to 3. nc represents an integer of 0 to 2. ma represents an integer of 0 to 4. In formula (G1-1), the total of na and nb is 2 or more.

$R^a$, $R^b$, $R^d$, and $R^e$ each independently represent a hydrogen atom, an alkyl group, an alkoxy group, an alkylthio group, or an amino group. $R^c$ represents a hydrogen atom, an alkyl group, an alkenyl group, an alkynyl group, an alkoxy group, an alkylthio group, or an amino group.

Among them, the substituent represented by (G1-1), (G1-2), (G1-3), (G1-5), (G1-6), or (G1-7) is preferred. The substituent represented by (G1-1), (G1-2), (G1-3) or (G1-6) is more preferred, and the substituent represented by (G1-1) or (G1-2) is particularly preferred.

X is preferably a S atom, a Se atom, an O atom, $CR^A_2$ or $SiR^A_2$, more preferably a S atom, an O atom, or $CR^A_2$, and particularly preferably a S atom.

Specific examples of $L^2$ are described below, but the present invention is not construed with being limited thereto.

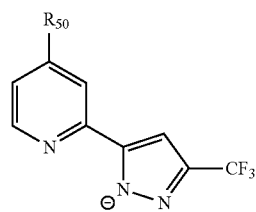
| | $R_{50}$ |
|---|---|
| L2ex1-1 | 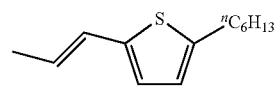 |
| L2ex1-2 | 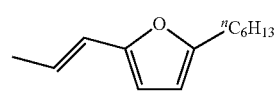 |
| L2ex1-3 | 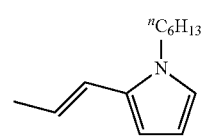 |
| L2ex1-4 | 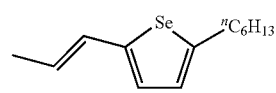 |
| L2ex1-5 | 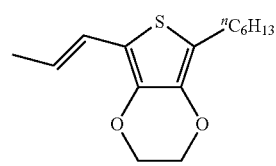 |
| L2ex1-6 | 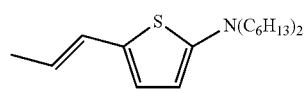 |
| L2ex1-7 | 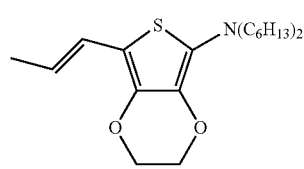 |
| L2ex1-8 | 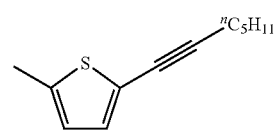 |
| L2ex1-9 | 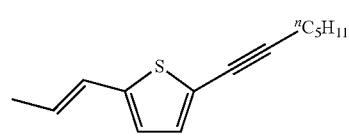 |
| L2ex1-10 | 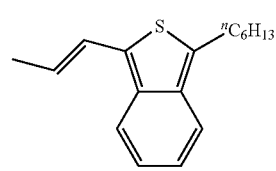 |

-continued
L2ex1-11 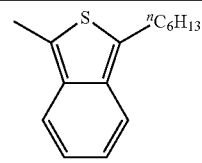
L2ex1-12 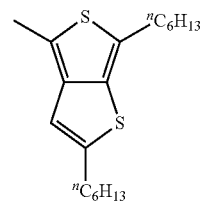
L2ex1-13 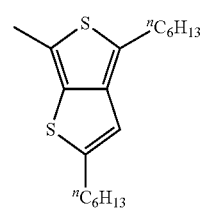
L2ex1-14 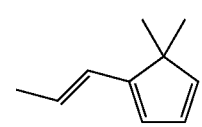
L2ex1-15 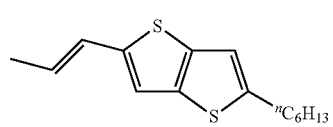
L2ex1-16 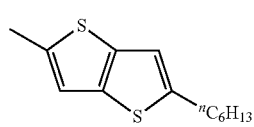
L2ex1-17 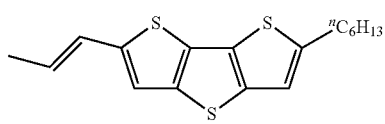
L2ex1-18 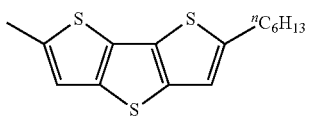
L2ex1-19 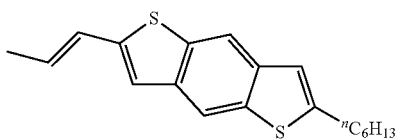
L2ex1-20 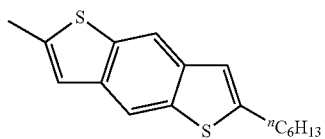
L2ex1-21 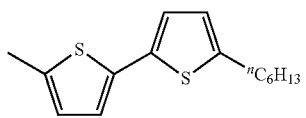

-continued
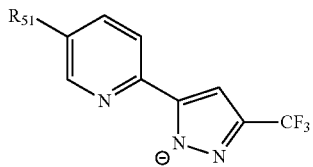
| | $R_{51}$ |
|---|---|
| L2ex2-1 | 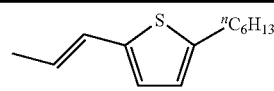 |
| L2ex2-2 | 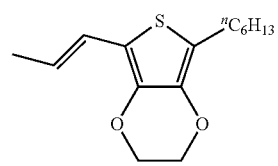 |
| L2ex2-3 | 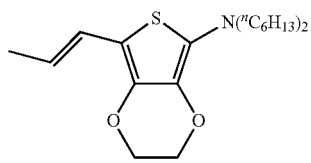 |
| L2ex2-4 | 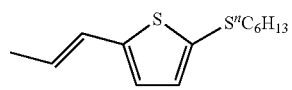 |
| L2ex2-5 | 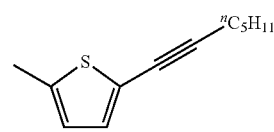 |
| L2ex2-6 | 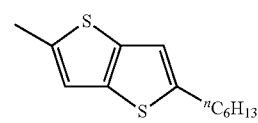 |
| L2ex2-7 | 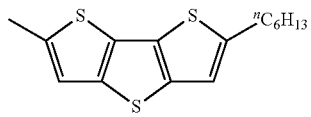 |
| L2ex2-8 | 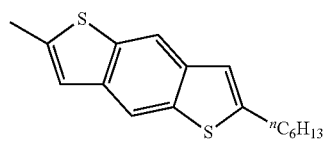 |
| L2ex2-9 | 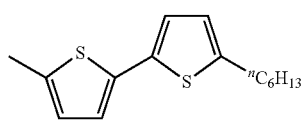 |
| L2ex2-10 | 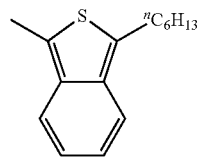 |

-continued
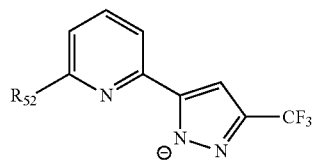
| | $R_{52}$ |
|---|---|
| L2ex3-1 | 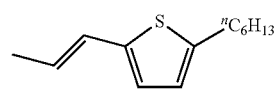 |
| L2ex3-2 | 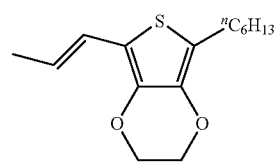 |
| L2ex3-3 | 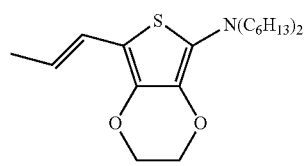 |
| L2ex3-4 | 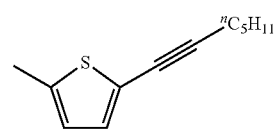 |
| L2ex3-5 | 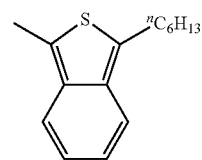 |
| L2ex3-6 | 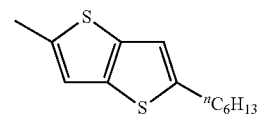 |
| L2ex3-7 | 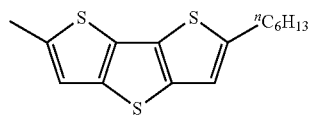 |
| L2ex3-8 | 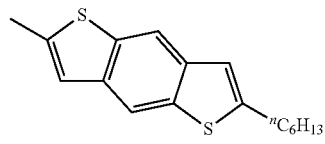 |
| L2ex3-9 | 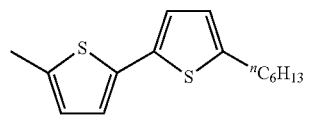 |

-continued
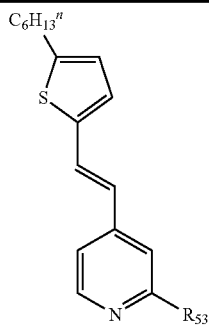
| | $R_{53}$ |
|---|---|
| L2ex4-1 | 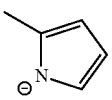 |
| L2ex4-2 | 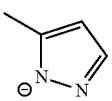 |
| L2ex4-3 | 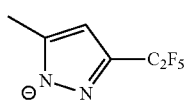 |
| L2ex4-4 | 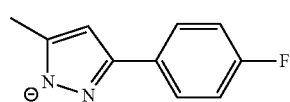 |
| L2ex4-5 | 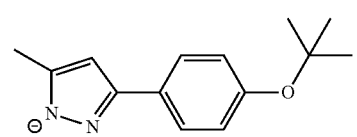 |
| L2ex4-6 | 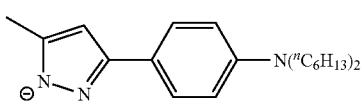 |
| L2ex4-7 | 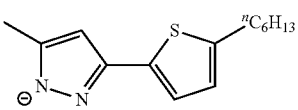 |
| L2ex4-8 | 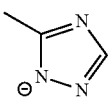 |
| L2ex4-9 | 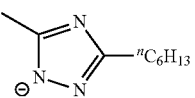 |
| L2ex4-10 | 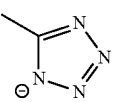 |
| L2ex4-11 | 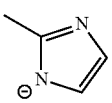 |

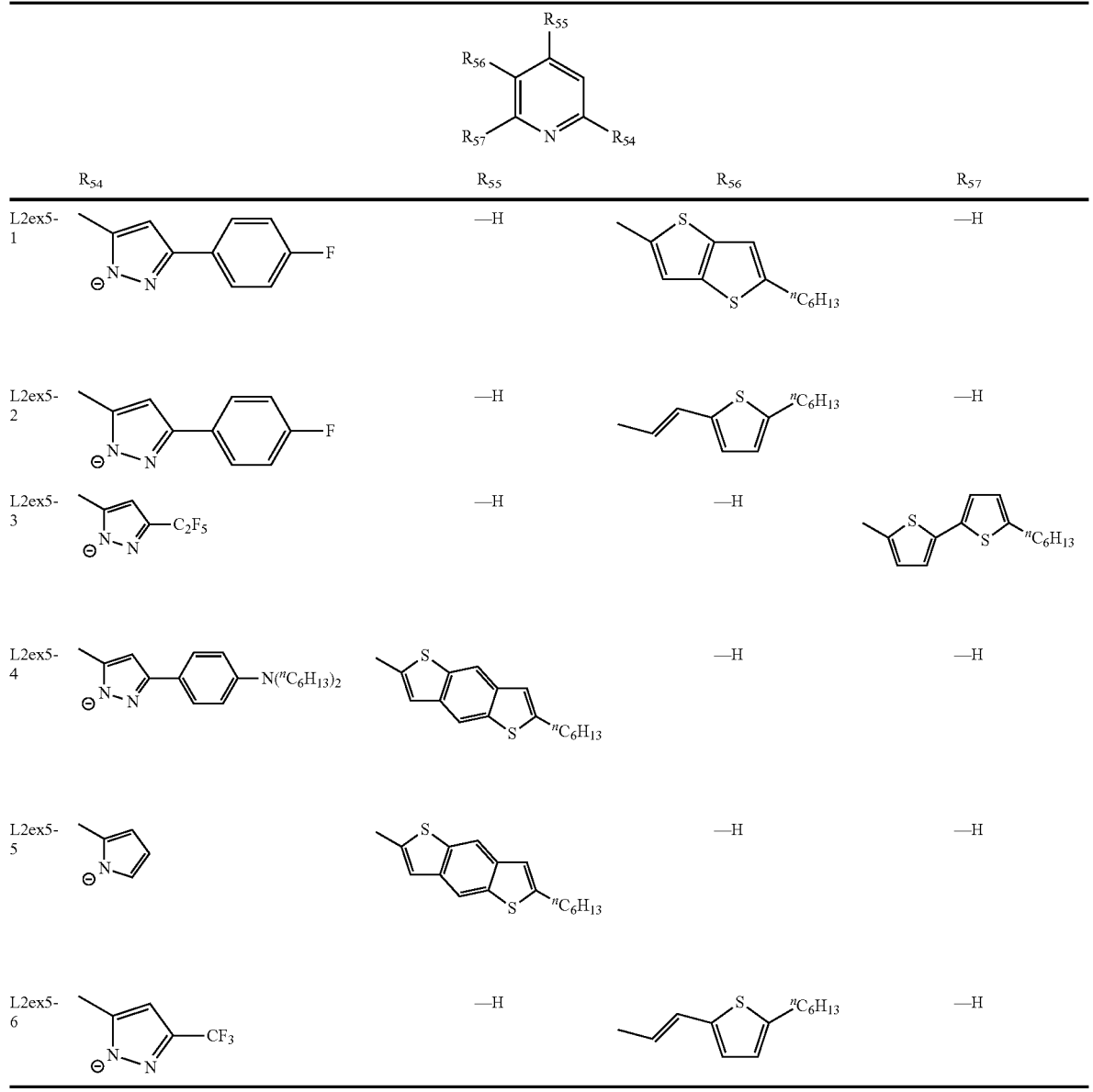

<Ligand $Z^1$>

$Z^1$ represents a monodentate ligand. $Z^1$ is, for example, a monodentate ligand that coordinates at a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, a thiocyanate group, an isothiocyanate group, a cyanate group, isocyanate group, a selenate group, an isoselenate group, an isoselenocyanate group, a cyano group, an alkylthio group, an arylthio group, an alkoxy group and an aryloxy group, or a monodentate ligand selected from the group consisting of a halogen atom, a phosphine ligand, carbonyl, a dialkylketone, a carbonamide, a thiocarbonamide and a thiourea. $Z^1$ is preferably an isothiocyanate group, an isoselenocyanate group, an isocyanate group, a halogen atom, or a cyano group. In a case where the ligand $Z^1$ contains an alkyl site, an alkenyl site, an alkynyl site, an alkylene site or the like, these may be a straight chain or a branched chain, and these may be substituted or unsubstituted. Further, in a case where the ligand $Z^1$ contains an aryl site, a hetero ring site, a cycloalkyl site or the like, these may be substituted or unsubstituted, and may be a single ring or a condensed ring.

Hereinafter, specific examples of the metal complex dye of the present invention represented by formula (1) are shown, but the present invention is not limited thereto.

The ligand is shown by the state coordinating to the metal atom, that is to say, the atom coordinating in the form of an anion is shown as the anion. However, the ligand is not always necessary to coordinate in the form of anion.

Further, the metal complex dye is shown omitting a counter ion. However, it does not mean that the metal complex dye does not require the counter ion, but that the metal complex dye may possess an arbitrary counter ion. Examples of the counter ion include the CI in formula (2) described later.

TABLE A

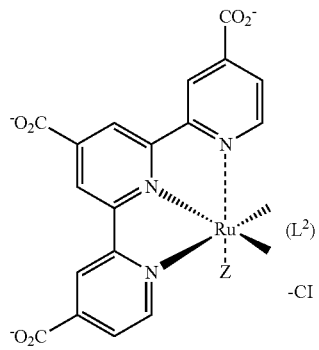

| | L² | Z | CI |
|---|---|---|---|
| D-1-1a | L2ex1-1 | Zex7 | (H⁺)₃ |
| D-1-1b | L2ex1-1 | Zex7 | (H⁺)₂(N⁺Bu₄) |
| D-1-1c | L2ex1-1 | Zex7 | (H⁺)(N⁺Bu₄)₂ |
| D-1-1d | L2ex1-1 | Zex7 | (N⁺Bu₄)₃ |
| D-1-1e | L2ex1-1 | Zex7 | (H⁺)₂(Na⁺) |
| D-1-1f | L2ex1-1 | Zex7 | (N⁺BnEt₃)(H⁺)₂ |
| D-1-1g | L2ex1-1 | Zex7 | (P⁺Bu₄)(H⁺)₂ |
| D-1-1h | L2ex1-1 | Zex7 | (N⁺BnEt₃)(H⁺)₂ |
| D-1-1i | L2ex1-1 | Zex7 | (N⁺HBu₃)(H⁺)₂ |
| D-1-1j | L2ex1-1 | Zex7 | (H⁺)₂(N⁺Bu₄) |
| D-1-1k | L2ex1-1 | Zex7 | (H⁺)₂(N⁺Bu₄) |
| D-1-2a | L2ex1-2 | Zex7 | (H⁺)₃ |
| D-1-2b | L2ex1-2 | Zex7 | (H⁺)₂(N⁺Bu₄) |
| D-1-2c | L2ex1-2 | Zex7 | (H⁺)(N⁺Bu₄)₂ |
| D-1-2d | L2ex1-2 | Zex7 | (N⁺Bu₄)₃ |
| D-1-3a | L2ex1-3 | Zex7 | (H⁺)₂ |
| D-1-4a | L2ex1-4 | Zex7 | (H⁺)(N⁺Bu₄) |
| D-1-5a | L2ex1-5 | Zex7 | (H⁺)₃ |
| D-1-5b | L2ex1-5 | Zex7 | (H⁺)₂(N⁺Bu₄) |
| D-1-5c | L2ex1-5 | Zex7 | (H⁺)(N⁺Bu₄)₂ |
| D-1-5d | L2ex1-5 | Zex7 | (N⁺Bu₄)₃ |
| D-1-6a | L2ex1-6 | Zex7 | (H⁺)₃ |
| D-1-6b | L2ex1-6 | Zex7 | (H⁺)₂(N⁺Bu₄) |
| D-1-6c | L2ex1-6 | Zex7 | (H⁺)(N⁺Bu₄)₂ |
| D-1-6d | L2ex1-6 | Zex7 | (N⁺Bu₄)₃ |
| D-1-7a | L2ex1-8 | Zex7 | (H⁺)₃ |
| D-1-7b | L2ex1-8 | Zex7 | (H⁺)₂(N⁺Bu₄) |
| D-1-7c | L2ex1-8 | Zex7 | (H⁺)(N⁺Bu₄)₂ |
| D-1-7d | L2ex1-8 | Zex7 | (N⁺Bu₄)₃ |
| D-1-8a | L2ex1-9 | Zex7 | (H⁺)₃ |
| D-1-8b | L2ex1-9 | Zex7 | (H⁺)₂(N⁺Bu₄) |
| D-1-8c | L2ex1-9 | Zex7 | (H⁺)(N⁺Bu₄)₂ |
| D-1-8d | L2ex1-9 | Zex7 | (N⁺Bu₄)₃ |
| D-1-9a | L2ex1-11 | Zex7 | (H⁺)₃ |
| D-1-9b | L2ex1-11 | Zex7 | (H⁺)₂(N⁺Bu₄) |
| D-1-9c | L2ex1-11 | Zex7 | (H⁺)(N⁺Bu₄)₂ |
| D-1-9d | L2ex1-11 | Zex7 | (N⁺Bu₄)₃ |
| D-1-10a | L2ex1-12 | Zex7 | (H⁺)₃ |
| D-1-10b | L2ex1-12 | Zex7 | (H⁺)₂(N⁺Bu₄) |
| D-1-10c | L2ex1-12 | Zex7 | (H⁺)(N⁺Bu₄)₂ |
| D-1-10d | L2ex1-12 | Zex7 | (N⁺Bu₄)₃ |
| D-1-11a | L2ex1-13 | Zex7 | (H⁺)₃ |
| D-1-11b | L2ex1-13 | Zex7 | (H⁺)₂(N⁺Bu₄) |
| D-1-11c | L2ex1-13 | Zex7 | (H⁺)(N⁺Bu₄)₂ |
| D-1-11d | L2ex1-13 | Zex7 | (N⁺Bu₄)₃ |
| D-1-12a | L2ex1-16 | Zex7 | (H⁺)₃ |
| D-1-12b | L2ex1-16 | Zex7 | (H⁺)₂(N⁺Bu₄) |
| D-1-12c | L2ex1-16 | Zex7 | (H⁺)(N⁺Bu₄)₂ |
| D-1-12d | L2ex1-16 | Zex7 | (N⁺Bu₄)₃ |
| D-1-13a | L2ex1-18 | Zex7 | (H⁺)₃ |
| D-1-13b | L2ex1-18 | Zex7 | (H⁺)₂(N⁺Bu₄) |
| D-1-13c | L2ex1-18 | Zex7 | (H⁺)(N⁺Bu₄)₂ |
| D-1-13d | L2ex1-18 | Zex7 | (N⁺Bu₄)₃ |
| D-1-14a | L2ex1-20 | Zex7 | (H⁺)₃ |
| D-1-14b | L2ex1-20 | Zex7 | (H⁺)₂(N⁺Bu₄) |
| D-1-14c | L2ex1-20 | Zex7 | (H⁺)(N⁺Bu₄)₂ |
| D-1-14d | L2ex1-20 | Zex7 | (N⁺Bu₄)₃ |
| D-1-15a | L2ex1-21 | Zex7 | (H⁺)₃ |
| D-1-16a | L2ex2-1 | Zex7 | (H⁺)₃ |
| D-1-16b | L2ex2-1 | Zex7 | (H⁺)₂(N⁺Bu₄) |
| D-1-16c | L2ex2-1 | Zex7 | (H⁺)(N⁺Bu₄)₂ |
| D-1-16d | L2ex2-1 | Zex7 | (N⁺Bu₄)₃ |
| D-1-17a | L2ex2-6 | Zex7 | (H⁺)₃ |
| D-1-18a | L2ex3-1 | Zex7 | (H⁺)₃ |
| D-1-19a | L2ex4-1 | Zex7 | (H⁺)₃ |
| D-1-20a | L2ex4-2 | Zex7 | (H⁺)₃ |
| D-1-21a | L2ex4-3 | Zex7 | (H⁺)₃ |
| D-1-22a | L2ex4-6 | Zex7 | (H⁺)₃ |
| D-1-23a | L2ex4-7 | Zex7 | (H⁺)₃ |
| D-1-23b | L2ex4-7 | Zex7 | (H⁺)₂(N⁺Bu₄) |
| D-1-23c | L2ex4-7 | Zex7 | (H⁺)(N⁺Bu₄)₂ |
| D-1-23d | L2ex4-7 | Zex7 | (N⁺Bu₄)₃ |
| D-1-24a | L2ex4-8 | Zex7 | (H⁺)₃ |
| D-1-25a | L2ex4-10 | Zex7 | (H⁺)₃ |
| D-1-26a | L2ex4-11 | Zex7 | (H⁺)₃ |
| D-1-26b | L2ex4-11 | Zex7 | (H⁺)₂(N⁺Bu₄) |
| D-1-26c | L2ex4-11 | Zex7 | (H⁺)(N⁺Bu₄)₂ |
| D-1-26d | L2ex4-11 | Zex7 | (N⁺Bu₄)₃ |
| D-1-27a | L2ex4-4 | Zex7 | (H⁺)₃ |
| D-1-27b | L2ex4-4 | Zex7 | (H⁺)₂(N⁺Bu₄) |
| D-1-27c | L2ex4-4 | Zex7 | (H⁺)(N⁺Bu₄)₂ |
| D-1-27d | L2ex4-4 | Zex7 | (N⁺Bu₄)₃ |
| D-1-28a | L2ex1-1 | Zex1 | (H⁺)₃ |
| D-1-29a | L2ex1-1 | Zex8 | (H⁺)₃ |
| D-1-30a | L2ex1-1 | Zex9 | (H⁺)₃ |
| D-1-31a | L2ex1-1 | Zex3 | (H⁺)₃ |
| D-1-32a | L2ex1-1 | Zex5 | (H⁺)₃ |
| D-1-33a | L2ex1-1 | Zex10 | (H⁺)₃ |
| D-1-34a | L2ex1-1 | Zex4 | (H⁺)₃ |
| D-1-35a | L2ex4-1 | Zex7 | (H⁺)₃ |
| D-1-36a | L2ex4-9 | Zex7 | (H⁺)₃ |
| D-1-37a | L2ex4-10 | Zex7 | (H⁺)₃ |

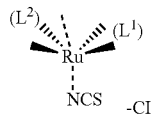

| | L¹ | L² | CI |
|---|---|---|---|
| D-2-1a | Bex5 | L2ex1-1 | (H⁺)₃ |
| D-2-1b | Bex5 | L2ex1-1 | (H⁺)₂(N⁺Bu₄) |
| D-2-1c | Bex5 | L2ex1-1 | (H⁺)(N⁺Bu₄)₂ |
| D-2-1d | Bex5 | L2ex1-1 | (N⁺Bu₄)₃ |
| D-2-2a | Bex1 | L2ex1-8 | (H⁺)₃ |
| D-2-3a | Bex3 | L2ex1-15 | (H⁺)₃ |
| D-2-4a | Bex4 | L2ex1-20 | (H⁺)₃ |
| D-2-6a | Bex3 | L2ex3-9 | (H⁺)₃ |
| D-2-7a | Bex6 | L2ex1-21 | (H⁺)₃ |

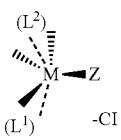

| | L¹ | L² | Z | M | CI |
|---|---|---|---|---|---|
| D-3-1a | Bex2 | L2ex1-1 | Zex7 | Os | (H⁺)₃ |
| D-3-1b | Bex2 | L2ex1-1 | Zex7 | Os | (H⁺)₂(N⁺Bu₄) |
| D-3-1c | Bex2 | L2ex1-1 | Zex7 | Os | (H⁺)(N⁺Bu₄)₂ |
| D-3-1d | Bex2 | L2ex1-1 | Zex7 | Os | (N⁺Bu₄)₃ |
| D-3-2a | Bex3 | L2ex1-1 | Zex10 | Ir | (H⁺)₃ |
| D-3-3a | Bex2 | L2ex1-16 | Zex3 | Rh | (H⁺)₃ |
| D-3-4a | Bex4 | L2ex1-18 | Zex9 | Co | (H⁺)₃ |
| D-3-5a | Bex2 | L2ex1-1 | Zex2 | Ru | (H⁺)₃ |
| D-3-6a | Bex2 | L2ex1-1 | Zex6 | Ru | (H⁺)₂ |

Zex1: —NCSe

Zex2: 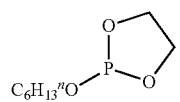

Zex3: —Cl
Zex4: —Br

TABLE A-continued

| | |
|---|---|
| Zex5: | —I |
| Zex6: | 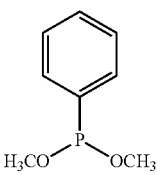 |
| Zex7: | NCS |
| Zex8: | —NCO |
| Zex9: | —SCN |
| Zex10: | —CN |
| Bex-1: | 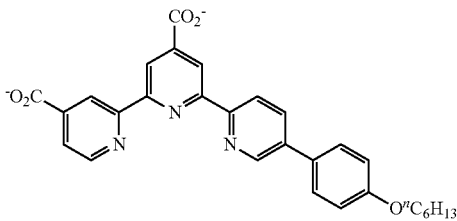 |
| Bex-2: | 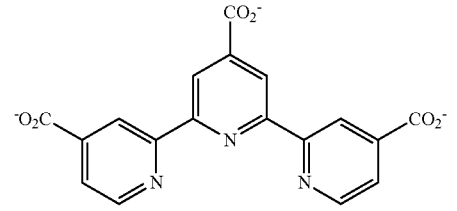 |
| Bex-3: | 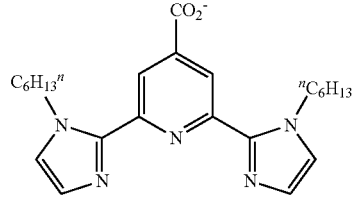 |
| Bex-4: | 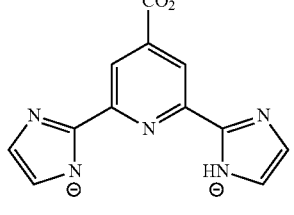 |
| Bex-5: | 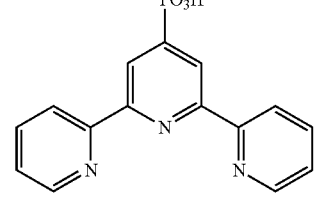 |
| Bex-6: | 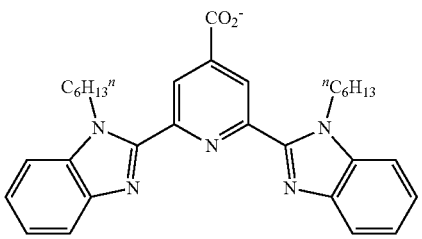 |

When the metal complex dye of the present invention is used for the photoelectric conversion element described later, the metal complex dye may be used alone or in combination with other dyes. Among these dyes, at least one dye (a dye which is other than the metal complex dye represented by formula (1) of the present invention and which is used in combination therewith) has the maximum absorption wavelength in the longest wavelength side of preferably 590 nm or more, and more preferably 600 nm or more, in 0.34 mmol/L tetrabutylammonium hydroxide methanol solution.

Sunlight can be efficiently photoelectrically converted, by combination with a dye that efficiently photoelectrically converts light on a longer wavelength side as compared with the metal complex dye represented by formula (1) according to the present invention. The dye to be combined is preferably a porphyrin dye, a squarylium dye or a phthalocyanine dye; further preferably a porphyrin dye or a squarylium dye; and particularly preferably a squarylium dye. Among the porphyrin dyes, a binuclear complex is preferable. Among the squarylium dyes, a bissquarylium having two squarylium skeletons is preferable.

(Metal Complex Dye Represented by Formula (2))

By using dyes other than the above-described dyes, in combination with the metal complex dye adsorption state of these dyes may be mutually controlled and, photoelectric conversion efficiency and durability which are higher than a single use of each of them can be achieved.

As for the other metal complex dye, a metal complex dye represented by the following formula (2) is preferred.

$$MzL^3{}_{m3}L^4{}_{m4}Y_{mY} \cdot Cl \qquad (2)$$

Metal Atom Mz

Mz has the same meaning as that of $M^1$ in formula (1).

$L^3$ (formula (L3))

$L^3$ represents a bidentate ligand represented by the following formula (L3).

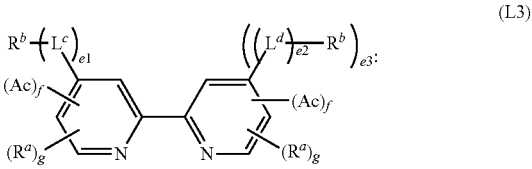

m3 m3 represents an integer of 0 to 3, preferably 1 to 3, and more preferably 1. When m3 is 2 or more, plural $L^3$'s are the same or different from each other.

Ac

Ac represents an acidic group. In a case where plural Ac's exist, they may be the same or different from each other. Ac has the same meaning as defined in formula (1), and the preferable range thereof is also the same as that of formula (1). Ac may substitute an arbitrary atom on a pyridine ring or on a substituent thereof.

$R^a$ $R^a$ represents a substituent. In a case where plural $R^a$'s exist, they may be the same or different from each other.

As the substituent of $R^a$, the substituent T described later can be mentioned. $R^a$ is preferably an alkyl group, an alkenyl group, a cycloalkyl group, an aryl group, a heterocyclic group, an alkoxy group, an aryloxy group, an alkoxycarbonyl group, an amino group, an acyl group, a sulfonamide group, an acyloxy group, a carbamoyl group, an acylamino group, a cyano group, or a halogen atom; more preferably an alkyl group, an alkenyl group, an aryl group, a heterocyclic group, an alkoxy group, an alkoxycarbonyl group, an amino group, an acylamino group, or a halogen atom; and particularly preferably an alkyl group, an alkenyl group, an alkoxy group, an alkoxycarbonyl group, an amino group, or an acylamino group.

$R^b$ $R^b$ represents an alkyl group or an aromatic group. The aromatic group is preferably an aromatic group having 6 to 30 carbon atoms, for example, phenyl, a substituted phenyl group, naphthyl, or a substituted naphthyl group. The heterocyclic group is preferably a heterocyclic group having 1 to 30 carbon atoms, for example, a 2-thienyl group, a 2-pyrrolyl group, a 2-imidazolyl group, a 1-imidazolyl group, a 4-pyridyl group, a 3-indolyl group, or a condensed or linked group obtained by combining two or more of these. A heterocyclic group having 1 to 3 electron donative groups is more preferable, and further preferably a thienyl or a group formed by condensing or linking two or more thienyls.

Herein, the electron donative group is preferably an alkyl group, an alkenyl group, an alkynyl group, a cycloalkyl group, an alkoxy group, an aryloxy group, an amino group, an acylamino group, or a hydroxyl group; more preferably an alkyl group, an alkoxy group, an amino group, or a hydroxyl group; and particularly preferably an alkyl group.

e1 and e2 e1 and e2 are each independently an integer of 0 to 5, preferably an integer of 0 to 3, more preferably an integer of 0 to 2.

$L^c$ and $L^d$

Each of $L^c$ and $L^d$ independently represents a conjugated chain, and examples thereof include a conjugated chain including at least one of the group consisting of an arylene group, a heteroarylene group, an ethenylene group and an ethynylene group. The conjugated chain (an arylene group or a heteroarylene group) may be unsubstituted or may have a substituent. In the case where the ethenylene group has a substituent, the substituent is preferably an alkyl group, and more preferably a methyl group. Preferably $L^c$ and $L^d$ each independently stand for a conjugated chain having 2 to 6 carbon atoms, more preferably thiophenediyl, ethenylene, butadienylene, ethynylene, butadiynylene, methylethenylene, or dimethylethenylene; especially preferably ethenylene or a butadienylene; and most preferably ethenylene. $L^c$ and $L^d$ may be the same or different from each other. However, it is preferable that $L^c$ and $L^d$ are the same. Herein, when the conjugated chain contains a carbon-carbon double bond, each carbon-carbon double bond may have a E configuration or a Z configuration, or a mixture thereof.

e3 e3 represents 0 or 1. Especially, when e3 is 0, f in formula (L3) shown on the right side of the paper is preferably 1 or 2, and similarly when e3 is 1, f shown on the right side of the paper is preferably 0 or 1. The total of f is preferably an integer of 0 to 2.

g represents an integer of 0 to 3, and plural g's may be the same or different from each other. g is preferably an integer of 0 to 2.

f f represents an integer of 0 to 3. Plural f's may be the same or different from each other. When the total of f is one or more and the ligand $L^3$ has at least one acidic group, m3 in formula (2) is preferably 2 or 3, and more preferably 2. When f is 2 or more, plural Ac's may be the same or different from each other. In formula (L3), f shown on the left side of the paper is preferably 0 or 1, and similarly f shown on the right side of the paper is preferably an integer of 0 to 2.

The ligand $L^3$ in formula (2) is preferably a ligand represented by the following formula (L3-1), (L3-2) or (L3-3).

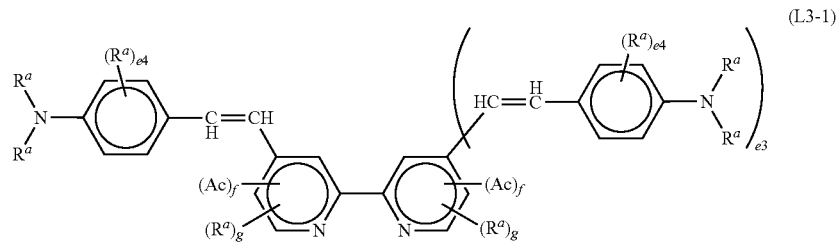

(L3-1)

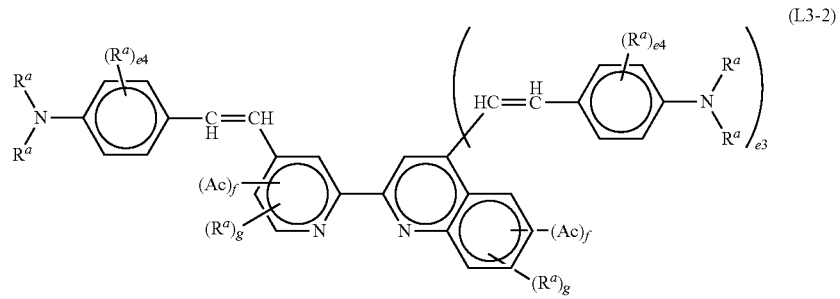

(L3-2)

(L3-3)

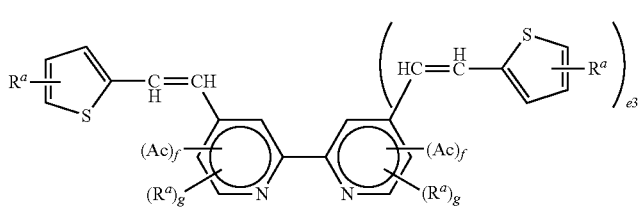

In formulae, Ac, Ra, f, g and e3 have the same meaning of those of the formula (L3), respectively. However, Ra in —N(Ra)(Ra) may be a hydrogen atom. e4 represents an integer of 0 to 4.

$L^4$ (Formula (L4))

$L^4$ represents a bidentate or tridentate ligand represented by the following formula (L4).

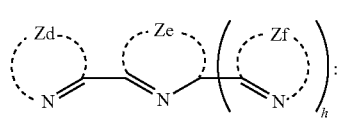
(L4)

In formula (L4), Zd, Ze and Zf represent a group of nonmetallic atoms for forming a 5- or 6-membered ring. h represents 0 or 1. At least one ring formed by Zd, Ze and Zf has an acidic group.

m4 m4 represents an integer of 1 to 3, and preferably 1 or 2. When m4 is 2 or more, plural $L^4$'s may be the same or different from each other.

Zd, Ze and Zf

Zd, Ze and Zf have the same meanings as those of Za, Zb and Zc in formula (1), respectively.

h h represents 0 or 1. h is preferably 0, and $L^4$ is preferably a bidentate ligand.

The ligand $L^4$ is preferably a ligand represented by any one of the following formulae (L4-1) to (L4-8), more preferably a ligand represented by formula (L4-1), (L4-2), (L4-4) or (L4-6), particularly preferably a ligand represented by formula (L4-1) or (L4-2), and particularly preferably a ligand represented by formula (L4-1).

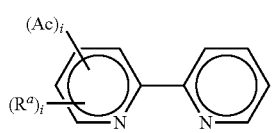
L4-1 (8)

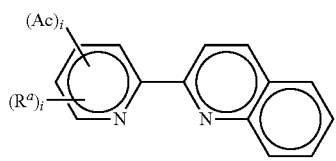
L4-2 (10)

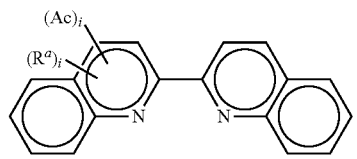
L4-3 (12)

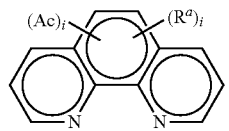
L4-4 (8)

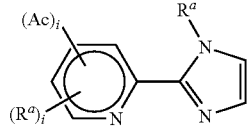
L4-5 (6)

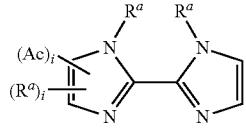
L4-6 (4)

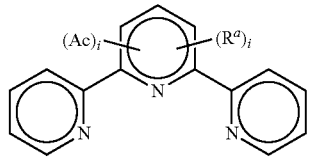
L4-7 (11)

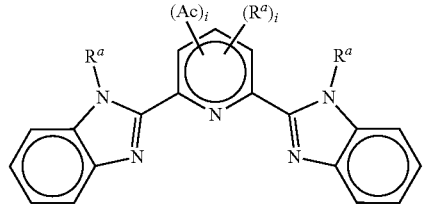
L4-8 (11)

In formulae, Ac represents an acidic group or a salt thereof. Ac is preferably the aforementioned acidic group Ac. In a case where i is two or more, plural Ac's may be the same or different from each other.

In formulae, $R^a$ has the same meaning as that of formula (1). However, $R^a$ which is substituted at N-position (on the nitrogen atom of the above-described imidazole ring) may be a hydrogen atom.

i represents a number (integer) ranging from 0 to the number of position of carbon which may possibly have a substituent. Plural is may be the same or different from each other.

The number of possible substituents is shown in parenthesis lateral to the formula number. When plural $R^e$'s exist, they may be linked or condensed to form a ring.

It is noted that although each of the substituents $R^a$ in the above formulae L4-1 to L4-8 reaches up its atomic bonding for the predetermined aromatic ring, $R^a$ is not limited to the substitution for the predetermined aromatic ring. That is to say, for example, although formula L4-1 shows a configuration in which the pyridine ring on the paper left side is substituted with Ac or $R^a$, the configuration may be such that the pyridine ring on the paper right side may be substituted with the same.

Ligand Y

In formula (2), Y represents a monodentate or bidentate ligand. mY represents the number of the ligand Y. mY is an integer of 0 to 2. mY is preferably 1 or 2. When Y is a monodentate ligand, mY is preferably 2; and when Y is a bidentate ligand, mY is preferably 1. When mY is 2 or more, plural Y's may be the same or different from each other; and the plural Y's may bond together.

The ligand Y is preferably a ligand which coordinates via a group selected from the group consisting of an acyloxy group, a thioacylthio group, an acylaminooxy group, a dithiocarbamate group, a dithiocarbonate group, a trithiocarbonate group, a thiocyanate group, an isothiocyanate group, a cyanate group, an isocyanate group, a cyano group, an alkylthio group, an arylthio group, an alkoxy group, and an aryloxy group, or a ligand composed of a halogen atom, carbonyl, a 1,3-diketone or a thiourea; more preferably a ligand which coordinates via a group selected from the group consisting of an acyloxy group, an acylaminooxy group, a dithiocarbamate group, a thiocyanate group, an isothiocyanate group, a cyanate group, an isocyanate group, a cyano group, and an arylthio group, or a ligand composed of a halogen atom, a 1,3-diketone or a thiourea; especially preferably a ligand which coordinates via a group selected from the group consisting of a dithiocarbamate group, a thiocyanate group, an isothiocyanate group, a cyanate group, and an isocyanate group, or a ligand composed of a halogen atom or a 1,3-diketone; most preferably a ligand which coordinates via a group selected from the group consisting of a dithiocarbamate group, a thiocyanate group, and an isothiocyanate group, or a ligand composed of a 1,3-diketone. In a case where the ligand Y contains an alkyl site, an alkenyl site, an alkynyl site, an alkylene site or the like, these may be a straight chain or a branched chain, and these may be substituted or unsubstituted. Further, in a case where the ligand Y contains an aryl site, a hetero ring site, a cycloalkyl site or the like, these may be substituted or unsubstituted, and may be a single ring or a condensed ring.

In the case where Y is a bidentate ligand, Y is preferably a ligand which coordinates via a group selected from the group consisting of an acyloxy group, an acylthio group, a thioacyloxy group, a thioacylthio group, an acylaminooxy group, a thiocarbamate group, a dithiocarbamate group, a thiocarbonate group, a dithiocarbonate group, a trithiocarbonate group, an acyl group, an alkylthio group, an arylthio group, an alkoxy group, and an aryloxy group, or a ligand composed of a 1,3-diketone, a carbonamide group, a thiocarbonamide group or a thiourea. In the case where Y is a monodentate ligand, Y is preferably a ligand which coordinates via a group selected from the group consisting of a thiocyanate group, an isothiocyanate group, a cyanate group, an isocyanate group, a cyano group, an alkylthio group and an arylthio group, or a ligand composed of a halogen atom, carbonyl, a dialkylketone or a thiourea.

Counter Ion CI

CI in formula (2) represents a counter ion in the case where the counter ion is necessary to neutralize a charge. Generally, whether the dye is cationic or anionic, or has a net ionic charge, depends on the metal, the ligand and the substituent in the dye.

In the case where the substituent has a dissociative group or the like, the dye represented by formula (2) may have a negative charge arising from dissociation. In this case, an electric charge of the dye represented by formula (2) as a whole is electrically neutralized by the counter ion CI.

When the counter ion CI is a positive counter ion, examples of the counter ion CI include an inorganic or organic ammonium ion (for example, tetraalkyl ammonium ion, pyridinium ion and the like), an alkali metal ion and a proton.

When the counter ion CI is a negative counter ion, for example, the negative counter ion may be an inorganic negative ion or an organic negative ion. Examples thereof include a halogen negative ion (for example, fluoride ion, chloride ion, bromide ion, iodide ion and the like), a substituted arylsulfonate ion (for example, p-toluene sulfonate ion, p-chlorobenzene sulfonate ion and the like), an aryldisulfonate ion (for example, 1,3-benzene disulfonate ion, 1,5-naphthalene disulfonate ion, 2,6-naphthalene disulfonate ion and the like), an alkylsulfate ion (for example, methylsulfate ion and the like), a sulfate ion, a thiocyanate ion, a perchlorate ion, a tetrafluoroborate ion, a hexafluorophosphate ion, a picrate ion, an acetate ion and a trifluoromethane sulfonate ion. Alternatively, as a charge balance counter ion, an ionic polymer or another dye with the opposite charge from the primary dye may be used. Alternatively, a metal complex ion (for example, bisbenzene-1,2-dithiolatonickel (III) and the like) may be used.

Interlocking Group

The metal complex dye represented by formula (2) preferably has at least one or more interlocking groups which bind to or adsorb on the surface of semiconductor particles. The metal complex dye preferably has from 1 to 6 interlocking groups, and particularly preferably from 1 to 4 interlocking groups. As the interlocking group, the aforementioned Ac can be mentioned.

Hereinafter, specific examples of the metal complex dye represented by formula (2), which is preferably used in the present invention, are shown, but the present invention is not limited thereto.

In the case where a dye in the following specific examples contains a ligand having a proton-dissociable group, the ligand may release a proton ($H^+$) with dissociation as needed. In the present invention, these embodiments are also included.

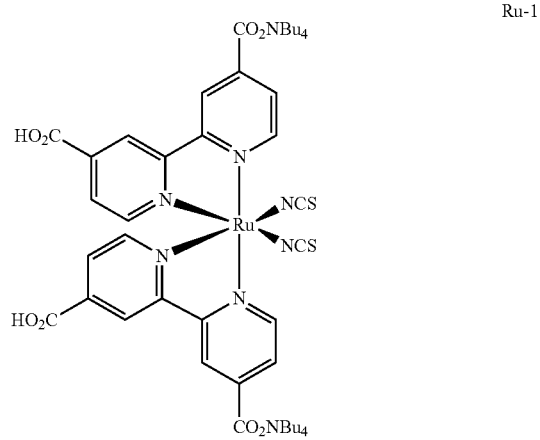

Ru-1

-continued
Ru-2
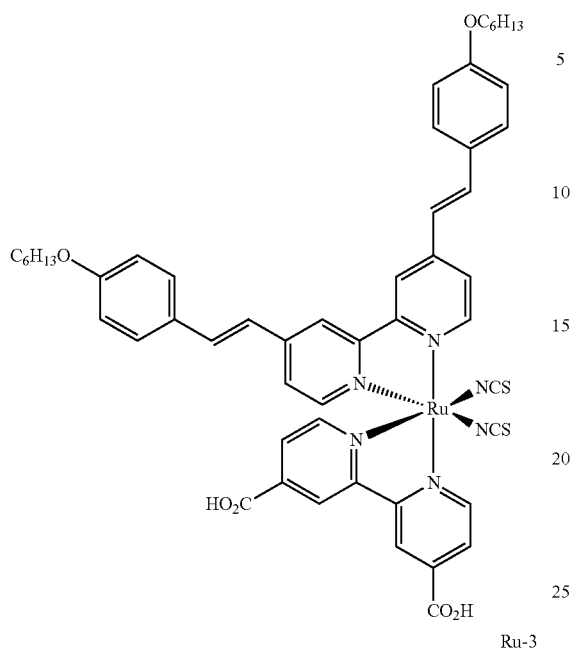
Ru-3
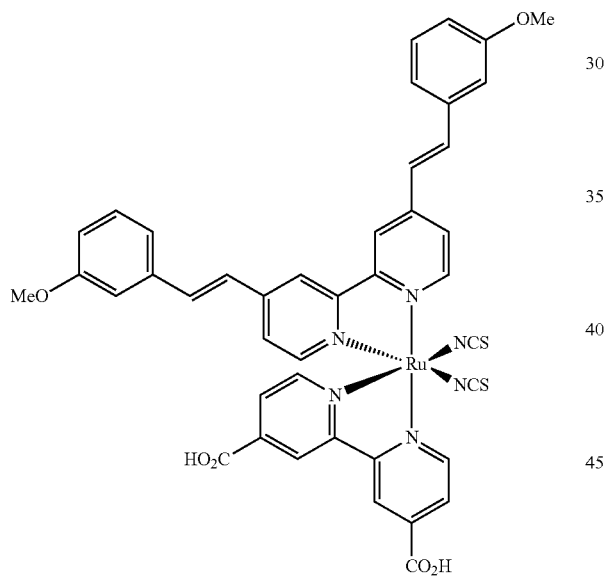
Ru-4
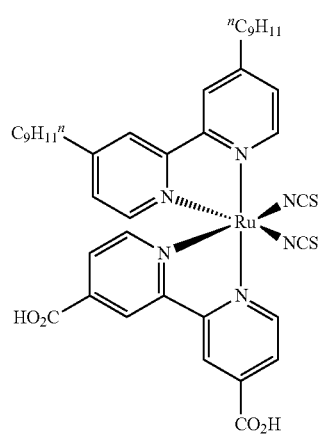
-continued
Ru-5
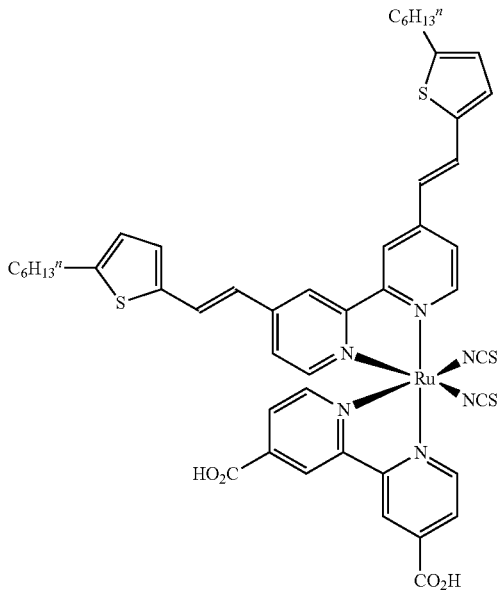
Ru-6
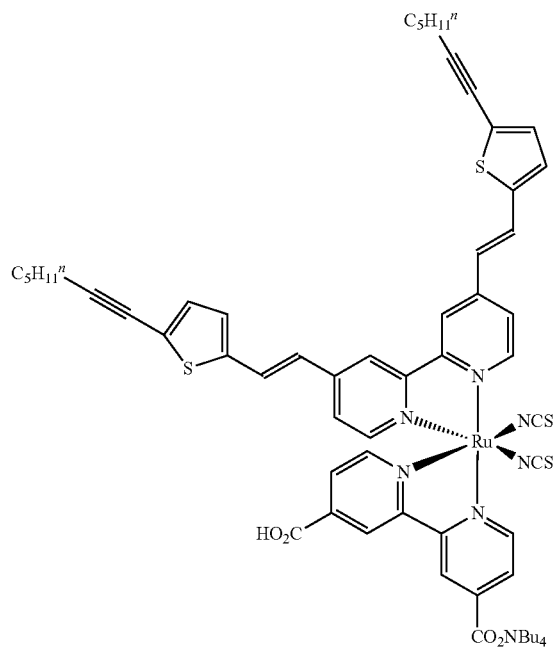

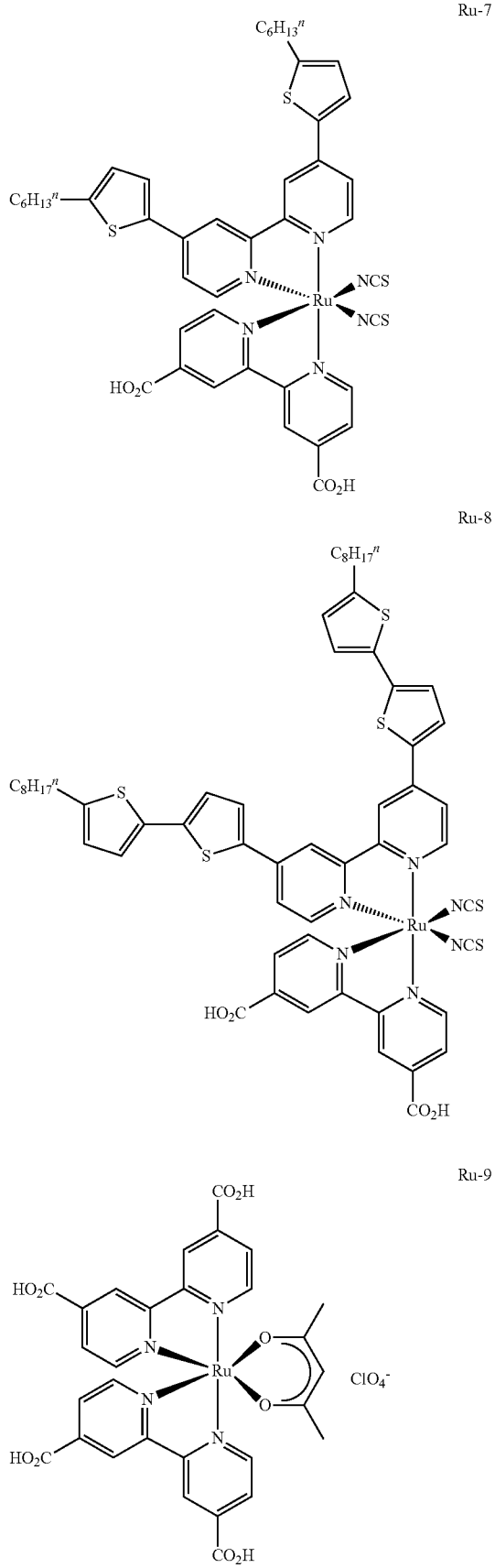

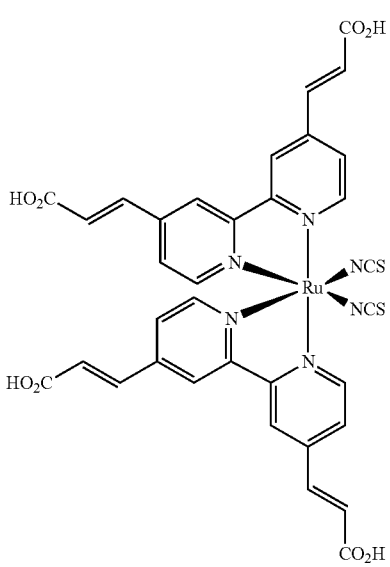

The metal complex dye represented by the above-described formula (2) can be easily synthesized with reference to a method described in JP-A-2001-291534 ("JP-A" means unexamined published Japanese patent application) and a method that is cited in the above Japanese patent publication, or in accordance with these methods.

The metal complex dye represented by formula (2) has a maximum absorption wavelength in a solution in a range of preferably from 300 nm to 1,000 nm, more preferably from 350 nm to 950 nm, and especially still more preferably from 370 nm to 900 nm.

In the photoelectric conversion element and the photoelectrochemical cell of the present invention, high conversion efficiency can be secured, through use of light of a wide range of wavelengths by means of at least the metal complex dye represented by formula (1) and the metal complex dye represented by formula (2) in combination.

As for the combination ratio of the metal complex dye represented by formula (2) and the metal complex dye represented by formula (1), provided that the former is designated as R while the latter as S, R/S in terms of mole % ratio is from 95/5 to 10/90, preferably from 95/5 to 50/50, more preferably from 95/5 to 60/40, still more preferably from 95/5 to 65/35, and most preferably from 95/5 to 70/30.

[Co-Adsorbent]

In the photoelectric conversion element of the present invention, a co-adsorbent is preferably used for the metal complex dye of the present invention or for the dye used in combination therewith. As such a co-adsorbent, a co-adsorbent having a carboxyl group or a salt thereof is preferable, and examples of the co-adsorbent include a fatty acid and a compound having a steroid skeleton. The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is further preferable.

A preferred co-adsorbent is a compound represented by the following formula (3).

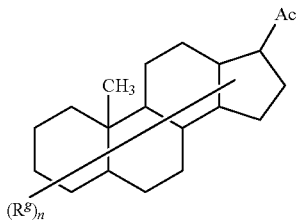

(3)

In formula (3), R$^g$ represents a substituent. As the substituent, the substituent T described later can be mentioned.

Ac represents an acidic group and has the same meaning as that of Ac in formula (1). Ac is preferably an alkyl group having an acidic group.

n represents an integer of 0 or more. When n is an integer of 2 or more, plural R$^g$'s may be the same or different from each other. n is preferably an integer of 2 to 4.

As specific examples of the above compound, can be mentioned are compounds mentioned as the examples of the above-mentioned compound having a steroid skeleton.

The co-adsorbent that can be used in the present invention exerts, by adsorbing on the semiconductor fine particles, an effect of suppressing the inefficient association of the dye and an effected of preventing reverse electron migration from the semiconductor fine-particle surface to the redox system in the electrolyte. The use amount of the co-adsorbent is not particularly limited. However, from the viewpoints of effectively producing the above actions, it is preferred that the amount thereof is preferably from 1 to 200 mole, more preferably from 10 to 150 mole, and particularly preferably from 20 to 50 mole, with respect to 1 mole of the above-described dye.

<Substituent T>

The specification uses an expression "compound" (including complex and dye) to mean, in addition to the compound itself, its salts, its complex and its ion. Further, the expression means to include its derivatives in which a predetermined portion of the compound has been modified in the range such that a desired effect is produced. Further, a substituent with which substitution or non-substitution is not explicitly described in the present specification means that the substituent may have an arbitrary substituent (same applies to a linking group and a ligand). The same is true on a compound with which substitution or non-substitution is not explicitly described. Preferable examples of the substituent include the following substituent T.

In the present specification, the simple description only as a "substituent" means to reference the substituent T. Further, in a case where each of the substituents, for example, like an alkyl group, is described in a simplistic form, both a preferable range and specific examples for the corresponding group of the substituent T are applied.

The substituent T includes the followings:
an alkyl group (preferably an alkyl group having 1 to 20 carbon atoms, e.g. methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, butadiynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an cycloalkenyl group (preferably a cycloalkenyl group having 5 to 20 carbon atoms, e.g. cyclopentenyl, or cyclohexenyl), an aryl group (preferably an aryl group having 6 to 26 carbon atoms, e.g. phenyl, 1-naphthyl, 4-methoxyphenyl, 2-chlorophenyl, or 3-methylphenyl), a heterocyclic group (preferably a 5- or 6-membered heterocyclic group having 2 to 20 carbon atoms and at least one oxygen atom, sulfur atom, or nitrogen atom, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an alkenyloxy group (preferably an alkenyloxy group having 2 to 20 carbon atoms, e.g. vinyloxy or allyloxy), an alkynyloxy group (preferably an alkynyloxy group having 2 to 20 carbon atoms, e.g. 2-propenyloxy or 4-butynyloxy), a cycloalkyloxy group (preferably a cycloalkyl group having 3 to 20 carbon atoms, e.g. cyclopropyloxy, cyclopentyloxy, cyclohexyloxy, or 4-methylcyclohexyloxy), an aryloxy group (preferably an aryloxy group having 6 to 26 carbon atoms, e.g. phenoxy, 1-naphthyloxy, 3-methylphenoxy, or 4-methoxyphenoxy), a heterocyclic oxy group (e.g. imidazolyloxy, benzoimidazolyloxy, thiazolyloxy, benzothiazolyloxy, triazinyloxy, or purinyloxy);

an alkoxycarbonyl group (preferably an alkoxycarbonyl group having 2 to 20 carbon atoms, e.g. ethoxycarbonyl, or 2-ethylhexyloxycarbonyl), a cycloalkoxycarbonyl group (preferably a cycloalkoxycarbonyl group having 4 to 20 carbon atoms, e.g. cyclopropyloxycarbonyl, cyclopentyloxycarbonyl, or cyclohexyloxycarbonyl), an aryloxycarbonyl group (preferably an aryloxycarbonyl group having 6 to 20 carbon atoms, e.g. phenyloxycarbonyl, or naphthyloxycarbonyl), an amino group (preferably an amino group having 0 to 20 carbon atoms including an alkylamino group, an alkenylamino group, an alkynylamino group, a cycloalkylamino group, a cycloalkenylamino group, an arylamino group, and a heterocyclic amino group, e.g. amino, N,N-dimethylamino, N,N-diethylamino, N-ethylamino, N-allylamino, N-(2-propinyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably a sulfamoyl group having 0 to 20 carbon atoms, preferably an alkyl-, cycloalkyl-, or aryl-sulfamoyl group, e.g. N,N-dimethylsulfamoyl, N-cyclohexylsulfamoyl, or N-phenylsulfamoyl), an acyl group (preferably an acyl group having 1 to 20 carbon atoms, e.g. acetyl, cyclohexylcarbonyl, or benzoyl), an acyloxy group (preferably an acyloxy group having 1 to 20 carbon atoms, e.g. acetyloxy, cyclohexylcarbonyloxy, or benzoyloxy), a carbamoyl group (preferably a carbamoyl group having 1 to 20 carbon atoms, preferably an alkyl-, cycloalkyl-, or aryl-carbamoyl group, e.g. N,N-dimethylcarbamoyl, N-cyclohexylcarbamoyl, or N-phenylcarbamoyl), an acylamino group (preferably an acylamino group having 1 to 20 carbon atoms, e.g. acetylamino, cyclohexylcarbonylamino, or benzoylamino), a sulfonamide group (preferably a sulfonamide group having 0 to 20 carbon atoms, preferably an alkyl-, cycloalkyl-, or aryl-sulfonamide group, e.g. methane sulfonamide, benzene sulfonamide, N-methyl methane sulfonamide, N-cyclohexyl sulfonamide, or N-ethyl benzene sulfonamide), an alkylthio group (preferably an alkylthio group having 1 to 20 carbon atoms, e.g. methylthio, ethylthio, isopropylthio, or benzylthio), a cycloalkylthio group (preferably a cycloalkylthio group having 3 to 20 carbon atoms, e.g. cyclopropylthio, cyclopentylthio, cyclohexylthio, or 4-methylcyclohexylthio), an arylthio group (preferably an arylthio group having 6 to 26 carbon atoms, e.g. phenylthio, 1-naphthylthio, 3-methylphenylthio, or 4-methoxyphenylthio), an alkyl-, cycloalkyl-, or aryl-sulfonyl group (preferably a sulfonyl group having 1 to 20 carbon atoms, e.g. methylsulfonyl, ethylsulfonyl, cyclohexylsulfonyl, or benzene sulfonyl), a silyl group (preferably a silyl group having 1 to 20 carbon atoms, preferably an alkyl-, aryl-, alkoxy-, or aryloxy-substituted silyl group, e.g. triethyl silyl, triphenyl silyl, diethylbenzyl silyl, or dimethylphenyl silyl), a silyloxy group (preferably a silyloxy group having 1 to 20 carbon atoms, preferably an alkyl-, aryl-, alkoxy-, or aryloxy-substituted silyloxy group, e.g. triethyl silyloxy, triphenyl silyloxy, diethylbenzyl silyloxy, or dimethylphenyl silyloxy), a hydroxyl group, a cyano group, a nitro group, a halogen atom (e.g. fluorine, chlorine, bromine, or iodine), a carboxyl group, a sulfo group, a phosphonyl group, a phosphoryl group, and a boric-acid group; more preferably an alkyl group, an alkenyl group, a cycloalkyl group, an aryl group, a heterocyclic group, an alkoxy group, a cycloalkoxy group, an aryloxy group, an alkoxycarbonyl group, cycloalkoxycarbonyl group, the above-described amino group, an acyamino group, a cyano group, or a halogen atom; and particularly preferably an alkyl group, an alkenyl group, a heterocyclic group, an alkoxy group, an alkoxycarbonyl group, an amino group, an acylamino group, or a cyano group.

When the compound or the substituent or the like contains an alkyl group or an alkenyl group, these may be a straight chain or a branched chain, and these may be substituted or unsubstituted. Further, in the case of containing an aryl group, a heterocyclic group or the like, these may be a single ring or a condensed ring, and may be substituted or unsubstituted.

[Photoelectric Conversion Element]
(Photoconductor Layer)

One of preferable embodiments of the photoelectric conversion element according to the present invention has already been explained with reference to FIG. 1. The photoconductor layer 2 in the embodiment is composed of a porous semiconductor layer including a layer of semiconductor fine particles 22 on which the dye of the present invention is adsorbed. Some of the dye may be dissociated in an electrolyte. Further, the photoconductor layer 2 may be designed for any purpose, and may be composed of a multi-layer structure.

As described above, because the photoconductor layer 2 contains semiconductor fine particles 22 on which the specific dye is adsorbed, light-reception sensitivity is highly exerted, and when it is used in the photoelectrochemical cell 100, high photoelectric conversion efficiency can be achieved and further the photoelectrochemical cell has high durability.

(Charge Transfer Layer)

Examples of the redox pair contained in the electrolyte for use in the photoelectric conversion element 10 of the present invention include a combination of iodine and an iodide (for example, lithium iodide, tetrabutylammonium iodide, or tetrapropylammonium iodide), a combination of an alkylviologen (for example, methylviologen chloride, hexylviologen bromide, or benzylviologen tetrafluoroborate) and a reductant thereof, a combination of polyhydroxybenzenes (for example, hydroquinone or naphthohydroquinone) and an oxidant thereof, a combination of a divalent iron complex and a trivalent iron complex (for example, potassium ferricyanide and potassium ferrocyanide), and a combination of a divalent cobalt complex and a trivalent cobalt complex. Among these, a combination of iodine and an iodide is preferred.

In the case where iodine and an iodide are used in combination, as an electrolyte, it is preferred that a 5- or 6-membered-ring nitrogen-containing aromatic cation iodine salt is additionally used in combination with them. Especially, in the case where the compound represented by formula (1) is not an iodine salt, the compound represented by formula (1) is preferably used in combination with an iodine salt of pyridinium salts, imidazolium salts, triazolium salts or the like described in Domestic re-publication of PCT international publication WO95/18456, JP-A-8-259543 and Denki Kagaku (Electrochemistry), Vol. 65, No. 11, page 923 (1997).

The content of iodine in the electrolyte used in the photoelectric conversion element 10 of the present invention is preferably from 0.1 to 20% by mass, and more preferably from 0.5 to 5% by mass, with respect to the total mass of the electrolyte.

The electrolyte used in the photoelectric conversion element 10 of the present invention may contain a solvent. The content of the solvent in the electrolyte is preferably 50% by mass or less, more preferably 30% by mass or less, and particularly preferably 10% by mass or less, with respect to the total mass of the electrolyte.

Further, as the electrolyte in the present invention, use can be made of a charge transportation layer which contains a positive hole-conducting substance. As the positive hole-conducting substance, 9,9'-spirobifluorene derivatives and the like may be used.

Further, an electrode layer, a photoconductor layer (photoelectric conversion layer), a charge transfer layer (hole-transportation layer), a conductive layer, and a counter electrode layer may be laminated sequentially. A hole-transporting material which acts as a p-type semiconductor may be used for the hole-transportation layer. For a preferable hole-transportation layer, an inorganic or organic hole-transporting material may be used. Examples of the inorganic hole-transporting material include CuI, CuO, and NiO. Further, examples of the organic hole-transporting material include macromolecular materials and low-molecular materials. Examples of the macromolecular materials include a polyvinylcarbazole, a polyamine, and an organic polysilane. Further, examples of the low-molecular materials include triphenylamine derivatives, stilbene derivatives, hydrazone derivatives, and phenamine derivatives. Among these, an organic polysilane is preferable because, unlike conventional carbon-based polymers, σ electrons delocalized along Si of the main chain contribute to photoconduction whereby the organic polysilane has a high hole-mobility (Phys. Rev. B, 35, 2818 (1987)).

(Electrically Conductive Support)

As shown in FIG. 1, in the photoelectric conversion element of the present invention, the photoconductor layer 2 in which the dye 21 is adsorbed on the porous semiconductor fine particles 22 has been formed on the electrically conductive support 1. As described later, the photoconductor layer 2 can be produced, for example, by coating a dispersion liquid of semiconductor fine particles on an electrically conductive support and drying, and then soaking it in a solution of the dye of the present invention.

As the electrically conductive support 1, a support having electroconductivity per se, such as a metal, or a glass or polymeric material having an electrically conductive layer on the surface can be used. It is preferable that the electrically conductive support 1 is substantially transparent. The term "substantially transparent" means that the transmittance of light is 10% or more, preferably 50% or more, and particularly preferably 80% or more. As the electrically conductive support 1, a support formed from glass or a polymeric material and coated with an electrically conductive metal oxide can be used. In this case, the amount of coating of the conductive metal oxide is preferably 0.1 to 100 g per square meter of the support made of glass or a polymeric material. In the case of using a transparent electrically conductive support, it is preferable that light is incident from the support side.

Examples of the polymeric material that may be preferably used include triacetylcellulose (TAC), polyethylene terephthalate (PET), polyethylene naphthalate (PEN), syndiotactic polystyrene (SPS), polyphenylene sulfide (PPS), polycarbonate (PC), polyarylate (PAR), polysulfone (PSF), polyester sulfone (PES), polyether imide (PEI), cyclic polyolefin, and phenoxy bromide. The electrically conductive support 1 may be provided with a light management function at the surface, and for example, the anti-reflective film having a high refractive index film and a low refractive index oxide film alternately laminated as described in JP-A-2003-123859, and the light guide function as described in JP-A-2002-260746 may be mentioned.

In addition to the above, a metallic support can also be preferably used. Examples thereof include titanium, aluminum, copper, nickel, iron, stainless steel and copper. These metals may be alloys. Among these, titanium, aluminum and copper are further preferable; and titanium and aluminum are particularly preferable.

(Semiconductor Fine Particle)

As shown in FIG. 1, in the photoelectric conversion element 10 of the present invention, the photoconductor layer 2 in which the dye 21 is adsorbed on the porous semiconductor fine particles 22 is formed on the electrically conductive support 1. The photoconductor layer 2 can be produced through the following method: as described later, for example, a dispersion liquid of semiconductor fine particles 22 is coated on the above-described electrically conductive support 1 and dried, and then the resultant support is soaked in a solution of the above-described dye of the present invention. In the present invention, as the semiconductor fine particles, those prepared using the specific surfactant described above are used.

(Dispersion Liquid of Semiconductor Fine Particles)

In the present invention, a porous semiconductor fine particles-coated layer can be obtained by applying a semiconductor fine particle dispersion liquid in which the content of solids excluding semiconductor fine particles is 10% by mass or less of the total amount of the semiconductor fine particle dispersion liquid, on the electrically conductive support 1 mentioned above, and appropriately heating the coated support.

Examples of the method of producing a semiconductor fine particle dispersion liquid include, in addition to the sol-gel method, a method of precipitating the semiconductor in the form of fine particles in a solvent upon synthesis and directly using the fine particles; a method of ultrasonicating fine particles, and thereby pulverizing the fine particles into ultrafine particles; a method of mechanically grinding a semiconductor using a mill or a mortar, and pulverizing the ground semiconductor; and the like. As a dispersion solvent, one or more solvent selected from water and/or various organic solvents can be used. Examples of the organic solvent include alcohols such as methanol, ethanol, isopropyl alcohol, citronellol and terpineol; ketones such as acetone; esters such as ethyl acetate; dichloromethane, and acetonitrile.

At the time of dispersing the fine particles, for example, a polymer such as polyethylene glycol, hydroxyethyl cellulose or carboxymethylcellulose; a surfactant; an acid; or a chelating agent may be used in a small amount as a dispersing aid, as necessary. It is preferable that such a dispersing aid is mostly eliminated before the step of forming a film on the electrically conductive support, by a filtration method, a method of using a separating membrane, or a centrifugation method. The semiconductor fine particle dispersion liquid is such that the content of solids excluding semiconductor fine particles is 10% by mass or less based on the total amount of the dispersion liquid. This concentration is preferably 5% or less, further preferably 3% or less, further preferably 1% or less, further preferably 0.5% or less, and particularly preferably 0.2% or less. In other words, the semiconductor fine particle dispersion liquid may contain a solvent and solids excluding semiconductor fine particles, in an amount of 10% by mass or less based on the total amount of the semiconductor fine particle dispersion liquid. It is preferable that the semiconductor fine particle dispersion liquid is substantially composed of semiconductor fine particles and a dispersion solvent.

If the viscosity of the semiconductor fine particle dispersion liquid is too high, the dispersion liquid undergoes aggregation, and film formation cannot be achieved. On the other hand, if the viscosity of the semiconductor fine particle dispersion liquid is too low, the liquid flows out, and film formation cannot be achieved in some cases. Therefore, the viscosity of the dispersion liquid is preferably 10 to 300 N·s/m$^2$ at 25° C., and more preferably 50 to 200N·s/m$^2$ at 25° C.

In regard to the method of applying the semiconductor fine particle dispersion liquid, conventional methods such as a roller method, a dipping method or the like can be used as a method involving application. Furthermore, an air knife method, a blade method or the like can be used as a method involving metering.

The thickness of the entire semiconductor fine particle layer is preferably 0.1 µm to 100 µm, more preferably 1 µm to 30 µm, and even more preferably 2 µm to 25 µm. The amount of the coated semiconductor fine particles per square meter of the support is preferably 0.5 g to 400 g, and more preferably 5 g to 100 g. The method of producing a film by coating the above-described semiconductor fine particle dispersion liquid is not particularly limited, and known methods may be applied appropriately.

The use amount of the sensitizing dye 21 in total is preferably from 0.01 mmol to 100 mmol, more preferably from 0.1 mmol to 50 mmol, and particularly preferably from 0.1 mmol to 10 mmol, with respect to 1 m$^2$ of the support. In this case, the use amount of the dye 21 for use in the present invention is preferably adjusted to 5% by mole or more. The amount of the dye 21 adsorbed to the semiconductor fine particles 22 is preferably 0.001 mmol to 1 mmol, and more preferably 0.1 to 0.5 mmol, based on 1 g of the semiconductor fine particles. When the amount of the dye is adjusted to such a range, the sensitization effect for the semiconductor can be sufficiently obtained. On the other hand, if the amount of the dye is too small, the sensitization effect is insufficient, and if the amount of the dye is excessive, the portion of the dye that is not attached to the semiconductor is suspended, and causes a decrease in the sensitization effect.

(Counter Electrode)

The counter electrode 4 is an electrode working as a positive electrode in the photoelectrochemical cell. The counter electrode 4 usually has the same meaning as the electrically conductive support 1 described above, but in a construction which is likely to maintain a sufficient strength, a support of the counter electrode is not necessarily required. However, a construction having a support is advantageous in terms of sealability. Examples of the material for the counter electrode 4 include platinum, carbon, and electrically conductive polymers. Preferred examples include platinum, carbon, and electrically conductive polymers. A preferred structure of the counter electrode 4 is a structure having a high charge collecting effect. Preferred examples thereof include those described in JP-A-10-505192 and the like.

(Light-Receiving Electrode)

The light-receiving electrode 5 may be a tandem type electrode so as to increase the utility ratio of the incident light, or the like. Preferred examples of the tandem type construction include those described in JP-A-2000-90989, JP-A-2002-90989 and the like. The light-receiving electrode 5 may be provided with the photo management function by which light scattering and reflection are efficiently achieved inside the light-receiving electrode layer. Preferred examples thereof include those described in JP-A-2002-93476 and the like.

It is preferable to form a short-circuit preventing layer between the electrically conductive support 1 and the porous semiconductor fine particle layer, so as to prevent reverse current due to a direct contact between the electrolyte and the electrode. Preferred examples thereof include those described in JP-A-06-507999 and the like. It is preferable to employ a spacer or a separator so as to prevent the contact between the light-receiving electrode 5 and the counter electrode 4. Preferred examples thereof include those described in JP-A-2001-283941 and the like.

Methods for sealing a cell or a module preferably include a method using a polyisobutylene thermosetting resin, a novolak resin, a photocuring (meth)acrylate resin, an epoxy resin, an ionomer resin, glass frit, or aluminum alkoxide for alumina; and a method of laser fusing of low-melting point glass paste. When the glass frit is used, a mixture prepared by mixing powder glass with an acrylic resin being a binder may be used.

EXAMPLES

The present invention will be described in more detail based on examples given below, but the invention is not meant to be limited by these.

<Preparation of Dye>

Hereinafter, methods of preparing the dye of the present invention are described in detail on the basis of Examples. However, the starting materials, the dye intermediates and the preparation routes are not limited by these.

(Preparation of Exemplified Dye D-1-1a)

Exemplified dye D-1-1a was prepared according to the method shown in the following scheme.

(i) Preparation of Compound d-1-2

In 200 ml of THF (tetrahydrofurane), 25 g of Compound d-1-1 (2-acetyl-4-methylpyridine) was dissolved, and 18.9 g of sodium ethoxide was added thereto while stirring at 0° C. under a nitrogen atmosphere, and stirred for 15 minutes. After that, 28.9 g of ethyl trifluoroacetate was added drop-wise thereto and stirred for 20 hours at external temperature of 70° C. After the thus-obtained mixture was returned to room temperature, an ammonium chloride aqueous solution was added drop-wise thereto. Then, the organic layer was taken by separation and concentrated, and thus 72.6 g of crude product d-1-2 was obtained.

(ii) Preparation of Compound d-1-3

In 220 ml of ethanol, 72.6 g of the compound d-1-2 was dissolved, and 5.6 ml of hydrazine monohydrate was added thereto while stirring at room temperature under a nitrogen atmosphere, and then heated for 12 hours at external temperature of 90° C. After that, 5 ml of concentrated hydrochloric acid was added thereto and stirred for 1 hour. After concentration, extraction and separation was conducted with 150 ml of sodium bicarbonate water and 150 ml of ethyl acetate, and then the obtained organic layer was concentrated. After recrystallization with acetonitrile, 31.5 g of Compound d-1-3 was obtained.

(iii) Preparation of Compound d-1-5

While stirring 4.1 g of diisopropylamine and 30 ml of tetrahydrofurane at −40° C. under a nitrogen atmosphere, 23.1 ml of a 1.6M n-butyl lithium hexane solution was added drop-wise thereto, and then stirred for 2 hours. After that, 4.0 g of Compound d-1-3 was added thereto and stirred at 0° C. for 80 minutes. Then, a solution containing 3.45 g of compound d-1-4 dissolved in 15 ml of tetrahydrofurane was added drop-wise thereto. After that, the mixture was stirred at 0° C. for 80 minutes, and then stirred at room temperature for 5 hours. Then, an ammonium chloride solution was added thereto, and extraction and separation was conducted with ethyl acetate. Then, the obtained organic layer was concentrated. After purification using a silica gel column chromatography, 5.7 g of compound d-1-5 was obtained.

(iv) Preparation of Compound d-1-6

To 50 mL of toluene, 5.0 g of Compound d-1-5 and 5.9 g of PPTS (pyridinium para-toluenesulfonate) were added, and the resultant mixture was subjected to heating under reflux for 5 hours under a nitrogen atmosphere. After concentration, the resultant liquid was separated with a saturated aqueous solution of sodium bicarbonate and methylene chloride, and the resultant organic layer was concentrated. The crystal obtained was recrystallized with methanol and methylene chloride, and thus 4.3 g of Compound d-1-6 was obtained.

The structure of the obtained Compound d-1-6 was confirmed by MS (mass spectrum) measurement.

MS-ESI m/z=404.2 (M-H)$^+$ (v) Preparation of Compound d-1-9

To 150 ml of NMP (N-methylpyrrolidone), 1.22 g of Compound d-1-7 and 1.62 g of Compound d-1-6 were added and stirred at 70° C. for 3 hours under a nitrogen atmosphere. After that, 1.63 g of Compound d-1-8 was added thereto and stirred while heating at 160° C. for 8 hours. Then, 10.7 g of ammonium thiocyanate was added thereto and stirred at 160° C. for 8 hours. After concentration, water was added and filtration was conducted. The filtrate was purified by a silica gel column chromatography, and then it was added to a mixed solvent of 30 ml of acetone and 40 ml of a 1N sodium hydroxide aqueous solution and stirred for 24 hours at external temperature of 65° C. After the mixture was returned to room temperature, the pH was adjusted to 3 with hydrochloric acid, and the produced precipitate was filtrated, and thus 3.3 g of crude product D-1-1a was obtained.

This was dissolved in a methanol solution together with TBAOH (tetrabutylammonium hydroxide) and purified by means of a Sephadex LH-20 column. After a fraction in the main layer was recovered and concentrated, a 0.1M trifluoromethane sulfonic acid solution was added to adjust the pH to 3, and the produced precipitate was filtered, to obtain 2.4 g of Exemplified dye D-1-1a.

The structure of Exemplified dye D-1-1a obtained was confirmed by MS measurement.

MS-ESI m/z=928.1 (M-H)$^+$

Spectral absorption measurement of the obtained Exemplified dye D-1-1a was conducted with a solution prepared so that concentration of the dye in a 340 μmol/l tetrabutyl ammonium hydroxide methanol solvent was 17 mmol/l. As a result, the maximum absorption wavelength was 521 nm.

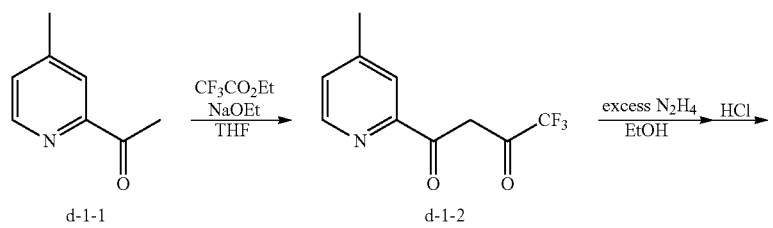
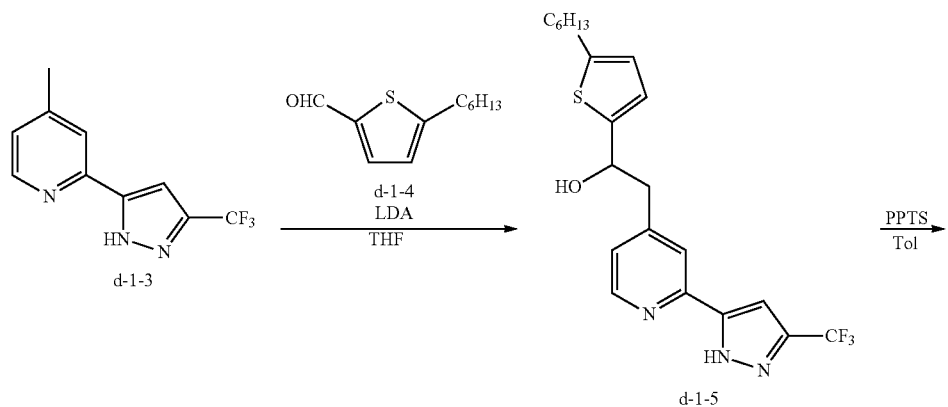
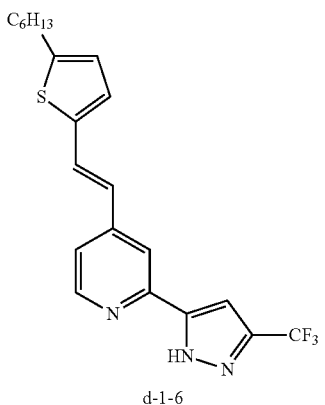
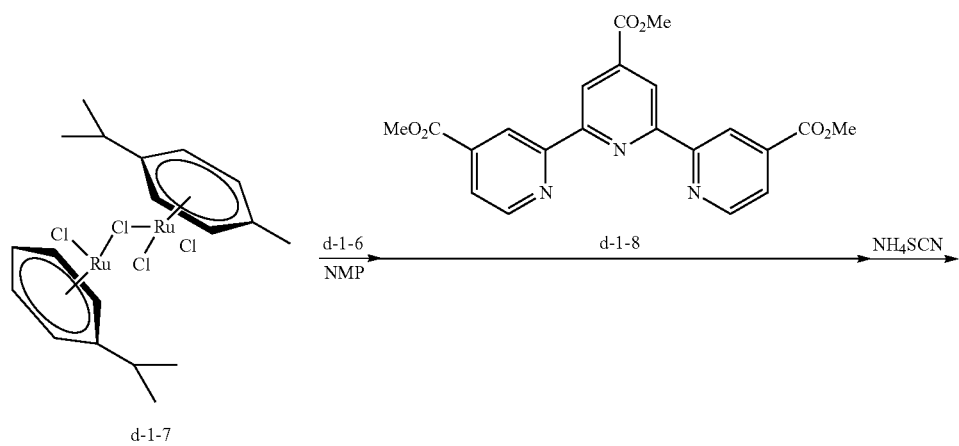

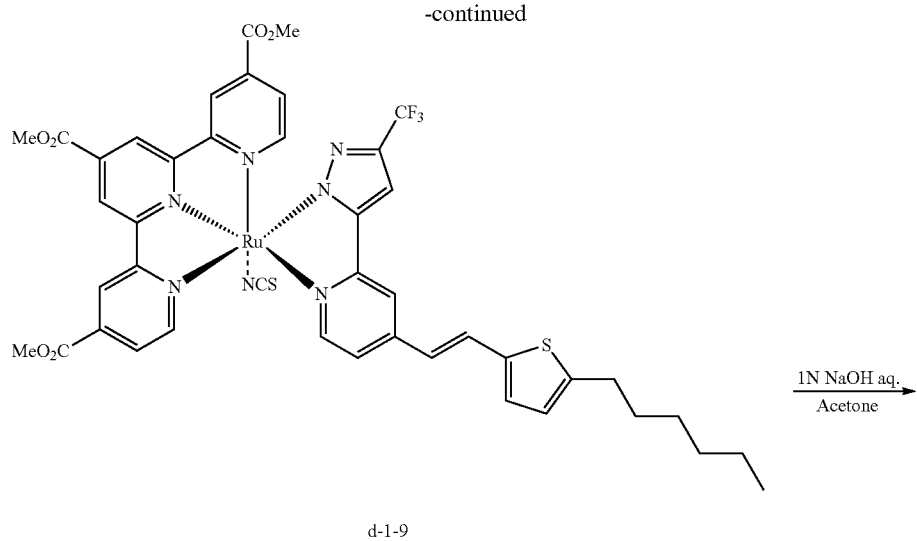

d-1-9

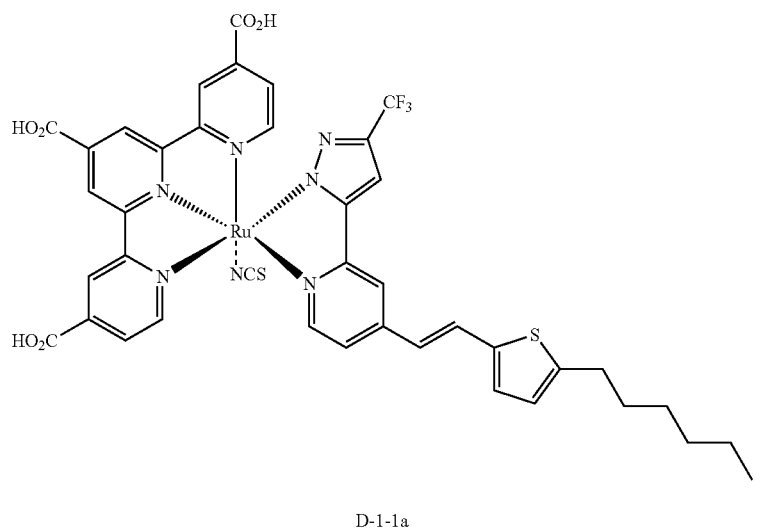

D-1-1a (Preparation of Exemplified Dye D-1-5a)

Compound d-2-2 was prepared according to the method shown in the following scheme, and Exemplified dye D-1-5a was prepared in a manner similar to Exemplified dye D-1-1a, except that Compound d-1-4 in Exemplified dye D-1-1a was replaced with Compound d-2-2.

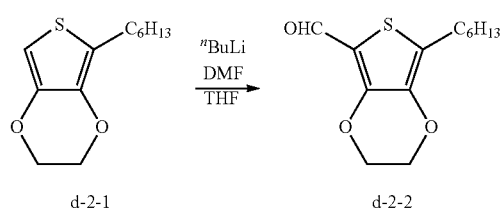

(Preparation of Exemplified Dye D-1-6a)

Compound d-3-3 was prepared according to the method shown in the following scheme, and Exemplified dye D-1-6a was prepared in a manner similar to Exemplified dye D-1-1a, except that Compound d-1-4 was replaced with Compound d-3-3.

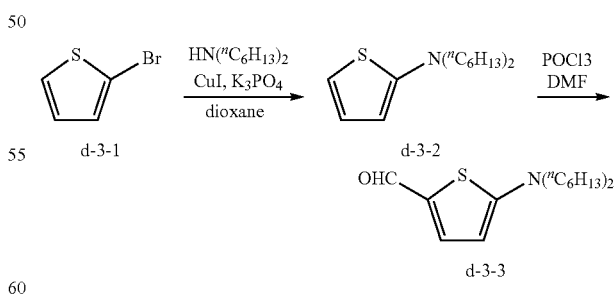

(Preparation of Exemplified Dye D-1-8a)

Compound d-4-2 was prepared according to the method shown in the following scheme, and Exemplified dye D-1-8a was prepared in a manner similar to Exemplified dye D-1-1a, except that Compound d-1-4 was replaced with Compound d-4-2.

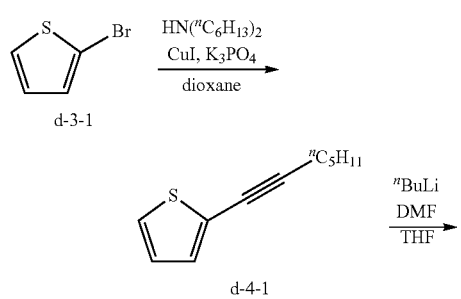
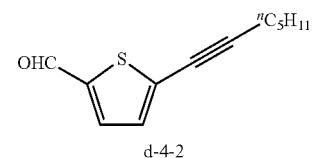

(Preparation of Exemplified Dye D-1-9a)

Compound d-5-8 was prepared according to the method shown in the following scheme, and Exemplified dye D-1-9a was prepared in a manner similar to Exemplified dye D-1-1a, except that Compound d-1-6 was replaced with Compound d-5-8.

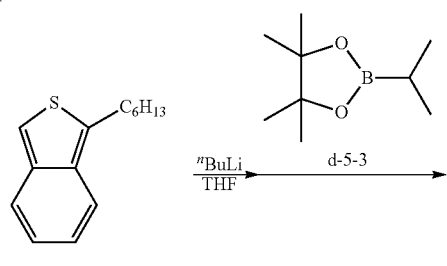
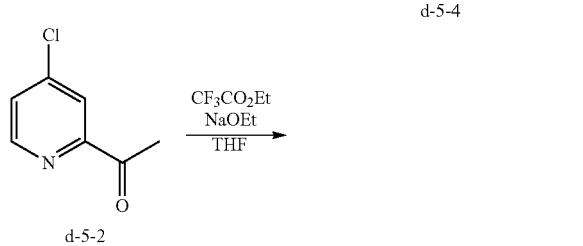

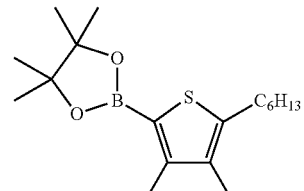
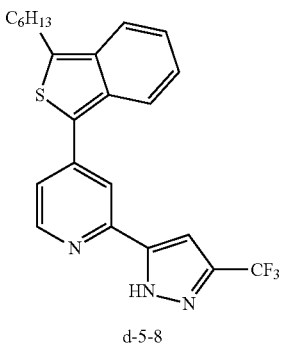
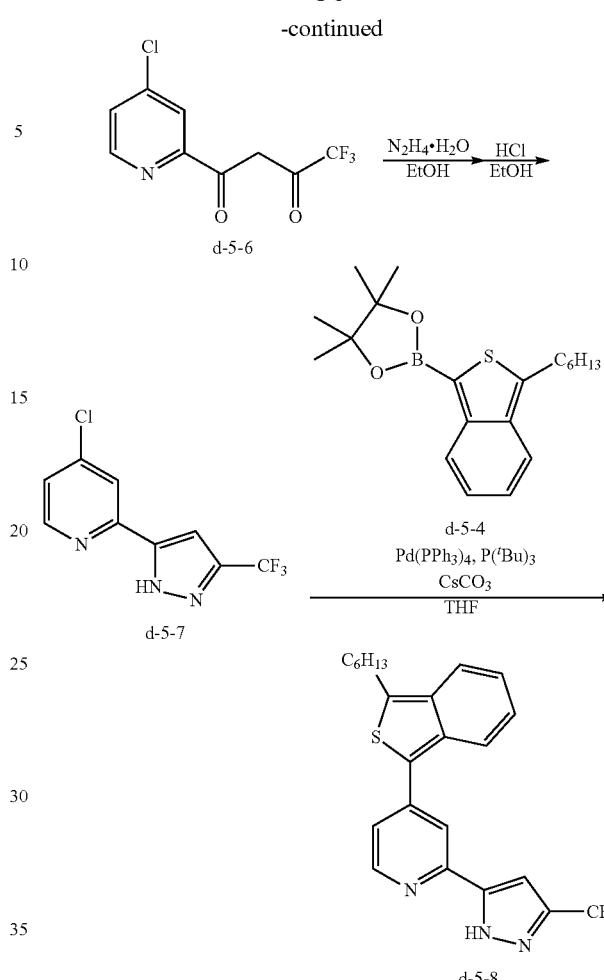

(Preparation of Exemplified Dye D-1-14a)

Exemplified dye D-1-14a was prepared in a manner similar to Exemplified dye D-1-9a, except that Compound d-5-1 was replaced with Compound d-6-1.

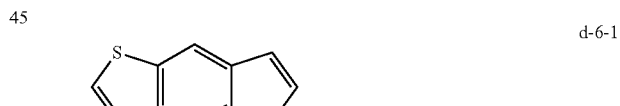

(Preparation of Exemplified Dye D-1-13a)

Exemplified dye D-1-13a was prepared in a manner similar to Exemplified dye D-1-9a, except that Compound d-5-1 was replaced with Compound d-7-1.

(Preparation of Exemplified Dye D-1-12a)

Exemplified dye D-1-12a was prepared in a manner similar to Exemplified dye D-1-9a, except that Compound d-5-1 was replaced with Compound d-7-2.

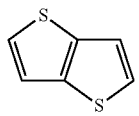

d-7-2

(Preparation of Exemplified Dye D-1-2a)

Compound d-8-2 was prepared according to the method shown in the following scheme, and Exemplified dye D-1-2a was prepared in a manner similar to Exemplified dye D-1-1a, except that Compound d-1-4 was replaced with Compound d-8-2.

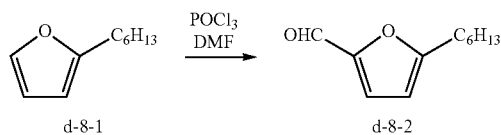

(Preparation of Exemplified Dye D-1-23a)

Compound d-5-1 in the preparation of Exemplified dye D-1-9a was replaced with the Compound d-9-1, and subsequently Exemplified dye D-1-23a was prepared in a manner similar to Exemplified dye D-1-1a.

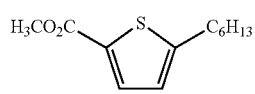

d-9-1

(Preparation of Exemplified Dye D-1-27a)

Compound d-5-1 in the preparation of Exemplified dye D-1-9a was replaced with Compound d-10-1, and subsequently Exemplified dye D-1-27a was prepared in a manner similar to Exemplified dye D-1-1a.

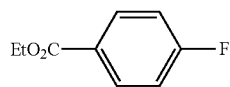

d-10-1

(Preparation of Exemplified Dye D-1-7a)

Compound d-11-1 was prepared according to the method shown in the following scheme, and Exemplified dye D-1-7a was prepared in a manner similar to Exemplified dye D-1-9a, except that Compound d-5-4 was replaced with Compound d-11-1

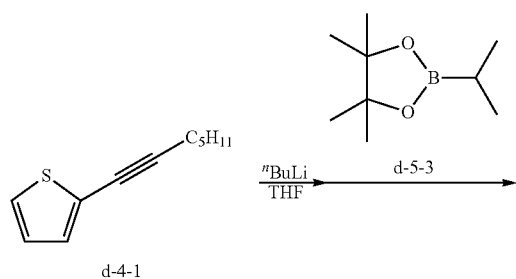

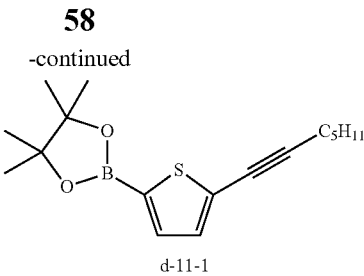

d-11-1

(Preparation of Exemplified Dye D-1-16a)

Exemplified dye D-1-16a was prepared in a manner similar to Exemplified dye D-1-1a, except that Compound d-1-1 was replaced with Compound d-14-1.

d-14-1

(Preparation of Exemplified Dye D-1-26a)

Compound d-13-3 was prepared according to the method shown in the following scheme, and Exemplified dye D-1-26a was prepared in a manner similar to Exemplified dye D-1-1a, except that Compound d-1-3 was replaced with Compound d-13-3.

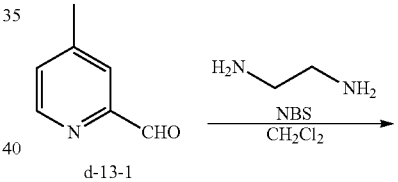

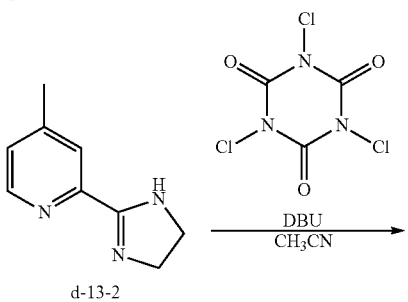

(Preparation of Exemplified Dye D-1-18a)

Exemplified dye D-1-18a was prepared in a manner similar to Exemplified dye D-1-1a, except that Compound d-1-1 was replaced with Compound d-20-1.

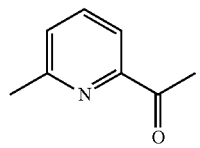
d-20-1
(Preparation of Exemplified Dye D-3-1a)
Exemplified dye D-3-1a was prepared in a manner similar to Exemplified dye D-1-1a and according to the method shown in the following scheme, except that Compound d-1-7 in the preparation of Exemplified dye D-1-1a was replaced with Compound d-15-1.
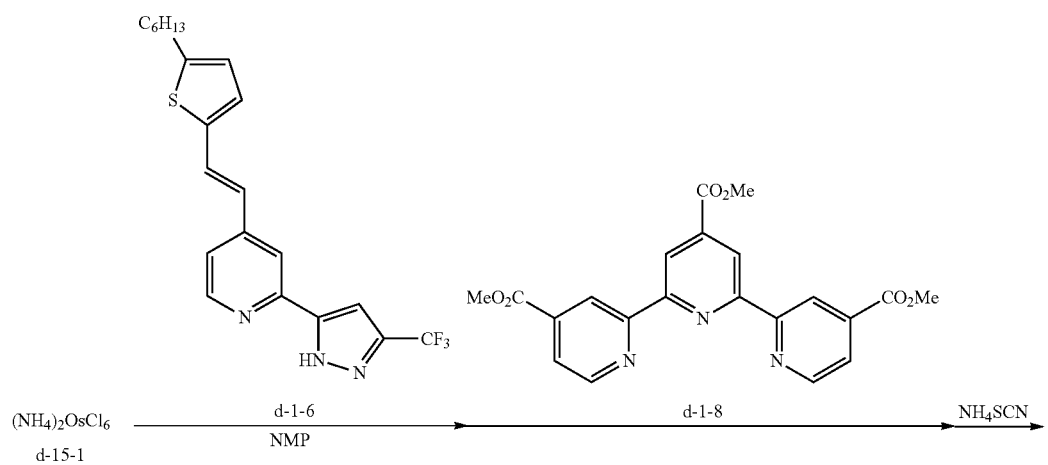
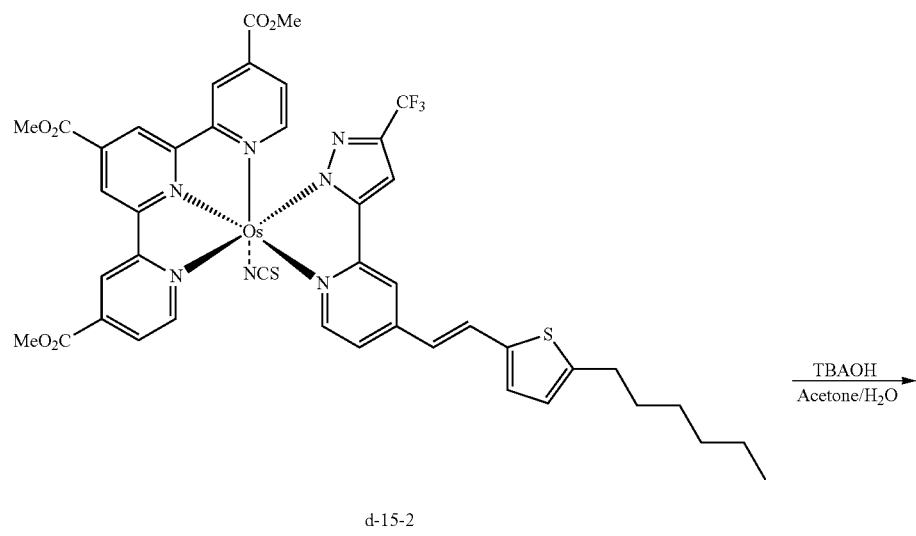
d-15-2

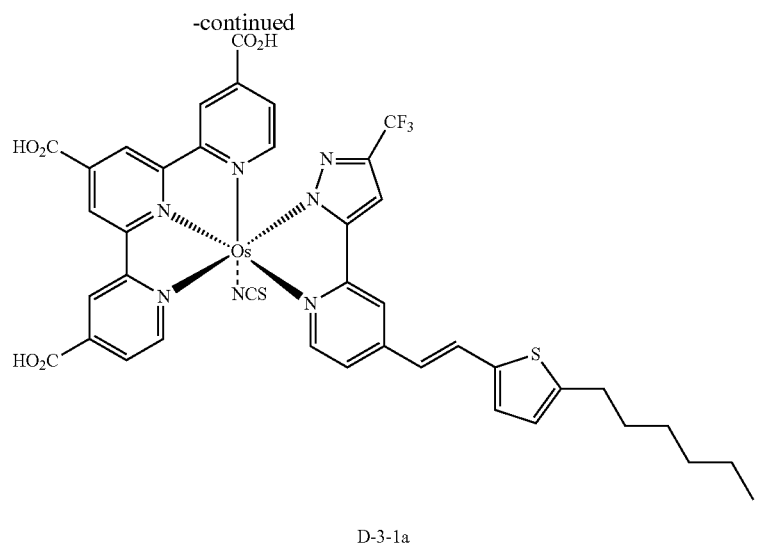

D-3-1a (Preparation of Exemplified Dye D-1-35a)

Compound d-16-2 was prepared according to the method shown in the following scheme, and Exemplified dye D-1-35a was prepared in a manner similar to Exemplified dye D-1-1a, except that Compound d-1-3 was replaced with Compound d-16-2.

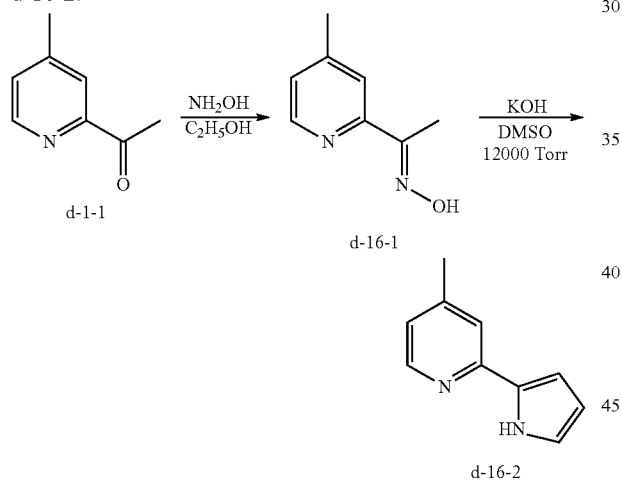

(Preparation of Exemplified Dye D-1-36a)

Compound d-17-3 was prepared according to the method shown in the following scheme, and Exemplified dye D-1-36a was prepared in a manner similar to Exemplified dye D-1-1a, except that Compound d-1-3 was replaced with Compound d-17-3.

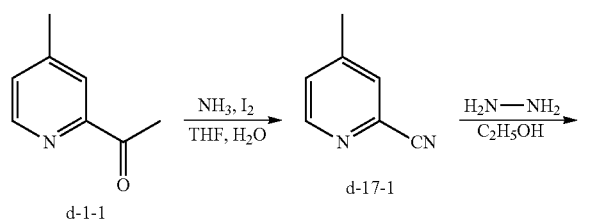

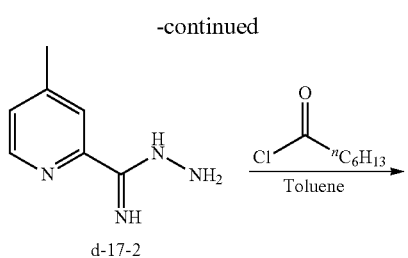

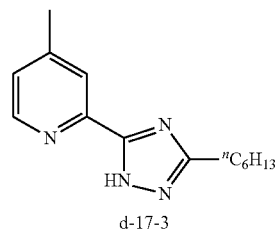

(Preparation of Exemplified Dye D-1-37a)

Compound d-18-1 was prepared according to the method shown in the following scheme, and Exemplified dye D-1-37a was prepared in a manner similar to Exemplified dye D-1-1a, except that Compound d-1-3 was replaced with Compound d-18-1.

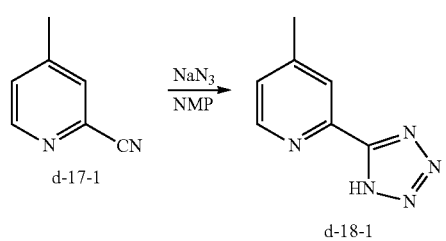

(Preparation of Exemplified Dye D-3-5a)

Exemplified dye D-3-5a was prepared in a manner similar to Exemplified dye D-1-1a, except that ammonium thiocyanate was replaced with Compound d-19-1.

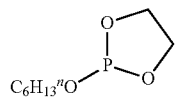

d-19-1

The structure of each of the dyes was confirmed by MS measurement.

The results of MS measurement of each of the dyes and the results of spectral absorption measurement which was conducted with a solution prepared so that concentration of the dye in a 340 mmol/l tetrabutyl ammonium hydroxide methanol solvent was 17 μmol/l and using a ultraviolet-visible spectrophotometer (UV-2400-PC, manufactured by Shimadzu Corporation) were shown together in the following Table 6.

TABLE 6

| Dye | MS-ESI | Max Ab. Wavelength*[1] |
|---|---|---|
| D-1-1a | MS-ESI m/z = 928.1(M − H)$^+$ | 521 |
| D-1-5a | MS-ESI m/z = 986.1(M − H)$^+$ | 521 |

TABLE 6-continued

| Dye | MS-ESI | Max Ab. Wavelength*[1] |
|---|---|---|
| D-1-6a | MS-ESI m/z = 1027.2(M − H)$^+$ | 519 |
| D-1-8a | MS-ESI m/z = 938.1(M − H)$^+$ | 520 |
| D-1-9a | MS-ESI m/z = 952.1(M − H)$^+$ | 522 |
| D-1-14a | MS-ESI m/z = 1008.1(M − H)$^+$ | 522 |
| D-1-13a | MS-ESI m/z = 1014.0(M − H)$^+$ | 522 |
| D-1-12a | MS-ESI m/z = 958.0(M − H)$^+$ | 521 |
| D-1-2a | MS-ESI m/z = 958.0(M − H)$^+$ | 519 |
| D-1-23a | MS-ESI m/z = 1026.2(M − H)$^+$ | 523 |
| D-1-27a | MS-ESI m/z = 954.1(M − H)$^+$ | 520 |
| D-1-7a | MS-ESI m/z = 912.1(M − H)$^+$ | 521 |
| D-1-16a | MS-ESI m/z = 928.1(M − H)$^+$ | 516 |
| D-1-26a | MS-ESI m/z = 860.1(M − H)$^+$ | 515 |
| D-1-18a | MS-ESI m/z = 928.1(M − H)$^+$ | 527 |
| D-3-1a | MS-ESI m/z = 1018.1(M − H)$^+$ | 612 |
| D-1-35a | MS-ESI m/z = 859.1(M − H)$^+$ | 524 |
| D-1-36a | MS-ESI m/z = 945.2(M − H)$^+$ | 520 |
| D-1-37a | MS-ESI m/z = 862.1(M − H)$^+$ | 513 |
| D-3-5a | MS-ESI m/z = 1062.2(M − H)$^+$ | 740 |

*[1]Maximum absorption wavelength (nm)

The metal complex dyes prepared by the above-described methods are dyes shown below and the same dyes but having tetrabutyl ammonium ion as their counter anions.

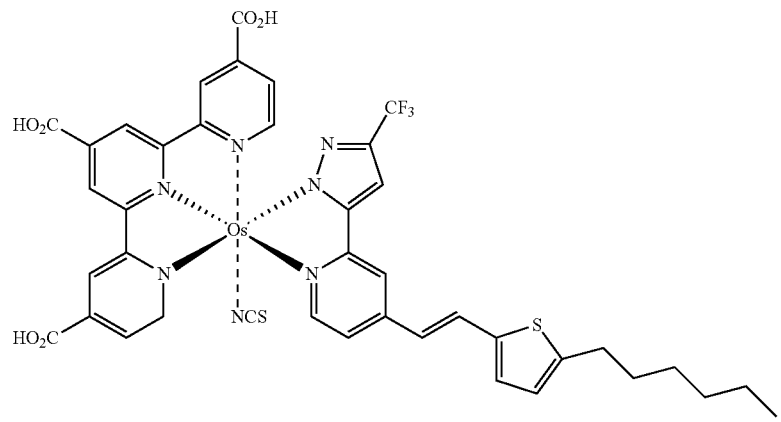

D-3-1a

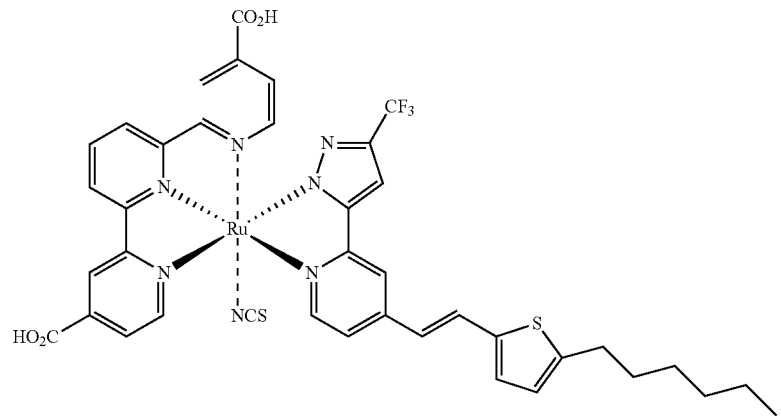

D-2-1a

-continued
D-1-26a
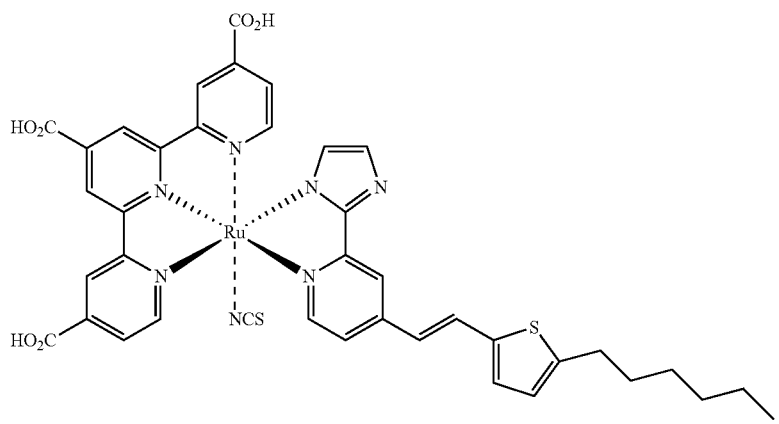
D-1-16a
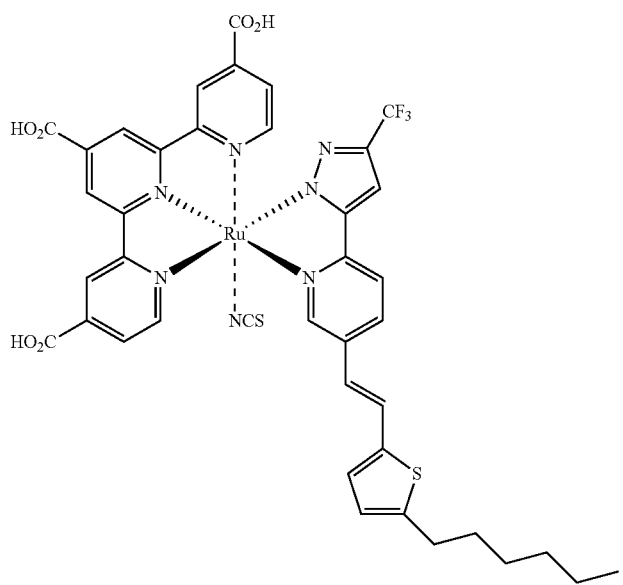
D-1-8a
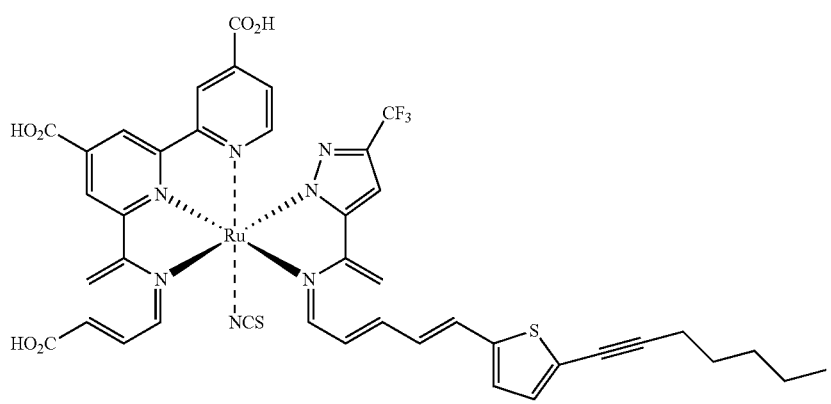

-continued
D-1-9a
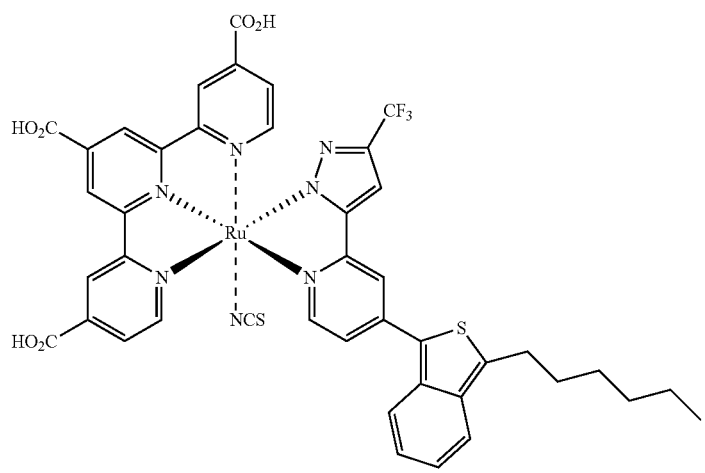
D-1-14a
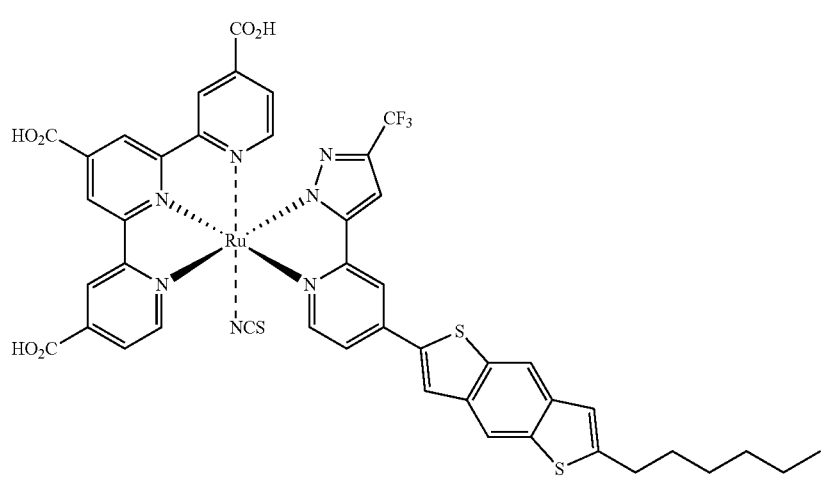
D-1-13a
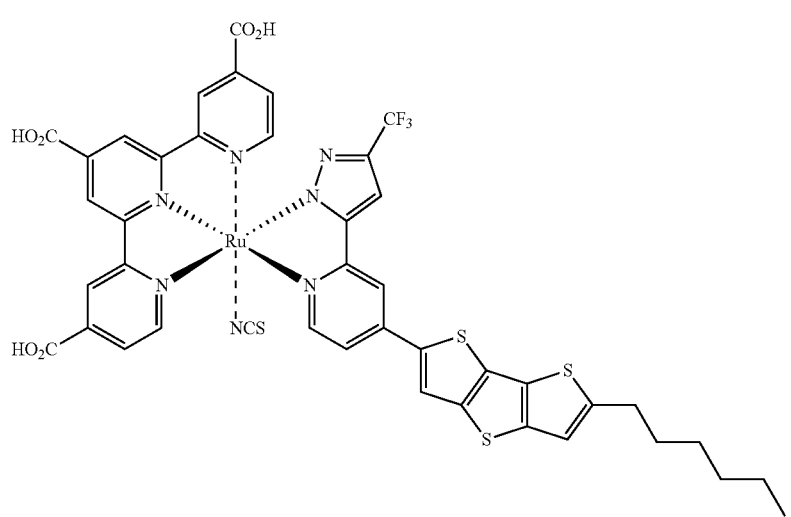

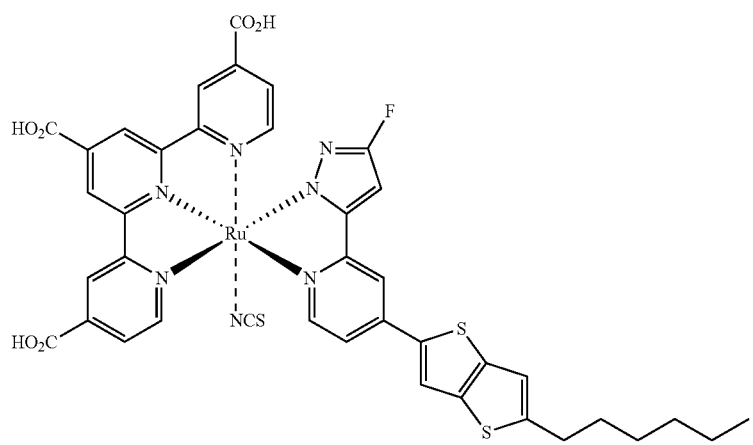
D-1-12a
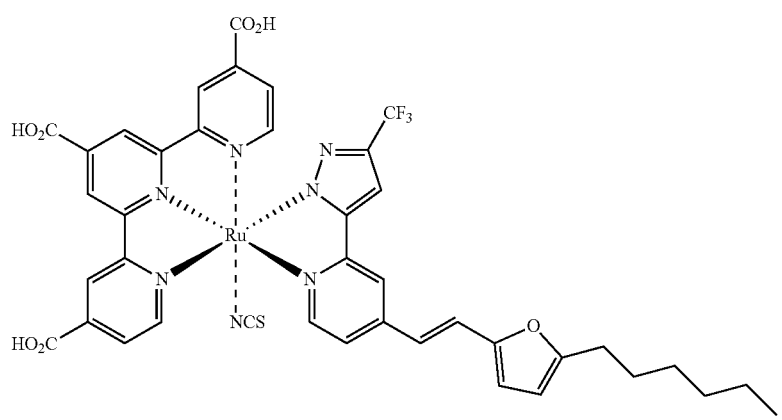
D-1-2a
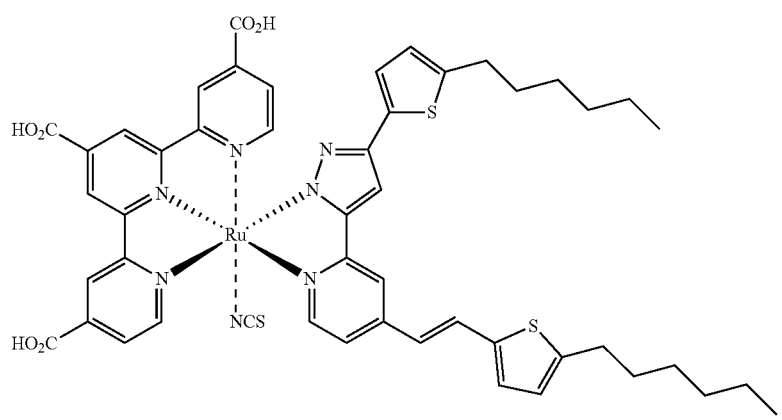
D-1-23a

D-1-27a
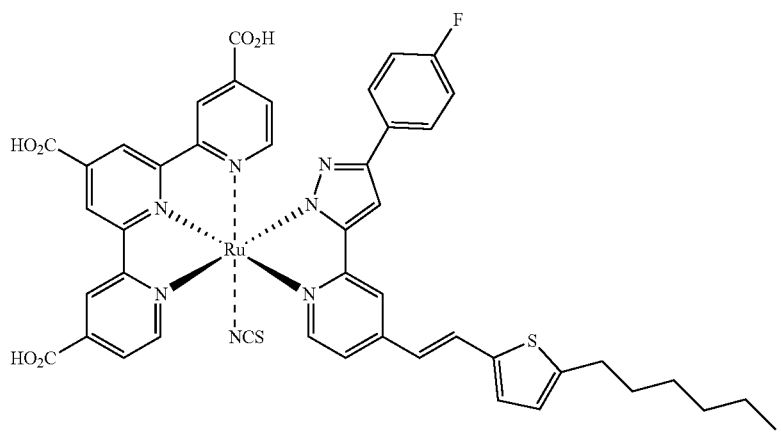
D-1-7a
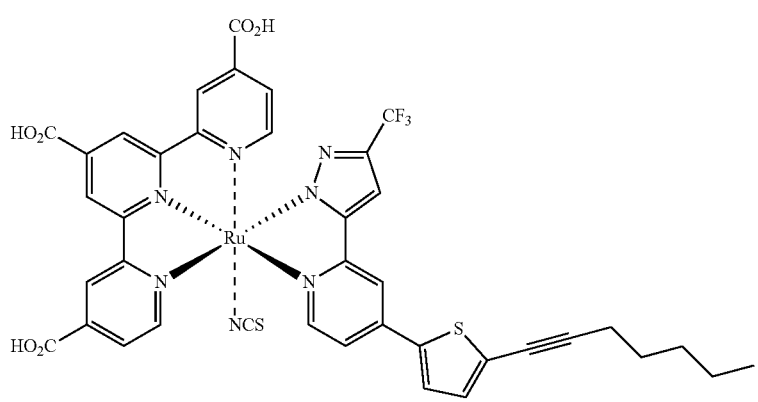
D-1-1a
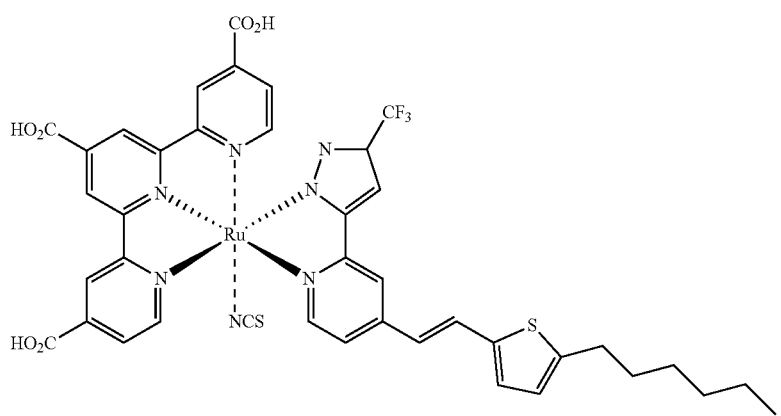

D-1-5a
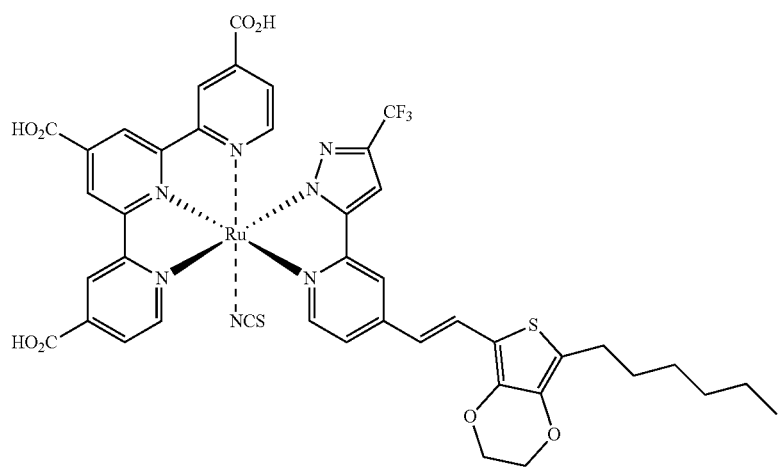
D-1-6a
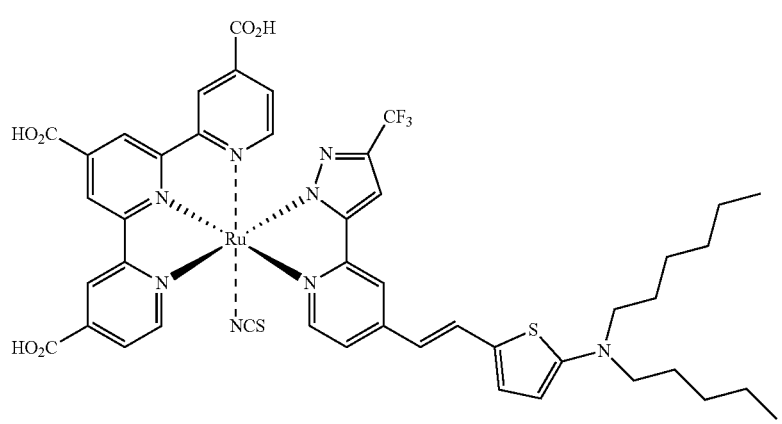
D-1-35a
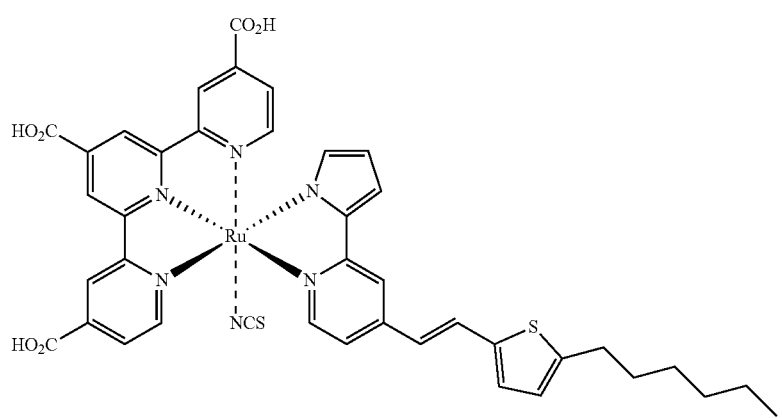

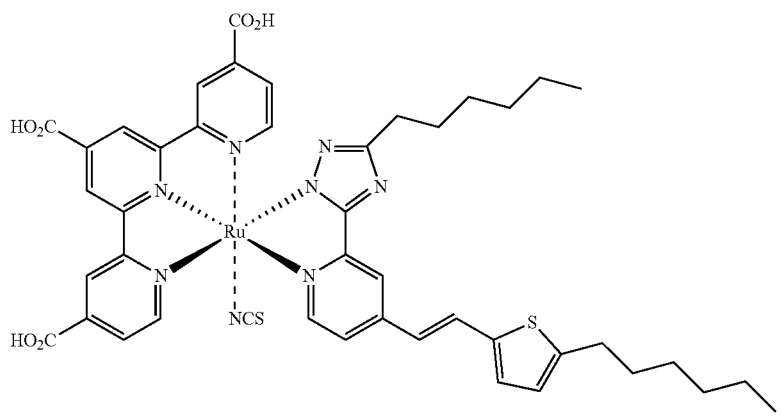

D-1-36a

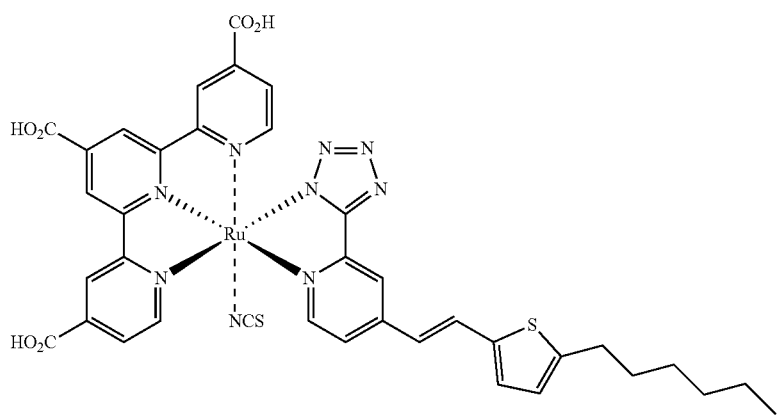

D-1-37a

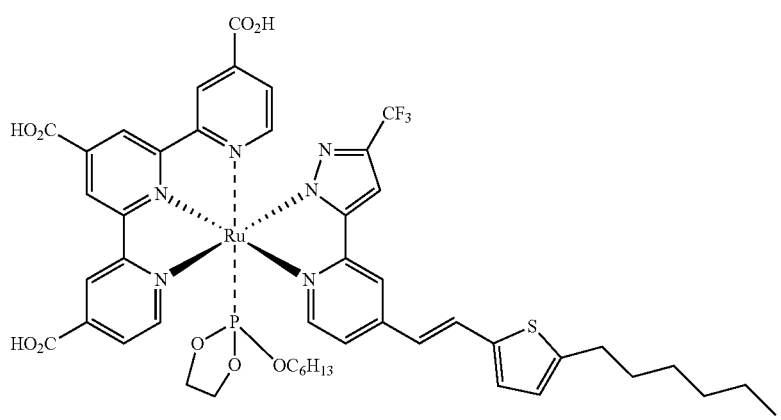

D-3-5a

Example 1

Various kinds of pastes for forming a semiconductor layer or a light-scattering layer of a semiconductor electrode that constitutes a photoelectrode were prepared, and dye-sensitized solar cells were produced using the pastes.

[Preparation of Paste]

First, the pastes for forming the semiconductor layer or the light-scattering layer of the semiconductor electrode that constitutes the photoelectrode were prepared in accordance with the compositions shown in Table 7. In the following preparation, a slurry was prepared by incorporating $TiO_2$ in a medium with stirring, and then a paste was obtained by adding a thickener to the slurry and kneading it.

TABLE 7

| Paste | TiO₂ particles | Medium | Thickening agent | Remarks |
|---|---|---|---|---|
| 1 | 1 | Nitric acid solution | CB | |
| 2 | 1, 2 | Nitric acid solution | CB | TiO₂1:TiO₂2 = 30:70 (mass ratio) |
| 3 | 1, S1 | Nitric acid solution | CB | Mass of TiO₂S1:Paste 1 = 10:90 (mass ratio) |
| 4 | 1, S1 | Nitric acid solution | CB | Mass of TiO₂S1:Paste 1 = 30:70 (mass ratio) |
| 5 | 1, S1 | Nitric acid solution | CB | Mass of TiO₂S1:Paste 1 = 50:50 (mass ratio) |
| 6 | 1, P1 | Nitric acid solution | CB | Mass of mica P1:Paste 1 = 20:80 (mass ratio) |
| 7 | 1, S2 | Nitric acid solution | CB | Mass of TiO₂S2:Paste 1 = 30:70 (mass ratio) |
| 8 | 1, S3 | Nitric acid solution | CB | Mass of TiO₂S3:Paste 1 = 30:70 (mass ratio) |
| 9 | 1, S4 | Nitric acid solution | CB | Mass of TiO₂S4:Paste 1 = 30:70 (mass ratio) |
| 10 | 1, S5 | Nitric acid solution | CB | Mass of TiO₂S5:Paste 1 = 30:70 (mass ratio) |
| 11 | 1, S6 | Nitric acid solution | CB | Mass of TiO₂S6:Paste 1 = 30:70 (mass ratio) |
| 12 | 1, S7 | Nitric acid solution | CB | Mass of TiO₂S7:Paste 1 = 30:70 (mass ratio) |
| 13 | 1, S8 | Nitric acid solution | CB | Mass of TiO₂S8:Paste 1 = 30:70 (mass ratio) |
| 14 | 1, S9 | Nitric acid solution | CB | Mass of TiO₂S9:Paste 1 = 30:70 (mass ratio) |

Figure 2:
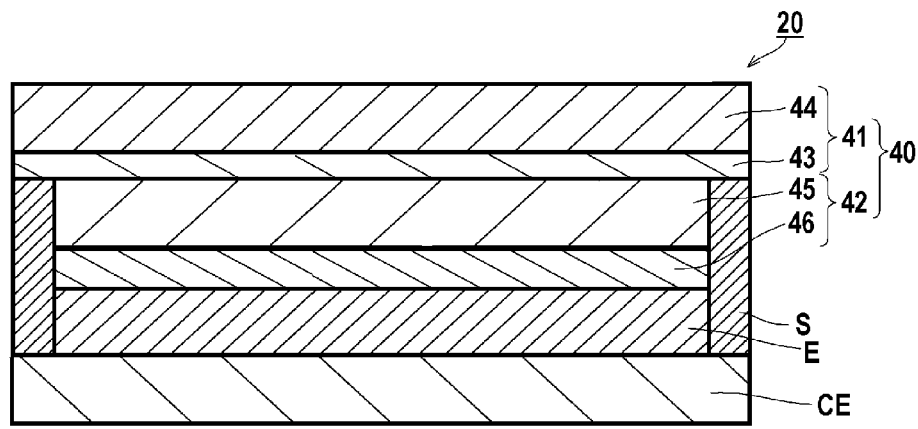
FIG. 2 is a cross-sectional view schematically showing the dye-sensitized solar cell produced in Example 1.
Figure 3:
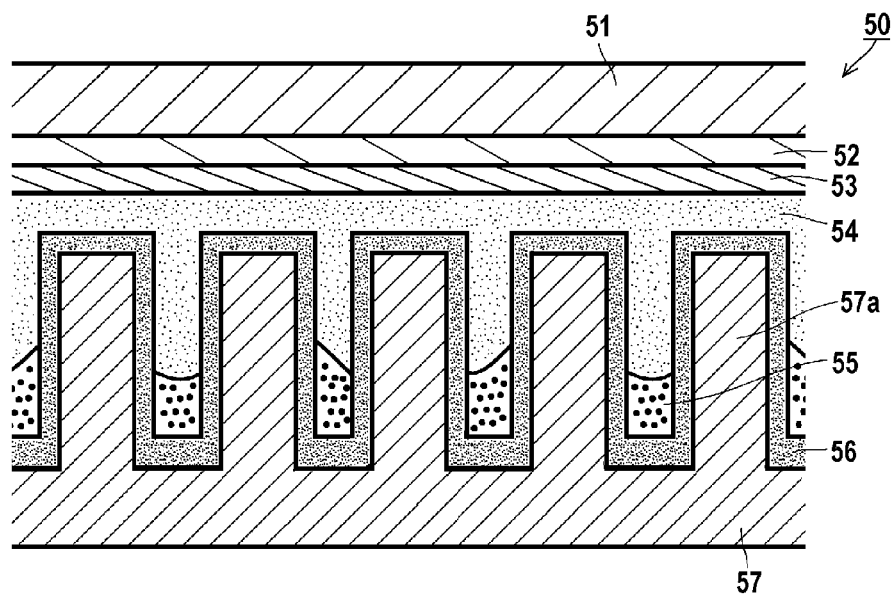
FIG. 3 is a cross-sectional view schematically showing the dye-sensitized solar cell produced in Example 2.

TiO₂ particle 1: anatase, average diameter; 25 nm
TiO₂ particle 2: anatase, average diameter; 200 nm
Rod-shaped TiO₂ particle S1: anatase, diameter; 100 nm, aspect ratio; 5
Rod-shaped TiO₂ particle S2: anatase, diameter; 30 nm, aspect ratio; 6.3
Rod-shaped TiO₂ particle S3: anatase, diameter; 50 nm, aspect ratio; 6.1
Rod-shaped TiO₂ particle S4: anatase, diameter; 75 nm, aspect ratio; 5.8
Rod-shaped TiO₂ particle S5: anatase, diameter; 130 nm, aspect ratio; 5.2
Rod-shaped TiO₂ particle S6: anatase, diameter; 180 nm, aspect ratio; 5
Rod-shaped TiO₂ particle S7: anatase, diameter; 240 nm, aspect ratio; 5
Rod-shaped TiO₂ particle S8: anatase, diameter; 110 nm, aspect ratio; 4.1
Rod-shaped TiO₂ particle S9: anatase, diameter; 105 nm, aspect ratio; 3.4
Plate-shaped mica particle P1: diameter; 100 nm, aspect ratio; 6
CB: cellulose-based binder According to the procedure described below, a photoelectrode having the same configuration as that of the photoelectrode 12 shown in FIG. 5 of JP-A-2002-289274 was produced, and using the photoelectrode, a dye-sensitized solar cell 1 of a scale of 10 mm×10 mm having the same configuration as that of the dye-sensitized solar cell 20 shown in FIG. 3 of JP-A-2002-289274 except for the photoelectrode, was produced. The specific configuration thereof was shown in FIG. 2 of the DRAWING attached to the present application. In FIG. 2 of the present application, 41 stands for a transparent electrode, 42 stands for a semiconductor electrode, 43 stands for a transparent conductive film, 44 stands for a substrate, 45 stands for a semiconductor layer, 46 stands for a light-scattering layer, 40 stands for a photoelectrode, 20 stands for a dye-sensitized solar cell, CE stands for a counter electrode, E stands for an electrolyte, and S stands for a spacer.

A transparent electrode in which a fluorine-doped SnO₂ conductive film (thickness: 500 nm) was formed on a glass substrate, was provided. On this SnO₂ conductive film, the above-described paste 2 was applied by screen printing, and then the paste was dried. Thereafter, the paste was calcined under the conditions of 450° C. in air. Furthermore, by repeating both the above screen printing and calcination using the paste 4, the semiconductor electrode A having the same configuration as that of the semiconductor electrode 42 shown in FIG. 2 (area of light-receiving surface: 10 mm×10 mm, layer thickness: 10 μm, layer thickness of the dye-adsorbing layer: 6 μm, layer thickness of the light-scattering layer: 4 μm, and content of the rod-shaped TiO₂ particles 1 contained in the light-scattering layer: 30% by mass) and the semiconductor electrode B (area of light-receiving surface: 10 mm×10 mm, layer thickness: 19 μm, layer thickness of the dye-adsorbing layer: 12 μm, layer thickness of the light scattering layer: 4 μm, and content of the rod-shaped TiO₂ particles 1 contained in the light scattering layer: 30% by mass) were formed on the SnO₂ conductive film. Thus, photoelectrode A and photoelectrode B, each of which did not contain any dye, were prepared.

Subsequently, a dye was adsorbed on the semiconductor electrodes A and B as follows. First, anhydrous ethanol which had been dehydrated with magnesium ethoxide was used as a solvent, and the metal complex dye described in Table 8 was dissolved in this anhydrous ethanol to a concentration of $3 \times 10^{-4}$ mol/L. Thus, a dye solution was prepared. Subsequently, the semiconductor electrode was immersed in this solution, and thereby, the dye was adsorbed on the semiconductor electrode in an amount of about $1.5 \times 10^{-7}$ mol/cm². Thus, a photoelectrode 40 was completed.

Subsequently, a platinum electrode (thickness of Pt thin film: 100 nm) having the same shape and size as those of the photoelectrode described above was produced as a counter electrode, and an iodine-based redox solution containing iodine and lithium iodide was prepared as an electrolyte E. Furthermore, a spacer-S (trade name: "Surlyn") manufactured by DuPont Company, which had a shape matching the size of the semiconductor electrode, was prepared. As shown in FIG. 3 of JP-A-2002-289274, the photoelectrode 40 and the counter electrode CE were arranged to face each other, with the spacer-S interposed therebetween, and the electrolyte described above was filled in the inside. Thus, a dye-sensitized solar cell using a photoelectrode A (cell A) and a dye-sensitized solar cell using a photoelectrode B (cell B) were completed. The performance evaluation of these solar cells was conducted. The results are shown in Table 8.

(Test Method)

A cell characterization test was carried out, and the conversion efficiencies η of the dye-sensitized solar cells were measured. The cell characteristics evaluation test was carried out using a solar simulator (manufactured by Wacom Electric Co., Ltd., WXS-85-H type), by irradiating pseudo-sunlight of 1000 W/cm², from a xenon lamp through an AM1.5 filter. The current-voltage characteristics were measured using an I-V tester, and the photoelectric conversion efficiency η [%] was determined.

Further, the IPCE (quantum yield) at the range of 300 to 900 nm was measured using an IPCE measurement apparatus manufactured by Peccell Technologies, Inc. Values of IPCE at 700 nm and 800 nm are shown in the following Table 8.

For measurement of $\epsilon$, preparation was carried out so that the concentration of dye in a 340 μmol/l tetrabutyl ammonium hydroxide methanol solvent was 17 μmol/l, and spectral absorption measurement was conducted.

B, performed light harvesting efficiently and also maintained the values of IPCE at both 700 nm and 800 nm at a high level.

Further, the same tests as above were conducted using the pastes 1 to 14 other than the above-described paste 2. As a result, it was confirmed that good performances were obtained by each of the samples using the metal complex dye of the present invention.

TABLE 8

| Sample No. | Metal complex dye | $\epsilon$ at 700 nm ($\times 10^3$) | $\epsilon$ at 800 nm ($\times 10^2$) | Cell A | | | Cell B | | | Remarks |
|---|---|---|---|---|---|---|---|---|---|---|
| | | | | IPCE at 700 nm | IPCE at 800 nm | Initial conversion efficiency($\eta i$) | IPCE at 700 nm | IPCE at 800 nm | Initial conversion efficiency($\eta i$) | |
| 101 | D-3-1a | 2.52 | 6.8 | 55 | 38 | 6.0 | 62 | 43 | 6.6 | This invention |
| 102 | D-1-18a | 2.38 | 8.1 | 57 | 47 | 6.3 | 63 | 50 | 6.9 | This invention |
| 103 | D-1-26a | 2.41 | 7.1 | 59 | 46 | 6.7 | 65 | 50 | 7.2 | This invention |
| 104 | D-1-16a | 2.59 | 6.9 | 63 | 46 | 6.6 | 65 | 50 | 7.1 | This invention |
| 105 | D-1-8a | 2.62 | 8.8 | 63 | 49 | 7.1 | 68 | 52 | 7.5 | This invention |
| 106 | D-1-9a | 2.30 | 8.7 | 64 | 48 | 7.2 | 67 | 51 | 7.6 | This invention |
| 107 | D-1-14a | 2.68 | 8.7 | 64 | 47 | 7.0 | 68 | 50 | 7.4 | This invention |
| 108 | D-1-13a | 2.70 | 8.4 | 64 | 49 | 7.1 | 68 | 52 | 7.5 | This invention |
| 109 | D-1-12a | 2.65 | 8.3 | 63 | 48 | 7.3 | 67 | 51 | 7.7 | This invention |
| 110 | D-1-2a | 2.57 | 7.9 | 65 | 47 | 7.2 | 69 | 50 | 7.6 | This invention |
| 111 | D-1-23a | 2.62 | 8.0 | 63 | 48 | 7.2 | 67 | 51 | 7.7 | This invention |
| 112 | D-1-27a | 2.45 | 8.1 | 64 | 48 | 7.2 | 68 | 51 | 7.6 | This invention |
| 113 | D-1-7a | 2.56 | 8.2 | 65 | 49 | 7.4 | 69 | 52 | 7.8 | This invention |
| 114 | D-1-1a | 2.60 | 9.0 | 69 | 52 | 7.9 | 72 | 54 | 8.2 | This invention |
| 115 | D-1-5a | 2.71 | 9.1 | 70 | 51 | 7.9 | 73 | 53 | 8.1 | This invention |
| 116 | D-1-6a | 3.20 | 8.7 | 70 | 52 | 7.9 | 73 | 54 | 8.2 | This invention |
| C11 | S-1 | 1.65 | 5.9 | 36 | 29 | 5.1 | 54 | 38 | 6.1 | Comparative example |
| C12 | S-2 | 1.98 | 6.3 | 43 | 30 | 5.2 | 59 | 39 | 6.1 | Comparative example |

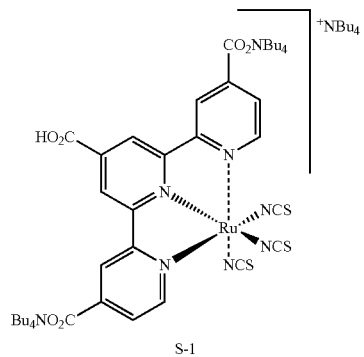

S-1

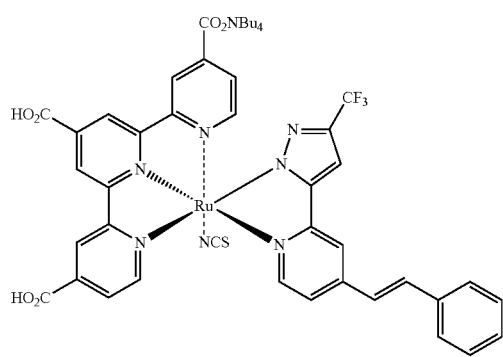

S-2

It is presumed that because of high values of c at both 700 nm and 800 nm of the present invention, even the cell A having a thinner film thickness of the oxide semiconductor and a smaller adsorption amount of dye than those of the cell Example 2

According to the procedure described below, a dye-sensitized solar cell having the same configuration as that shown in FIG. 1 of JP-A-2010-218770 was produced. The specific configuration thereof was shown in FIG. 3 of the DRAWING attached to the present application. In FIG. 3 of the present application, 51 stands for a transparent substrate, 52 stands for a transparent conductive film, 53 stands for a barrier layer, 54 stands for an n-type semiconductor electrode, 55 stands for a p-type semiconductor layer, 56 stands for a p-type semiconductor film, and 57 stands for a counter electrode (57a stands for a protrusion of the counter electrode).

On a transparent glass plate as the transparent substrate 51 of 20 mm×20 mm×1 mm, $SiO_2$:F (fluorine-doped Tin oxide) as the transparent conductive film 52 was formed by CVD, to prepare a transparent electrically conductive (Transparent Conductive Oxide: TCO) glass substrate.

Next, 5 ml of a solution in which $Ti[OCH(CH_3)_2]_4$ was mixed with water in the volume ratio of 4:1, was mixed with 40 ml of a ethyl alcohol solution of which pH was adjusted to 1 with a hydrochloride, to prepare a $TiO_2$ precursor solution. Then, this solution was spin-coated at 1000 rpm on the TCO glass substrate, and after performing a sol-gel synthesis, it was heated at 78° C. for 45 minutes under vacuum and subjected to annealing at 450° C. for 30 minutes. Thus, a barrier layer (53) composed of a titanium oxide thin film was formed.

Meanwhile, anatase-type titanium oxide particles having an average particle diameter of 18 nm (particle diameter: from 10 nm to 30 nm) were dispersed uniformly in an ethanol/methanol mixed solvent (ethanol:methanol=10:1 (volume ratio)), to prepare a slurry of titanium oxide. At this time, the titanium oxide particles were dispersed uniformly using a homogenizer in the proportion of 10% by mass with respective to 100% by mass of the mixed solvent.

Next, a solution in which ethyl cellulose as a viscosity adjuster was dissolved in ethanol so that its concentration was 10% by mass and an alcoholic organic solvent (terpineol) were added to the above-prepared slurry of titanium oxide, and the mixture was dispersed uniformly again using a homogenizer. After that, alcohols other than terpineol were removed using an evaporator. Then, mixing was conducted using a mixer, to prepare a paste-like titanium oxide-particle-containing composition. The composition of the prepared titanium oxide-particle-containing composition was that the percentage of the titanium oxide particles was 20% by mass and the percentage of the viscosity adjustor was 5% by mass, with respect to 100% by mass of the titanium oxide-particle-containing composition.

The thus-prepared titanium oxide-particle-containing composition was coated, on the barrier layer 53 formed as described above, by a screen printing so that a predetermined pattern was formed, and then dried at 150° C., and then heated at 450° C. in an electric furnace. Thus, a laminate in which the n-type semiconductor electrode 54 was laminated on the TCO glass substrate was obtained. Subsequently, after soaking the laminate overnight in a zinc nitrate ($ZnNO_3$) solution, a surface treatment was conducted by heating at 450° C. for 45 minutes. After that, using any one of various kinds of dyes shown in Table 8, an ethanol solution of the dye (concentration of the sensitizing dye: $1 \times 10^{-4}$ mol/L) was prepared, and the surface-treated laminate was soaked in the ethanol solution, and left at 25° C. for 24 hours, thereby adsorbing the dye on the interior of the n-type semiconductor electrode 54.

Subsequently, CuI was added to acetonitrile, to prepare a saturated solution. From the saturated solution, 6 ml of the supernatant liquid was taken out, and 15 mg of 1-methyl-3-ethylimidazolium thiocyanate was added thereto. Thus, a p-type semiconductor solution was prepared. Further, on a hot plate having been heated at 80° C., the above-described laminate after the dye had been incorporated in the n-type semiconductor electrode 54 was disposed. Then, the p-type semiconductor solution was dropped with a pipette and coated on the n-type semiconductor electrode 54, to impregnate it therein, and then dried by allowing it to stand for 1 minute as it is. Thus, a p-type semiconductor layer 55 was prepared.

Next, a 1 mm-thick copper plate was washed with a 1 molar hydrochloric acid, and then washed with a dehydrated ethanol, and then heated at 500° C. in the atmosphere for 4 hours, thereby preparing a copper plate on which a CuO nanowires (protrusions 57a) having 100 nm of maximum diameter and 10 μm of height were grown. The copper plate was encapsulated with an iodine crystal in an airtight container, and heated in a thermostatic chamber regulated at 60° C. for 1 hour, thereby preparing a counter electrode 57 on the surface of which a thin Cu I layer (p-type semiconductor film 56) was coated. Then, the counter electrode 57 was laminated on the above-described laminate, by pressing the counter electrode 57 against the laminate from the side of the p-type semiconductor layer 55.

The initial conversion efficiencies of the dye-sensitized solar cells thus prepared were measured in the same manner as Example 1. As a result, it was confirmed that according to the dyes of the present invention, good performances and improved effects are achieved in each of them.

Example 3

Figure 4:
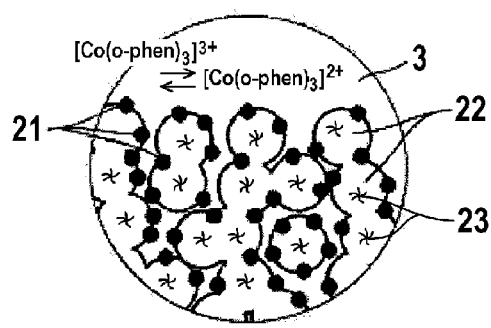
FIG. 4 is a cross-sectional view schematically showing the dye-sensitized solar cell produced in Example 3, which is a variation of the photoelectric conversion element shown in FIG. 1 in the point of the enlarged portion (circle).

In accordance with the following method, the dye-sensitized solar cell shown in FIG. 4 was prepared by subjecting a photoelectrode to a CdSe quantum dot-making treatment, and employing an electrolyte using a cobalt complex.

An ethanol solution of titanium(IV)bis(acetylacetonato) diisopropoxide was sprayed 16 times onto the surface of FTO glass (1) (manufactured by Nippon Sheet Glass Co., Ltd., surface resistance: 8 $\Omega sq^{-1}$), and calcined at 450° C. for 30 minutes or more. On this substrate, a transparent layer of about 2.1 μm composed of 20 nm-$TiO_2$ and a light-scattering layer of about 6.2 μm composed of 60 nm-$TiO_2$ (manufactured by Showa Titanium Co., Ltd.) were laminated by a screen printing, and then subjected to an aftertreatment with a $TiCl_4$ aqueous solution. Thus, a FTO/$TiO_2$ film 2 was prepared.

The FTO/$TiO_2$ film was soaked in a 0.03 molar $Cd(NO_3)_2$ ethanol solution for 30 seconds in a glove bag under an inert gas atmosphere, and then successively soaked in a 0.03 molar selenide ethanol solution for 30 seconds. After that, the film was washed in ethanol for 1 minute or more to remove an excessive precursor, and dried. These steps of: soaking→washing→drying were repeated 5 times to make the CdSe quantum dots (23) grow in the titanium oxide layer (22). Then, the resultant was subjected to a surface stabilization treatment with CdTe. In this manner, a CdSe-processed photoelectrode was prepared.

The selenide ($Se^{2-}$) was prepared within the system by adding 0.068 g of $NaBH_4$ (so as to be 0.060 mole concentration) to a 0.030 molar $SeO_2$ ethanol solution.

The CdSe-processed photoelectrode was soaked for 4 hours in the dye solution (ex. 1=0.3 mM Z907 Na acetonitrile/t-butanol (1:1) solution and ex. 2=0.1 mM SQ1 ethanol solution) to adsorb the dye (21) onto the photoelectrode. After that, the photoelectrode and the counter electrode (4, a product obtained by chemically depositing Pt on a FTO glass at 400° C. for 20 minutes from a 2-propanol solution of hexachloroplatinate (0.05 M)) were put together by sandwiching a 5um-thick Surlyn (manufactured by DuPont Kabushiki Kaisha) ring between them, and sealed by thermal dissolution. An electrolyte using a cobalt complex (an acetonitrile/ethylene carbonate (4:6/v:v) solution of 0.75M Co (o-phen)$_3$$^{2+}$, 0.075M Co (o-phen)$_3$$^{3+}$, and 0.20M LiClO$_4$) was injected into the interspace 3 between the electrodes through an opening preliminarily made in the side of the counter electrode. After that, the opening was closed by heat with a BYNEL (manufactured by DuPont Kabushiki Kaisha) sheet and a thin glass slide, to prepare a dye-sensitized solar battery cell 10.

The cobalt complex added to the electrolyte was prepared in accordance with a method described in Chemical Communications, Vol. 46, pages 8788 to 8790 (2010).

The initial conversion efficiencies of the dye-sensitized solar cells thus prepared were measured in the same manner as Example 1. As a result, it was confirmed that according to the dyes of the present invention, good performances and improved effects are achieved in each of them.

Example 4

Evaluation of device performance was conducted in the same manner as in Example 1, except that those materials shown in the following Tables 9 and 10 were used as a coexisting dye and/or a co-adsorbent. Herein, as to the amount of the metal complex dye, the total amount was maintained as described above, and the coexisting dye was contained in the amount of 30% by mole with respect to the total amount of dyes. The co-adsorbent was added in the proportion of 20 moles based on 1 mole of the total amount of the dye. In the following tables, improvement effects on both the initial photoelectric conversion efficiencies and the reduction rate after storing in the dark (heat resistance) are shown in accordance with the following criteria.
AA: An increase of 2% or more was observed.
A: An increase of 1% or more and less than 2% was observed.
B: An increase of 0% or more and less than 1% was observed.
C: A decrease in performance was observed.

TABLE 9

| Sample No. | | Dye | Coexisting dye | Change of conversion efficiency (Δηi) | Heat resistance[1] |
|---|---|---|---|---|---|
| 201 | A | D-3-1a | S-5 | AA | 9 |
| | B | D-3-1a | R-3 | AA | 8 |

TABLE 9-continued

| Sample No. | | Dye | Coexisting dye | Change of conversion efficiency (Δηi) | Heat resistance[1] |
|---|---|---|---|---|---|
| | C | D-3-1a | S-4 | A | 9 |
| | D | D-3-1a | None | — | 10 |
| 202 | A | D-1-18a | S-5 | AA | 6 |
| | B | D-1-18a | R-3 | AA | 7 |
| | C | D-1-18a | S-4 | A | 6 |
| | D | D-1-18a | None | — | 7 |
| 203 | A | D-1-26a | S-5 | AA | 6 |
| | B | D-1-26a | R-3 | AA | 5 |
| | C | D-1-26a | S-4 | A | 6 |
| | D | D-1-26a | None | — | 6 |
| 204 | A | D-1-16a | S-5 | AA | 6 |
| | B | D-1-16a | R-3 | AA | 7 |
| | C | D-1-16a | S-4 | A | 6 |
| | D | D-1-16a | None | — | 7 |
| 205 | A | D-1-8a | S-5 | AA | 4 |
| | B | D-1-8a | R-3 | AA | 5 |
| | C | D-1-8a | S-4 | A | 4 |
| | D | D-1-8a | None | — | 5 |
| 206 | A | D-1-1a | S-5 | AA | 2 |
| | B | D-1-1a | R-3 | AA | 3 |
| | C | D-1-1a | S-4 | A | 2 |
| | D | D-1-1a | None | — | 3 |
| 207 | A | D-1-35a | S-5 | AA | 5 |
| | B | D-1-35a | R-3 | AA | 6 |
| | C | D-1-35a | S-4 | A | 6 |
| | D | D-1-35a | None | — | 6 |
| 208 | A | D-1-36a | S-5 | AA | 6 |
| | B | D-1-36a | R-3 | AA | 6 |
| | C | D-1-36a | S-4 | A | 6 |
| | D | D-1-36a | None | — | 5 |
| 209 | A | D-1-37a | S-5 | AA | 6 |
| | B | D-1-37a | R-3 | AA | 6 |
| | C | D-1-37a | S-4 | A | 5 |
| | D | D-1-37a | None | — | 6 |
| 210 | A | D-3-5a | S-5 | A | 7 |
| | B | D-3-5a | R-3 | AA | 8 |
| | C | D-3-5a | S-4 | A | 6 |
| | D | D-3-5a | None | — | 7 |
| C21 | A | S-1 | S-5 | B | 24 |
| | B | S-1 | S-4 | C | 22 |
| | C | S-1 | None | — | 19 |

[1]Reduction ratio of conversion efficiency (%) after 500 hours leaving at 80° C. in a dark place.

S-4

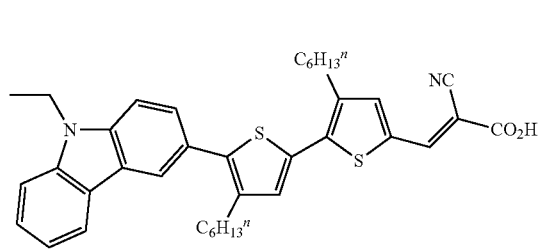

R-3

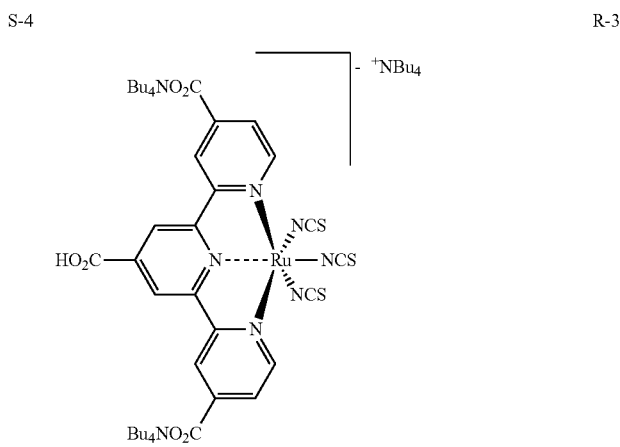

-continued

S-5

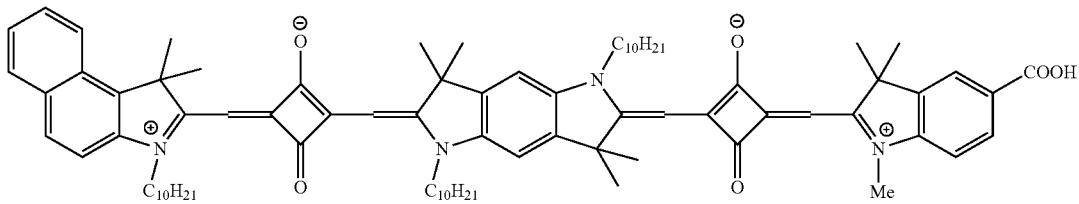

As for each of the coexisting dyes, measurement of spectral absorption was conducted with adjusting a dye concentration to 17 μmol/l in a 340 μmol/l tetrabutylammonium hydroxide methanol solvent, and using an ultraviolet-visible spectrophotometer (UV-2400-PC, manufactured by Shimadzu Corporation). As a result, the maximum absorption wavelengths thereof were the following values.

S-4: 478 nm
R-3: 590 nm
S-5: 768 nm

TABLE 10

| Sample No. | | Dye | Co-adsorbent | Change of conversion efficiency ($\Delta\eta i$) |
|---|---|---|---|---|
| 311 | A | D-3-1a | Chenodeoxycholic acid | AA |
| | B | D-3-1a | Cholic acid | AA |
| | C | D-3-1a | Deoxycholic acid | AA |
| | D | D-3-1a | Butanoic acid | A |
| | E | D-3-1a | Decanoic acid | A |
| 312 | A | D-1-18a | Chenodeoxycholic acid | AA |
| | B | D-1-18a | Cholic acid | AA |
| | C | D-1-18a | Deoxycholic acid | AA |
| | D | D-1-18a | Butanoic acid | A |
| | E | D-1-18a | Decanoic acid | A |
| 313 | A | D-1-26a | Chenodeoxycholic acid | AA |
| 314 | A | D-1-16a | Chenodeoxycholic acid | AA |
| 315 | A | D-1-7a | Chenodeoxycholic acid | AA |
| 316 | A | D-1-1a | Chenodeoxycholic acid | AA |
| 317 | A | D-3-5a | Chenodeoxycholic acid | AA |

As is evident from the above results, it is understood that conspicuous improvement effects are produced by coexistence of the specific coexisting dye or co-adsorbent in the photoelectric conversion element of the present invention.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Electrically conductive support
2 Photoconductor layer
21 Dye
22 Semiconductor fine particle
23 CdSe quantum dot
3 Charge transfer layer
4 Counter electrode
5 Light-receiving electrode
6 Circuit
10 Photoelectric conversion element
100 Photoelectrochemical cell
M Electric motor (Electric fan)
41 Transparent electrode
42 Semiconductor electrode
43 Transparent conductive film
44 Substrate
45 Semiconductor layer
46 Light-scattering layer
40 Photoelectrode
20 Dye-sensitized solar cell
CE Counter electrode
E Electrolyte
S Spacer
51 Transparent substrate
52 Transparent electrically conductive film
53 Barrier layer
54 n-type semiconductor electrode
55 p-type semiconductor layer
56 p-type semiconductor film
57 Counter electrode
57a Protrusion

The invention claimed is:

1. A photoelectric conversion element having a laminate structure comprising, provided on an electrically conductive support, a photoconductor layer having a layer of dye-adsorbed semiconductor fine particles, a charge transfer layer, and a counter electrode, wherein the dye is a metal complex dye represented by the following formula (1):

$$M^1L^1L^2Z^1 \tag{1}$$

wherein, in formula (1), $M^1$ represents a metal atom; $Z^1$ represents a monodentate ligand; $L^1$ represents a tridentate ligand represented by formula (L1); and $L^2$ represents a bidentate ligand represented by formula (L2),

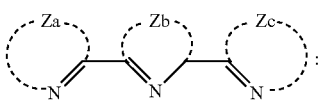

(L1)

wherein, in formula (L1), Za, Zb, and Zc represent a group of non-metallic atoms necessary for forming a 5- or 6-membered ring; and at least one ring formed by Za, Zb or Zc has an acidic group;

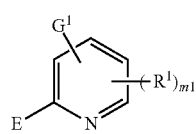

(L2)

wherein, in formula (L2), $R^1$ represents an alkyl group, an alkylthio group, an alkoxy group, a halogen atom, or an aromatic group; m1 represents an integer of 0 to 3; and E is represented by any one of formulae (L2-1) to (L2-6):

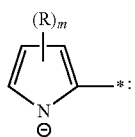 (L2-1)

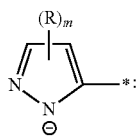 (L2-2)

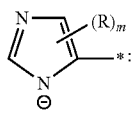 (L2-3)

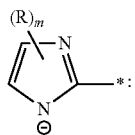 (L2-4)

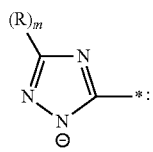 (L2-5)

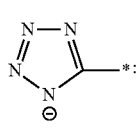 (L2-6)

wherein, in formulae (L2-1) to (L2-6), R represents an alkyl group, an alkoxy group, a halogen atom, an aromatic group, or a heterocyclic group; m represents an integer of 0 or more; the symbol "*" represents a binding site with the pyridine ring; and $G^1$ is represented by any one of formulae (G1-1) to (G1-7):

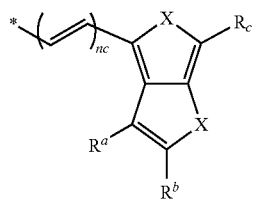 (G1-1)

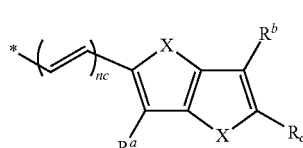 (G1-2)

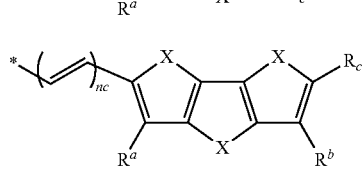 (G1-3)

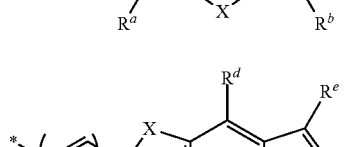 (G1-4)

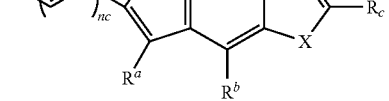 (G1-5)

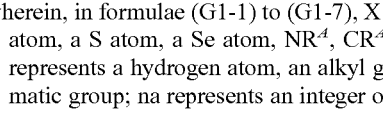 (G1-6)

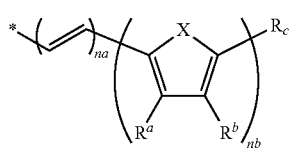 (G1-7)

wherein, in formulae (G1-1) to (G1-7), X represents an O atom, a S atom, a Se atom, $NR^A$, $CR^A_2$, or $SiR^A_2$; $R^A$ represents a hydrogen atom, an alkyl group, or an aromatic group; na represents an integer of 0 to 3; nb represents an integer of 1 to 3; nc represents an integer of 0 to 2; ma represents an integer of 0 to 4; and in formula (G1-1), the sum of na and nb is 2 or more, and $R^a$, $R^b$, $R^d$ and $R^e$ each independently represent a hydrogen atom, an alkyl group, an alkoxy group, an alkylthio group, or an amino group; and $R^c$ represents a hydrogen atom, an alkyl group, an alkenyl group, an alkynyl group, an alkoxy group, an alkylthio group, or an amino group.

2. The photoelectric conversion element according to claim 1, wherein $M^1$ is Ru.

3. The photoelectric conversion element according to claim 1, wherein $L^1$ is represented by formula (L1-2):

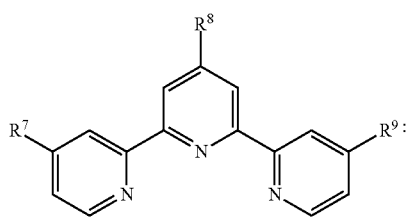 (L1-2)

wherein, in formula (L1-2), $R^7$, $R^8$ and $R^9$ each independently represent a hydrogen atom, an alkyl group, a heteroaryl group, an aryl group, or an acidic group; and at least one of $R^7$, $R^8$ and $R^9$ represents an acidic group.

4. The photoelectric conversion element according to claim 1, wherein the metal complex dye is represented by formula (1-1):

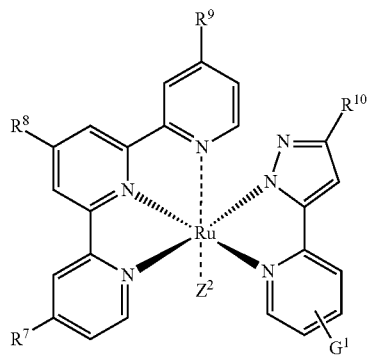

(1-1)

wherein, in formula (1-1), $R^7$ to $R^9$ have the same meanings as those of formula (L1-2); $Z^2$ represents an isothiocyanate group, an isoselenocyanate group, an isocyanate group, a halogen atom, or a cyano group;

$G^1$ has the same meaning as that of formula (L2); and $R^{10}$ represents a hydrogen atom, an alkyl group, a perfluoroalkyl group, an aromatic group, or a heterocyclic group.

5. The photoelectric conversion element according to claim 4, wherein the metal complex dye is represented by formula (1-2):

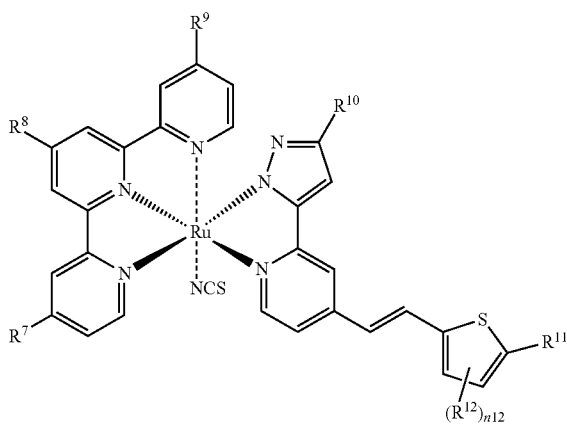

(1-2)

wherein, in formula (1-2), $R^7$ to $R^9$ have the same meaning as those of formula (L1-2); $R^{10}$ has the same meaning as that of formula (1-1); $R^{11}$ represents a hydrogen atom, an alkyl group, an alkoxy group, or an amino group; $R^{12}$ represents an alkyl group, an alkoxy group, or an alkylthio group; and n12 represents an integer of 0 to 2.

6. The photoelectric conversion element according to claim 1, comprising semiconductor fine particles sensitized with a plurality of dyes.

7. The photoelectric conversion element according to claim 6, wherein at least one of the dyes has a maximum absorption wavelength of 590 nm or more in tetrabutylammonium hydroxide methanol solution.

8. The photoelectric conversion element according to claim 1, wherein a co-adsorbent having one or more acid groups is carried on a surface of the semiconductor particles of the semiconductor layer.

9. The photoelectric conversion element according to claim 8, wherein the co-adsorbent is represented by formula (3):

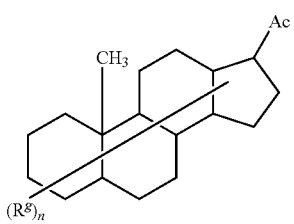

(3)

wherein, in formula (3), Ac represents an acidic group; $R^g$ represents a substituent; and n represents an integer of 0 or more.

10. The photoelectric conversion element according to claim 1, wherein R represents an aromatic group, a heterocyclic group, or an alkyl group which may have a halogen atom.

11. A dye-sensitized solar cell, comprising the photoelectric conversion element according to claim 1.

12. A metal complex dye represented by formula (1):

$$M^1L^1L^2Z^1 \qquad (1)$$

wherein, in formula (1), $M^1$ represents a metal atom; $Z^1$ represents a monodentate ligand; $L^1$ represents a tridentate ligand represented by formula (L1); and $L^2$ represents a bidentate ligand represented by formula (L2);

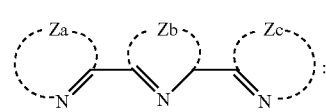

(L1)

wherein, in formula (L1), Za, Zb, and Zc represent a group of non-metallic atoms necessary for forming a 5- or 6-membered ring; and at least one ring formed by Za, Zb or Zc has an acidic group;

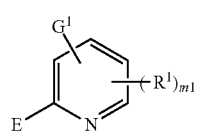

(L2)

wherein, in formula (L2), $R^1$ represents an alkyl group, an alkylthio group, an alkoxy group, a halogen atom, an aromatic group or a heterocyclic group; m1 represents an integer of 0 to 3; and E is represented by any one of formulae (L2-1) to (L2-6):

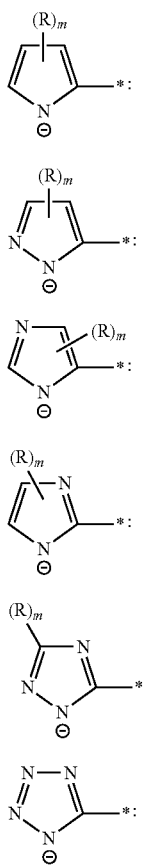

(L2-1)

(L2-2)

(L2-3)

(L2-4)

(L2-5)

(L2-6)

wherein, in formulae (L2-1) to (L2-6), R represents an alkyl group, an alkoxy group, a halogen atom, an aromatic group, or a heterocyclic group; m represents an integer of 0 or more; the symbol "*" represents a binding site with the pyridine ring; and $G^1$ is represented by any one of formulae (G1-1) to (G1-7):

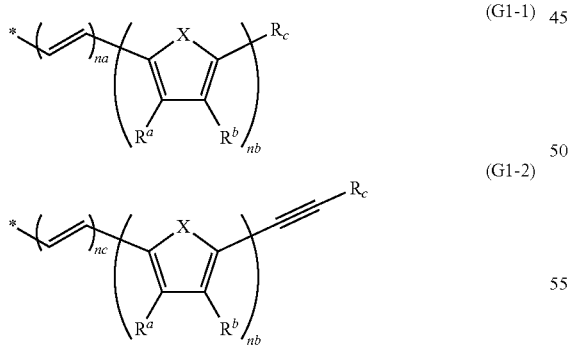

(G1-1)

(G1-2)

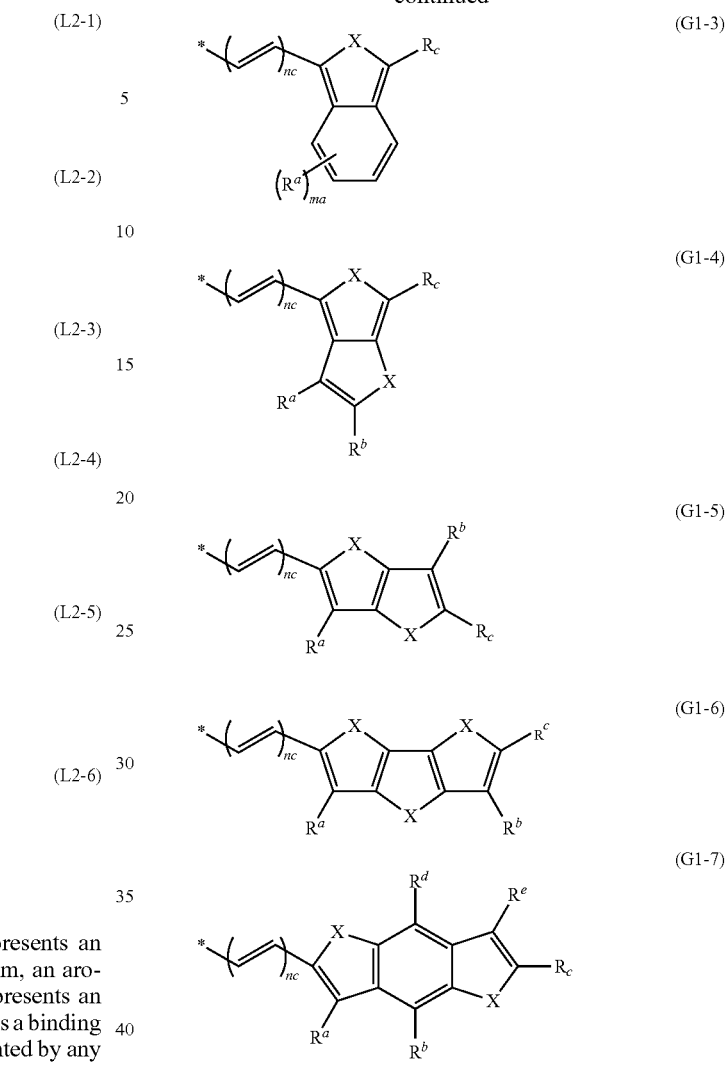

(G1-3)

(G1-4)

(G1-5)

(G1-6)

(G1-7)

wherein, in formulae (G1-1) to (G1-7), X represents an O atom, a S atom, a Se atom, $NR^A$, $CR^A_2$, or $SiR^A_2$; $R^A$ represents a hydrogen atom, an alkyl group, or an aromatic group; na represents an integer of 0 to 3; nb represents an integer of 1 to 3; nc represents an integer of 0 to 2; ma represents an integer of 0 to 4; and in formula (G1-1), the sum of na and nb is 2 or more, and $R^a$, $R^b$, $R^d$ and $R^e$ each independently represent a hydrogen atom, an alkyl group, an alkoxy group, an alkylthio group, or an amino group; and $R^c$ represents a hydrogen atom, an alkyl group, an alkenyl group, an alkynyl group, an alkoxy group, an alkylthio group, or an amino group.

* * * * *